US010028958B2

(12) United States Patent
Miller et al.

(10) Patent No.: US 10,028,958 B2
(45) Date of Patent: Jul. 24, 2018

(54) METHODS OF TREATING CANCER WITH A COMBINATION OF SELECTED MEK1/2 AND AXL INHIBITORS

(71) Applicant: Massachusetts Institute of Technology, Cambridge, MA (US)

(72) Inventors: Miles Aaron Miller, Boston, MA (US); Madeleine Oudin, Boston, MA (US); Aaron Samuel Meyer, Boston, MA (US); Frank B. Gertler, Boston, MA (US); Linda G. Griffith, Cambridge, MA (US); Douglas A. Lauffenburger, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/690,001

(22) Filed: Apr. 17, 2015

(65) Prior Publication Data
US 2016/0067250 A1 Mar. 10, 2016

Related U.S. Application Data

(60) Provisional application No. 62/073,887, filed on Oct. 31, 2014, provisional application No. 61/981,741, filed on Apr. 19, 2014.

(51) Int. Cl.
| *A61K 31/519* | (2006.01) |
| *A61K 31/381* | (2006.01) |
| *A61K 31/437* | (2006.01) |
| *A61K 31/44* | (2006.01) |
| *A61K 39/395* | (2006.01) |
| *C07K 16/38* | (2006.01) |
| *A61K 45/06* | (2006.01) |
| *A61K 31/5025* | (2006.01) |
| *A61K 31/5377* | (2006.01) |
| *A61K 31/5383* | (2006.01) |
| *A61K 31/502* | (2006.01) |
| *A61K 31/506* | (2006.01) |

(52) U.S. Cl.
CPC .......... *A61K 31/519* (2013.01); *A61K 31/381* (2013.01); *A61K 31/437* (2013.01); *A61K 31/44* (2013.01); *A61K 31/502* (2013.01); *A61K 31/506* (2013.01); *A61K 31/5025* (2013.01); *A61K 31/5377* (2013.01); *A61K 31/5383* (2013.01); *A61K 39/3955* (2013.01); *A61K 45/06* (2013.01); *C07K 16/38* (2013.01); *C07K 2317/76* (2013.01)

(58) Field of Classification Search
None
See application file for complete search history.

(56) References Cited

U.S. PATENT DOCUMENTS 8,546,433 B2 * 10/2013 Hitoshi .............. A61K 31/4196
514/383
2013/0078252 A1 3/2013 Wilson et al.

FOREIGN PATENT DOCUMENTS

| EP | 2 570 127 A1 | 3/2013 |
| WO | WO 2012/178038 A1 | 12/2012 |
| WO | WO 2015/161230 A1 | 10/2015 |

OTHER PUBLICATIONS

Britten CD, P13K and MEK inhibitor combinations: examining the evidence in selected tumor types. Cancer Chemother. Pharmacol. 71, 1395-1409, 2013.*
Eder et al. Clin. Cancer Res. 16, 3507-3516, 2010.*
Iida et al., Membrane type-1 matrix metalloproteinase promotes human melanoma invasion and growth. J Invest Dermatol 122,167-176, 2004.*
Holland et al. (R428, a selective small molecule inhibitor of Axl kinase, blocks tumor spread and prolongs survival in models of metastatic breast cancer. Cancer Res. 70, 1544-1554, 2010 (Year: 2010).*
Fremin et al. (From basic research to clinical development of MEK1/2 inhibitors for cancer therapy. J. Hematol. Oncology, 3, 8, 2010. (Year: 2010).*
Huether, A., et al., "Signaling Pathways Involved in the Inhibition of Epidermal Growth Factor Receptor by Erlotinib in Hepatocellular Cancer", *World J. Gastroenterol*, 12(32):5160-5167 (2006).
Kriegs, M., et al., "The Epidermal Growth Factor Receptor Modulates DNA Double-Strand Break Repair by Regulating Non-Homologous End-Joining", *DNA Repair*, 9:889-897 (2010).
Ye, S., el al., "An Anti-Axl Monoclonal Antibody Attenuates Xenograft Tumor Growth and Enhances the Effect of Multiple Anticancer Therapies", *Oncogene*, 29:5254-5264 (2010).
Notification of Transmittal of the International Search Report and the Written Opinion of the International Search Authority for PCT/US2015/026437, "Methods of Reducing Kinase Inhibitor Resistance", dated Sep. 18, 2015.
Gierut et al.; "Network-level effects of kinase inhibitors modulate TNF-α-induced apoptosis in the intestinal epithelium;" *Sci Signal*; Dec. 2015, 8(407); 21 pages.
Gilmartin et al.; "GSK1120212 (JTP-74057) Is an Inhibitor of MEK Activity and Activation with Favorable Pharmacokinetic Properties for Sustained In Vivo Pathway Inhibition;" *Clin Cancer Res*; 17(5) (2011); pp. 989-1000.
Holland et al.; "R428, a Selective Small Molecule Inhibitor of Axl Kinase, Blocks Tumor Spread and Prolongs Survival in Models of Metastatic Breast Cancer;" *Cancer Res*; 70(4), pp. 1544-1554 (2010).
Pettazzoni et al.; "Genetic Events That Limit the Efficacy of MEK and RTK Inhibitor Therapies in a Mouse Model of KRAS-Driven Pancreatic Cancer;" *Cancer Res*; 75(6), (2015); pp. 1091-1101.
Roberts et al.; "Targeting the Raf-MEK-ERK mitogen-activated protein kinase cascade for the treatment of cancer;" *Oncogene* (2007) 26, pp. 3291-3310.

(Continued)

*Primary Examiner* — Elly-Gerald Stoica
(74) *Attorney, Agent, or Firm* — Hamilton, Brook, Smith & Reynolds, P.C.

(57) ABSTRACT

Methods, compounds and kits relating to treating cancer, reducing kinase inhibitor or resistance, and reducing or preventing diminished ectodomain shedding are described.

21 Claims, 23 Drawing Sheets
(21 of 23 Drawing Sheet(s) Filed in Color)

(56) References Cited

OTHER PUBLICATIONS

Bae, D. and S. Ceryak, "Raf-independent, PP2A-dependent MEK Activation in Response to ERK Silencing," Biochem Biophys Res Commun, 385(4): 523-527 (Aug. 2009).
Pearson, G. et al., "Uncoupling Raf1 from MEK1/2 Impairs Only a Subset of Cellular Responses to Raf Activation," The Journal of Biological Chemistry, 275(48): 37303-37306 (Dec. 2000).
Yap, J.L. et al., "Small Molecule Inhibitors of the ERK Signalling Pathway: Towards Novel Anti-cancer Therapeutics," Chem Med Chem, 6(1): 38-48 (Jan. 2011).
Zhou, L. et al., "MEK1 and MEK2 isoforms regulate distinct functions in pancreatic cancer cells," Oncology Reports, 24: 251-255 (2010).
International Preliminary Report on Patentability for Int'l Application No. PCT/US2015/026437, titled: Methods of Reducing Kinase Inhibitor Resistance, dated Oct. 25, 2016.

\* cited by examiner

FIG. 1A
FIG. 1B
FIG. 1C
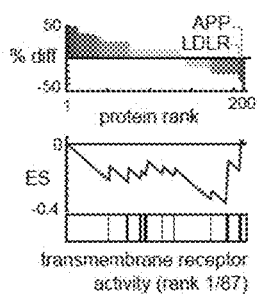
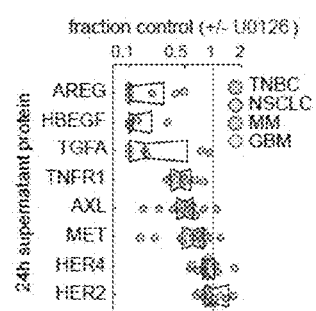
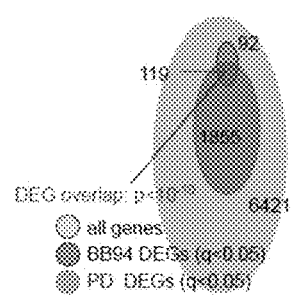
FIG. 1D
FIG. 1E
FIG. 1H
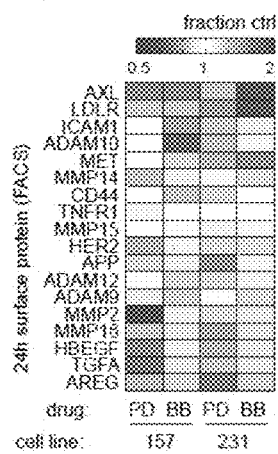
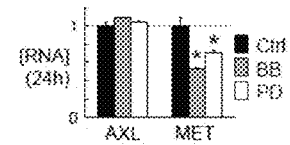
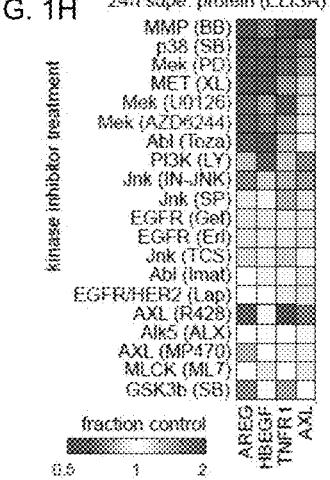
FIG. 1F  FIG. 1G
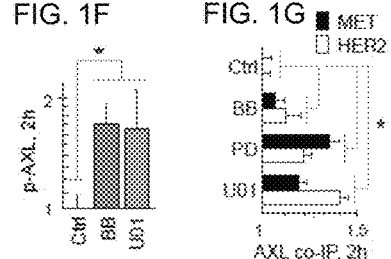

synergistic vs. non-synergistic
gene expression signature

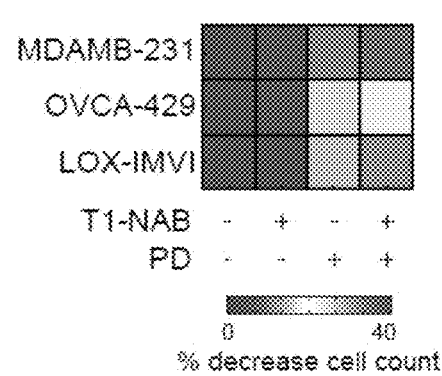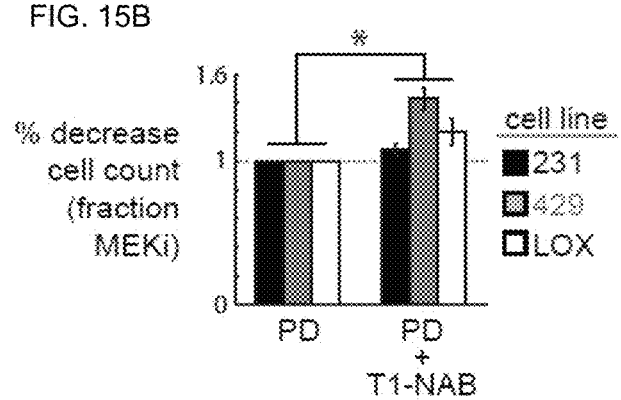
FIG. 15A
FIG. 15B

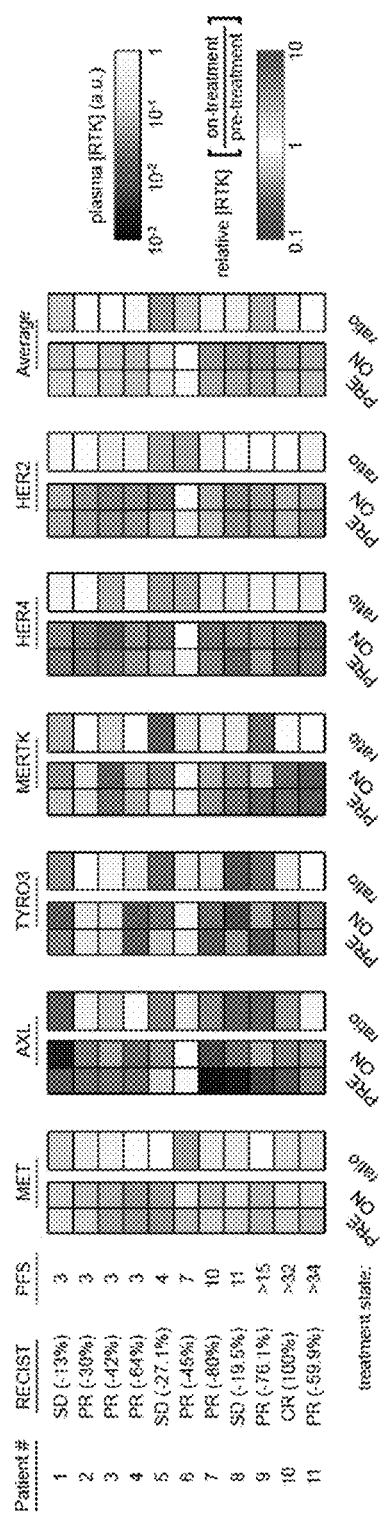

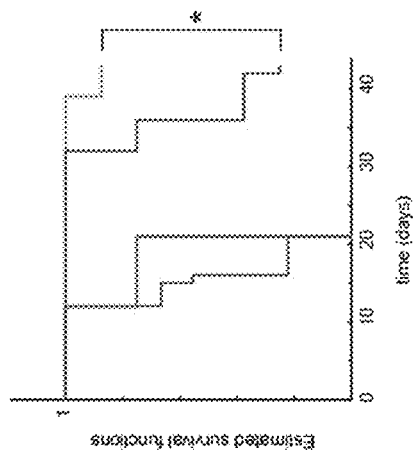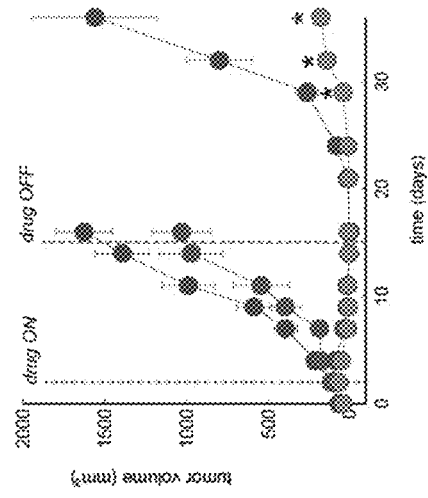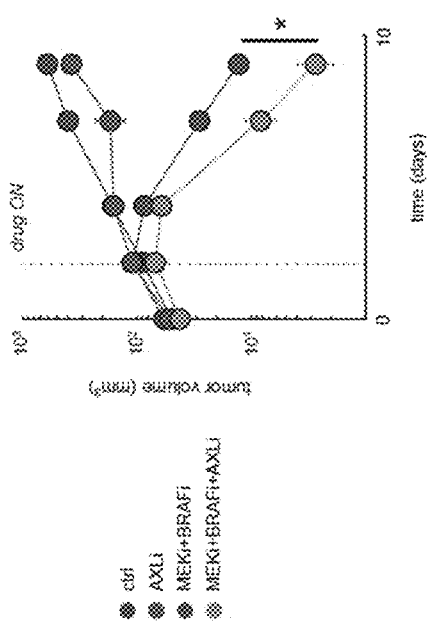

METHODS OF TREATING CANCER WITH A COMBINATION OF SELECTED MEK1/2 AND AXL INHIBITORS

RELATED APPLICATIONS

This application claims the benefit of U.S. Provisional Application No. 61/981,741, filed on Apr. 19, 2014 and U.S. Provisional Application No. 62/073,887, filed on Oct. 31, 2014. The entire teachings of the above applications are incorporated herein by reference.

GOVERNMENT SUPPORT

This invention was made with Government support under Grant Nos. W81WH-13-1-0031 and W81XWH-11-1-0088 awarded by the U.S. Army Medical Research and Material Command and under Grant Nos. R01 CA096504, U54 CA112967, and R01 EB010246 awarded by the National Institutes of Health. The Government has certain rights in the invention.

BACKGROUND OF THE INVENTION

Molecular-targeted cancer therapeutics inevitably fail due to the disease's ability to adapt in response to treatment. Unfortunately, the mechanisms for how this occurs are generally poorly understood, with genetic and gene expression changes accounting for only a fraction of observations. Methods of reducing resistance to such cancer therapeutics are needed.

SUMMARY OF THE INVENTION

Described herein are compositions, methods and kits related to the treatment of a cancer comprising administering combinations of inhibitors such as a mitogen activated protein kinase (MAPK) inhibitor, an AXL inhibitor, a Met inhibitor, a BRAF inhibitor and/or a PI3K inhibitor.

In one aspect, the invention is directed to a method of reducing or preventing resistance to an administered kinase inhibitor, e.g., a receptor tyrosine kinase (RTK) inhibitor in an individual in need thereof comprising preventing the reduction of proteolytic shedding in the individual, for example, by inhibiting AXL, such as by administering an AXL inhibitor.

A method of increasing the efficacy of an administered MAPK inhibitor in an individual in need thereof comprising increasing shedding of sheddase substrates in the individual.

In one aspect, the invention is directed to a method comprising treating a cancer in an individual comprising administering a therapeutically effective amount of a mitogen activated protein kinase (MAPK) inhibitor and one or more of an AXL inhibitor, a Met inhibitor, and a PI3K inhibitor to the individual.

In another aspect, the invention is directed to a method of reducing resistance to a MAPK inhibitor, comprising administering to an individual being treated with the MAPK inhibitor, a therapeutically effective amount of an AXL inhibitor.

In another aspect, the invention is directed to a method of increasing (e.g., reducing attenuation of) efficacy of a MAPK inhibitor, comprising administering to an individual being treated with a MEK inhibitor, a therapeutically effective amount of an AXL inhibitor.

In one aspect, the invention is directed to a method of modulating a tumor in an individual comprising administering a MAPK inhibitor and an AXL inhibitor to the individual.

In some aspects of the methods described herein, the MAPK inhibitor comprises a BRAF inhibitor, MEK1 inhibitor, a MEK2 inhibitor, or a combination thereof. In some aspects, the MAPK inhibitor is selected from the group consisting of U0216, PD325901, AZD6244 (selumetinib), sorafenib, and trametinib (GSK1120212), vemurafenib, and dabrafenib.

In some aspects of the methods described herein, the AXL inhibitor is selected from the group consisting of R428, ($C_{30}H_{34}N_8$), MP-470 (amuvatinib), and XL-880 (foretinib).

In some aspects of the methods described herein, the PI3K inhibitor is BAY 80-9646 (Copanlisib).

The methods described herein can further comprise administering an additional therapeutic agent. In one aspect, the additional therapeutic agent is a metalloproteinase inhibitor (MPi). In another aspect, the additional therapeutic agent is BB94.

In some of the embodiments, the methods described herein comprising treating a cancer, such as any of the cancers described herein. In some aspects, the cancer is a carcinoma, sarcoma, lymphoma, leukemia, or blastoma. In some aspects, the carcinoma is a breast cancer, a melanoma, a lung cancer or an ovarian cancer. In some aspects, the breast cancer expresses low estrogen receptor, progesterone receptor, HER2, or a combination thereof, e.g., triple-negative breast cancer (TNBC). In some aspects, the blastoma is glioblastoma multiforme.

In some aspects of the methods described herein, the combination of inhibitors is administered to the individual at or near the same time. In another aspect, they are not. For example, in one embodiment, a MAPK inhibitor is administered before or after administration of an AXL inhibitor to the individual.

In some aspects, multiple inhibitors, e.g., a MAPK inhibitor and an AXL inhibitor, are administered to the individual in a single formulation. In another aspect, they are administered to the individual in different formulations.

In one aspect of the methods described herein, administering the inhibitors, e.g., a MAPK inhibitor and an AXL inhibitor, reduces tumor growth in the individual. In another aspect, administering the MAPK inhibitor and AXL inhibitor reduces metastasis in the individual.

In some aspects of the methods described herein, the amount of one or more of the inhibitors, e.g., the MAPK inhibitor, AXL inhibitor, or both, is adjusted after monitoring a level of at least one sheddase substrate in the individual's circulation. In a particular aspect, the amount of AXL inhibitor administered is increased (e.g., from it not being administered to it being administered, or from a lower dosage to a higher dosage) if the serum level of a sheddase substrate is higher than normal. In another aspect, the AXL inhibitor is administered if the individual's serum levels of sheddase substrate are determined to be higher than expected, e.g., normal.

In some aspects, the sheddase is A Disintegrin and Metalloproteinase (ADAM). In one aspect, the ADAM is ADAM10 and/or ADAM17.

In some aspects, the sheddase substrate is a receptor tyrosine kinase (RTK), a cytokine receptor, a growth factor ligand, or a combination thereof. In some aspects, the RTK is selected from the group consisting of Met, HER2, HER4, and AXL. In another aspect, the cytokine receptor is TNFR1.

In another aspect, the growth factor ligand is selected from the group consisting of AREG, HBEGF, and TGFα.

In some aspects, the sheddase substrate is a receptor tyrosine kinase (RTK) of the TAM receptor family, including AXL, Tyro3, MerTK, or a combination thereof.

In some aspects, an increase in the level of the one or more sheddase substrates in the individual's circulation indicates a positive treatment response to the combined administration of the MAPK inhibitor and the AXL inhibitor.

In some aspects, the invention includes a method of treating a cancer in an individual comprising administering a therapeutically effective amount of a receptor tyrosine kinase and an agent that prevents reduction of proteolytic shedding.

In some aspects, the invention includes a method of preventing reduction of proteolytic shedding comprising administering a therapeutically effective amount of a TIMP1 antibody.

In some aspects at least one TIMP1 neutralization antibody is administered to prevent reduction of proteolytic shedding.

In some aspects, the invention includes a method of reducing diminishment of proteolytic ectodomain shedding following administration of a Map kinase inhibitor, comprising administering a therapeutically effective amount of a receptor tyrosine kinase and an AXL inhibitor.

In some aspects the invention includes compounds comprising one or more of the compounds described herein, such as a kinase inhibitor (e.g., a RTK inhibitor such as a MEK inhibitor). In some aspects, the invention encompasses a kit, e.g., a kit comprising a kinase inhibitor. In some aspects the kit includes instructions.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments of the invention, as illustrated in the accompanying drawings.

FIG. 1A-1H illustrates that MEK inhibition widely reduces substrate shedding and leads to accumulation of surface AXL. FIG. 1A, top graph, shows differentially detected supernatant proteins from MDAMB231 treated with PD325901 for 24 h, measured by Ab-microarray (n=4). FIG. 1A, middle graph, shows the enrichment score (ES) trace for the top-ranked gene-set. FIG. 1A, bottom graph, shows vertical bars that indicate the location of proteins in the top-ranked gene-set. FIG. 1B shows that MEKi for 24 h with U0126 reduces supernatant accumulation of sheddase substrates (measured by ELISA). Each dot represents a different cell line (n≥2; see FIG. 8B for data). FIG. 1C is a Venn diagram of DEGs from RNA microarray analysis of MDAMB231 treated with PD325901 or BB94 for 24 h (q=FDR-corrected p-value; n≥2). FIG. 1D shows changes in surface levels of implicated sheddase substrates following PD325901 or BB94 treatment in two TNBC cell lines (MDAMB157 and MDAMB231; n=3). FIG. 1E shows MEKi or MPi reduces gene expression of MET but not AXL (corresponds to RNA microarray data; n≥2; *p<0.05). FIG. 1F shows total AXL pY increases following 2 h BB94/U0126 in MDAMB231 (*p=0.004, pooled t-test, n=5 total reps). FIG. 1G shows that AXL association with MET and HER2 increases following 2 h MEK/BB94 inhibitor treatment in MDAMB231, determined by s-EGS crosslinking and a bead-based co-I.P. (bars denote pooled t-test, p<0.05, n=3). FIG. 1H shows that diverse kinase inhibitors (labeled as drug target followed by drug name) affect supernatant ADAM-substrate concentrations in MDAMB231 (n≥2).

FIG. 2A shows that breast cancer patients exhibit increased circulating RTKs. Individual RTK levels were normalized to the average value across all n=10 control and n=19 patient samples. FIG. 2B shows that while individual RTK levels did not significantly change with disease, the combined minimum measured across all four RTKs for a given patient was significantly increased with disease and was dependent upon AXL (p=0.02). FIG. 2C shows the change in total and phospho-RTK levels following 24 h BB94 treatment. Each dot represents one of 19 cell lines tested (see FIG. 9B for data). FIG. 2D shows that changes in the protein levels listed on the left were measured across a panel of TNBC cell lines following 24 h BB94 treatment (see FIG. 9C for data). The heat map shows hierarchical bi-clustering of the spearman correlations between protein drug responses, across the panel of cell lines. Co-clustering with surface-AXL is highlighted in green (first six shown). FIG. 2E shows that BB94 increases phosphosignaling in an AXL-dependent manner, measured by bead-based immunoassay in MDAMB231 after 2 h treatment with AXL inhibitor R428 (n=8). FIG. 2F shows AXL and MET siRNAs reduce compensatory p-JNK signaling, measured following 3 h drug treatment and 48 h siRNA treatment in MDAMB231 (*p=0.014, pooled t-test, n=2 reps/cond).

FIG. 3A shows ADAM10 and ADAM17 siRNA and proADAM10 inhibitor reduce 24 h supernatant accumulation of AXL compared to their respective controls, measured by ELISA (*p<0.05; n≥2). FIG. 3B illustrates live-cell immunostaining showing that ADAM10 and ADAM17 siRNA treatment increases surface AXL in MDAMB231 and MDAMB157, 72 h post-transfection. FIG. 3C shows on-bead digest of immunoprecipitated AXL by recombinant ADAM-10 and -17. Full-length AXL was immunoprecipitated from cell lysate and incubated with recombinant protease for 4 h. Reaction supernatant (left) and resin (right) were boiled in denaturing sample buffer, run on an SDS-PAGE gel, and blotted for AXL. Bands show full-length (100-150 kDa) and cleaved c-terminal (55 kDa) AXL. FIG. 3D shows quantification of FIG. 3C, across n=2 replicate experiments. FIG. 3E shows that BB94 increases mitotic index, measured by FACS, in an AXL-dependent manner (bars denote p<0.05; n≥4 total reps; pooled two-tailed student's t-test). FIG. 3F shows that ADAM17 knockdown increases cell count only in the absence of the AXL inhibitors R428 and MP470 (*p=0.047; n=4 reps/cond), measured 24 h after AXLi, 72 h after transfection.

FIG. 4A shows that MEKi reduces ADAM10 and ADAM17 catalytic activities in MDAMB231, inferred using PrAMA (*p<0.05; n=4 reps/cond). FIG. 4B illustrates replicate western blots that show increased ADAM17 dimerization with MEKi. MDA-MB231, MDA-MB157, and BT549 cell lines were treated with PD325901 for 3 h, cross-linked with s-EGS treatment, and lysed. Immunopurified ADAM17 was run on an SDS-PAGE gel and blotted for ADAM17. Monomer runs at 110 kDa, dimer runs at roughly 200 kDa. FIG. 4C shows quantification of ADAM17 homodimerization shown in FIG. 4B (p=0.001; pooled two-tailed student's t-test; n=6 total reps). FIG. 4D shows that 24 h PD325901 treatment decreases supernatant TIMP-1 and -3 in MDAMB231, measured by Ab-microarray (*p<0.05; n=4). FIG. 4E illustrates live-cell immunostaining showing that TIMP1 knockdown reduces surface AXL in MDAMB231, 24 h after PD325901 treatment and 72 h after transfection (*p<0.05; n=3). FIG. 4F is a graph of live-cell immunostaining showing that MEKi increases surface TIMP1 in MDAMB231 and MDAMB157 (bar denotes p<0.05; pooled t-test; n≥2 reps/cond). FIG. 4G is a graph of live-cell immunostaining showing that surface TIMP1 decreases, 72 h after transfection in MDAMB231 (*p<0.05; n≥2 reps/cond). FIG. 4H shows that phospho-A17 (ADAM-17 phosphorylation) decreases following MEKi (p=0.03, pooled two-tailed student's t-test; n=2 reps/cond).

FIG. 5A shows RNA expression, or summed RNA expression for gene combinations, significantly correlates with resistance to two MEK inhibitors (PD325901 and AZD6244) across over 450 cell lines tested in the CCLE (p-values from permutation test). FIG. 5B shows that U0126 and PD325901 increase surface AXL (measured by live-cell immunostaining) more in cell lines showing synergistic inhibition of proliferation from dual AXLi/MEKi (p=0.01). Dots represent data from 10 cell lines and two drug combinations (see FIG. 12B-12C). FIG. 5C shows that RNA expression levels were compared between cell lines that exhibited AXLi/MEKi synergy (n=5) and those that did not (n=4; see FIG. 12C). While individual gene expression did not significantly correlate with synergy, the summed RNA expression of all four genes ("combo") did. FIG. 5D shows changes in 21 protein levels (see FIG. 12D) measured across a panel of cell lines following 24 hour U0126 treatment and then ranked according to their spearman correlation with U0126 resistance in a 72 hr cell-growth assay (see FIG. 12D), across the panel of the same cell lines.

FIG. 6A shows that dual AXLi/MEKi reduced tumor growth more than either treatment individually (1 mg/kg PD325901; 30 mg/kg R428). Bars denote p<0.05 (n≥7). FIG. 6B shows that dual AXLi/MEKi reduces metastasis after 21 days of treatment, corresponding to FIG. 6A (bars denote p<0.05, n≥7). FIG. 6C shows that representative immunostaining of xenograft LM2 primary tumors 21 days after PD325901 treatment (tumors correspond to FIG. 6A), showing up-regulation of AXL, and MET to a lesser degree, near the tumor edge. Antibodies targeted extracellular domain of the receptors. Scale bar=100 μm. FIG. 6D shows that, corresponding to FIG. 6C, AXL ectodomain staining significantly increases following 21 days of MEKi near the tumor edge. Plot shows mean (thick line)+/−S.E.M. (shaded area) for staining intensity measured within a 140 μm sliding window from the tumor edge (*p=0.013; n≥3 tumors/group). FIG. 6E shows that AXL ectodomain staining in primary tumors significantly increases only in the MEKi group (*p=0.013, n≥3), corresponding to FIG. 6C-6D. FIG. 6F shows that circulating mouse xenograft plasma levels of soluble AXL, MET, and TNFR1 decrease with treatment. Plasma was collected at day 21 corresponding to FIG. 6A. Bars denote p<0.05, pooled t-test, n≥6 reps/cond. FIG. 6G is a schematic showing the mechanism of bypass RTK signaling upon MEK inhibition.

FIG. 8A, top panel, shows differentially detected supernatant proteins from PD325901-treated MDAMB231, measured by Ab-microarray, plotted as percent difference with control (reproduced from FIG. 1A). FIG. 8A, middle panel, shows the enrichment score trace for bottom-ranked gene-set in GSEA of Ab-microarray data. FIG. 8A, bottom panel, shows vertical bars indicating location of proteins in the bottom gene-set, corresponding to the waterfall plot at top. FIG. 8B shows that BB94 and MEKi reduce supernatant levels of sheddase substrates across a panel of cell lines. Supernatant receptor concentrations were measured in 13 cell lines following 24 h treatment with either BB94 (left panel) or PD325901 (right panel). Individual cell line data is shown in the heatmap (bottom panel), which also corresponds to FIG. 1B. FIG. 8C Corresponding to FIG. 1C, top two panels show volcano plots that display statistical significance as a function of fold-change in RNA expression after 24 h treatment with BB94 or PD325901 in MDAMB231. Each dot represents a gene, measured by RNA microarray. The bottom panel shows correlation (p=3·10$^{-6}$; two-tailed permutation test) between fold-change in RNA expression following either BB94 or PD325901 treatment, corresponding to microarray data in the top two plots. Statistically significant DEGs are denoted by scatter dots, and insignificant DEGs are represented by colored contour lines to show spatial density. FIG. 8D shows statistically significant gene set enrichment scores for gene sets depleted in PD325901-treated cells compared to the control sample, using data in FIG. 8C. FIG. 8E shows normalized changes in protein surface levels relative to altered RNA expression following 24 h inhibitor treatment. FIG. 8E, left panel, shows surface protein levels measured by FACS in MDAMB231 following 24 h treatment with either BB94 or PD325901, reproduced from FIG. 1D. FIG. 8E, middle left panel shows processed expression values from RNA microarray, using data in FIG. 8C. FIG. 8E, middle right panel, shows normalized RNA expression values, corresponding to the plot of the middle left panel. FIG. 8E, right panel shows surface protein fold-change normalized to RNA fold-change following inhibitor treatment, sorted according to average value across both inhibitor treatments. FIG. 8F shows fraction relative to control of MET and AXL receptor levels following treatment with either BB94, U0126, or PD325901, measured in 16 cell lines. Each dot describes changes in AXL and MET in an individual cell line following treatment with BB94 and either U0126 or PD325901. Significant correlation exists between surface receptor up-regulation following either MPi or MEKi (p=0.01, two-tailed permutation test). FIG. 8G shows receptor levels measured by FACS following 3 h treatment with various inhibitors in MDAMB231.

FIG. 9A shows combined, but not individual, circulating RTK levels are increased in breast cancer patients in a statistically significant manner (full data shown in FIG. 2A). The combined minimum levels of the RTKs indicated at left were determined for each sample, and corresponding p-values were calculated to compare healthy (n=10) vs. disease (n=19) groups (two-tailed Student's t-test). The MET/AXL/HER4/HER2 signature at bottom corresponds to the combination signature reported in FIG. 2B. FIG. 9B shows the corresponding data to FIG. 2C—a heat map display of relative changes in total and phosphorylated full-length RTKs after 24 h treatment with BB94 across a panel of cell lines, as measured by bead-based immunoassay (nd=not detected). FIG. 9C shows the corresponding data to FIG. 2D—a heatmap display of relative changes in total and phosphorylated levels of RTKs and downstream proteins (measured by bead-based immunoassay), along with total surface levels of AXL and MET (measured by live-cell immunostaining) following 24 h treatment with BB94, across a panel of TNBC cell lines (na=not assessed). FIG. 9D-9E are graphs of validation of siRNA knockdown for AXL (FIG. 9D) and MET (FIG. 9E) using live-cell immunostaining in MDAMB231 and MDAMB157 (*p<0.05; n≥2 reps/cond). FIG. 9F is a graph showing siRNA knockdown of AXL and to a lesser extent MET, reduces compensatory p-Jnk levels following 3 hr treatment with BB94, U0126, or PD325901.

FIG. 11A: ADAM-17 was immunoprecipitated from whole-cell MDAMB231 lysate roughly 3 h following inhibitor treatment, and was then incubated with a fluorogenic peptide substrate to determine activity. Results show no significant change in activity after immunoprecipitation. FIG. 11B-11C show Phospho-ADAM17 decreases following 3 h MEKi (p=0.03, pooled t-test; n=2 reps/cond; FIG. 11C shows replicate western blots). FIG. 11D: Live-cell immunostaining shows relatively minor changes in ADAM-10 and -17 surface levels following MEKi. Measurements were taken 1, 2, and 3 h following inhibitor treatment and averaged (*p=0.02, n=3). FIG. 11E: Live-cell immunostaining of TIMP-1 and TIMP-3 in MDAMB231 validates siRNA knockdown (*p<0.05; n≥2 reps/cond).

FIG. 12A is a graph of cell count that was measured at 72 h following treatment with R428, U0126, PD325901, or a combination thereof. Columns correspond to cell lines listed at bottom. FIG. 12B shows that AXLi/MEKi synergy was determined according to a model of bliss independence, defined here such that values >1 denote synergistic interaction. Cell lines are ordered according to average synergy for the two drug combinations. FIG. 12C shows that surface AXL was measured by live-cell immunostaining 24 hours following treatment with either U0126 or PD325901. FIG. 12D shows correlating changes in protein levels following U0126 treatment (see FIG. 5D). Left panel shows relative levels of total and phosphorylated proteins (determined by bead-based immunoassay) and surface AXL and MET (determined by live-cell immunostaining) following 24 hr treatment with U0126 across a panel of cell lines. Right panel shows the cell count following 72 hour treatment with U0126, corresponding to cell lines at left panel.

FIG. 13A illustrates a heatmap representing OVCA-429 ovarian cancer cells treated with varying concentrations of trametinib or R428 for 72 h, in the presence or absence of 10 uM BB94. Cell count was then assessed, shown here by heatmap color and number after normalization to the untreated control. FIG. 13B is a graph of cell count data from combination drug treatments (e.g., shown in FIG. 13A) fit to a model of Loewe synergy, yielding the synergy interaction term α. Addition of BB94 reduced synergy for MDAMB-231 treated with PD325901 and R428, as well as for OVCA-429 treated with trametinib and R428 (p<0.05, two-tailed jackknife test, n=16 measurements over n=2 reps).

FIG. 15A-15B illustrate that TIMP1 neutralization increases MEKi efficacy. FIG. 15A is a heatmap showing that 24 h pre-treatment with a TIMP1 neutralization antibody (T1-NAb) followed by co-treatment with PD325901 led to enhanced reduction in cell count at 72 h. FIG. 15B is a graph showing that T1-NAb co-treatment increases the effect of PD325901 across multiple cell lines, normalized to the effect-size of PD325901 alone, for each cell line (*p=0.001, pooled two-tailed t-test, n=18 reps).

DETAILED DESCRIPTION OF THE INVENTION

Figure 2A:
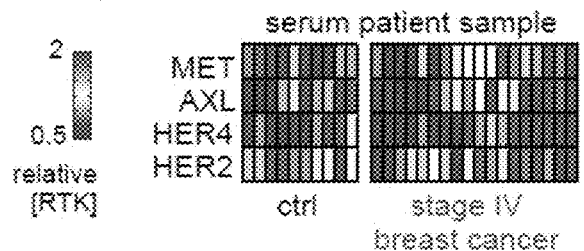
FIG. 2A-2F illustrates that direct sheddase inhibition leads to RTK accumulation and compensatory MAPK signaling.

A description of example embodiments of the invention follows.

Kinase inhibitor resistance often involves up-regulation of "bypass" signaling pathways, frequently without mechanistic explanation. Here, it is shown that extracellular proteomic rewiring unexpectedly elicits drug resistance. Proteolytic shedding of surface receptors, which can provide negative feedback on signaling activity, reduces upon kinase inhibitor treatment and drives enhanced bypass signaling. In particular, MEK inhibition broadly decreases shedding of multiple RTKs across a panel of cancer cell types; these RTKs include MET, HER2, HER4, and most prominently, AXL, shown as an ADAM10 and ADAM17 substrate. Combined MEK/AXL inhibition synergistically reduces tumor growth and metastasis in a mouse xenograft model. Breast cancer patients exhibit increased serum levels of soluble RTKs, while levels of RTKs in circulation decrease following MEK inhibition in the xenograft model.

Described herein is a previously unappreciated and targetable post-translational mechanism of emergent drug resistance with implications for the design and monitoring of cancer therapies. Kinase inhibitors, particularly those targeting ERK pathway signaling via MEK1/2, cause broad changes on the surface of tumor cells due to widely reduced protease activity. As a result, tumor signaling pathways become effectively rewired to circumvent the intended action of the drug treatment. The potential for clinically detecting and overcoming such adaptive resistance is demonstrated herein.

Moreover, expression of a drug's target often fails to predict efficacy, partly due to "bypass" signaling, whereby inhibition of one signaling pathway leads to compensatory signaling through alternative routes. Previous work has largely focused on how intracellular processes such as gene expression changes and genetic mutations contribute to bypass signaling and drug resistance. For example, reports have found that targeting mitogen-activated-protein-kinase (MAPK) signaling through MEK or B-RAF inhibition leads to the up-regulated transcription of multiple receptor tyrosine kinases (RTKs) (Duncan, J. S., et al. Dynamic reprogramming of the kinome in response to targeted MEK inhibition in triple-negative breast cancer. Cell 149, 307-321 (2012).; Nazarian, R., et al. Melanomas acquire resistance to B-RAF (V600E) inhibition by RTK or N-RAS upregulation. Nature 468, 973-977 (2010); Turke, A. B., et al. MEK inhibition leads to PI3K/AKT activation by relieving a negative feedback on ERBB receptors. Cancer Res 72, 3228-3237 (2012)

However, genetic and gene expression changes account for only a fraction of observed bypass signaling. Many drug responses observed at the level of protein activity cannot be simply attributed to upstream genetic or transcriptional modifications (Liu, L., et al. Novel mechanism of lapatinib resistance in HER2-positive breast tumor cells: activation of AXL. Cancer Res 69, 6871-6878 (2009); Serra, V., et al., PI3K inhibition results in enhanced HER signaling and acquired ERK dependency in HER2-overexpressing breast cancer. Oncogene 30, 2547-2557 (2011); Duncan et al., 2012; Turke et al., 2012). Importantly, this observation carries substantial implications in the clinic where many strategies for designing and monitoring an individual's therapeutic course rely largely on genetic or transcriptional information (De Mattos-Arruda, L., et al., Circulating tumour cells and cell-free DNA as tools for managing breast cancer. Nat Rev Clin Oncol 10, 377-389 (2013)). Despite the frequent observation of bypass signaling via post-translational modification, little mechanistic insight has been provided to explain or predict such adaptations and their consequent impact on drug resistance.

This work investigates several cancer types where bypass signaling has been especially noted (Duncan et al., 2012; Turke, A. B., et al., Preexistence and clonal selection of MET amplification in EGFR mutant NSCLC. Cancer Cell 17, 77-88 (2010); Nazarian et al., 2010; Akhavan, D., et al. De-repression of PDGFRbeta transcription promotes acquired resistance to EGFR tyrosine kinase inhibitors in glioblastoma patients. Cancer Discov 3, 534-547 (2013)), and focuses primarily on triple-negative breast cancer (TNBC), a subtype of breast cancer classified by low expression of estrogen receptor, progesterone receptor, and HER2. TNBC carries a relatively poor prognosis and, despite recent clinical trials, no targeted therapies are approved for TNBC. Targeted MEK inhibition (MEKi) represents one promising therapeutic strategy. RAF/MEK/ERK mitogenic phospho-signaling is up-regulated in many cancers including TNBC (Bartholomeusz, C., et al., High ERK protein expression levels correlate with shorter survival in triple-negative breast cancer patients. Oncologist 17, 766-774 (2012); Zardavas, D., et al., Emerging targeted agents in metastatic breast cancer. Nat Rev Clin Oncol 10, 191-210 (2013)), and clinical trials have recently been completed or are ongoing in several cancers including TNBC (Zardavas et al., 2013). Moreover, MEKi carries further importance in the context of cellular drug response, given many other relevant drug targets including various RTKs are upstream of MEK and indirectly affect its activity. Although MEKi is known to drive bypass signaling in TNBC, many of the observed alterations, notably heightened AXL signaling, have yet to be mechanistically explained (Duncan et al., 2012).

Relatively little attention has been paid to how the tumor-derived extracellular proteome changes in response to targeted kinase inhibitor treatment, and how such changes directly impact bypass signaling and drug efficacy. Here, extracellular proteomic rewiring is identified as a major and unexpected post-translational mechanism of bypass signaling that complements other pathways of drug resistance. Proteolytic shedding of surface receptors, which can provide negative feedback on signaling network activity, is dramatically reduced upon kinase inhibitor treatment resulting in enhanced bypass signaling. In particular, inhibition of kinase pathways such as ERK, via MEK1/2, caused broadly diminished A Disintegrin and Metalloproteinase (ADAM)-mediated RTK ectodomain shedding and consequently increased signaling through other pathways that support mitogenesis. As seen, for example, in Example 1, herein, MEKi decreased shedding of multiple RTKs across a panel of cancer cell lines, including TNBC. These RTKs include MET, HER2, HER4, and, most prominently, AXL, shown here as an ADAM10 and ADAM17 substrate.

ADAM10 and ADAM17 function as the principal "sheddases" of the cell surface that are responsible for shedding the ectodomains of hundreds of transmembrane substrates. ADAM17 is clinically over-expressed in many cancers including TNBC (McGowan, P. M., et. al., ADAM-17 expression in breast cancer correlates with variables of tumor progression. Clin Cancer Res 13, 2335-2343 (2007)), with activity governed by MAPK signaling activity that is also frequently dysregulated (Bartholomeusz et al., 2012). ADAM17 is considered a promising drug target for its part in shedding EGF-family growth factor ligands from the surface of cancer cells, a process that mediates ErbB-family receptor signaling in an autocrine manner (Gooz, M., ADAM-17: the enzyme that does it all. Crit Rev Biochem Mol Biol 45, 146-169 (2010); Duffy, M. J., et al., The ADAMs: New Therapeutic Targets for Cancer? Cancer Targeted Drug Delivery, 273-287 (2013)). The results described herein confirm that MEKi directly alters ADAM17 proteolytic activity through its diminished phosphorylation and enhanced homodimerization. (See, for example, Example 4) Also, the results show that reduced RTK shedding is in part dependent on the recruitment of endogenous Tissue Inhibitor of Metalloproteinase 1

(TIMP1) to the cell surface following MEKi. It was also observed that MEKi effectively reduces the shedding of multiple EGF-ligands (see Duffy et al., 2013). However, reduced ADAM10 and ADAM17 activities also led to the broadly reduced shedding of several classes of receptors, including those for cytokines, lipoproteins, extracellular matrix components, and growth factor ligands themselves. It was discovered that RTK proteolysis, more than ligand shedding, can play an unexpectedly prevalent role in bypass signaling resulting from sheddase down-regulation. Increased JNK pathway activity and cell proliferation in culture arose from decreased AXL and MET shedding following treatment with metalloproteinase inhibitors. Overall, these results have significant implications for the consideration of ADAM10 and ADAM17 as cancer drug targets, especially in patients exhibiting high levels of RTK shedding.

Relevant to clinical monitoring, the results described herein show that breast cancer patients exhibit concomitant increases in serum levels of soluble HER2, HER4, MET, and AXL. (See, for example, Example 2). In addition, levels of RTKs in circulation decreased following MEKi in an orthotopic xenograft mouse model of breast cancer. (See, for example, Example 5). Given the role of AXL in mediating drug resistance in culture, the effect of dual treatment with MEK and AXL inhibitors in the xenograft model was tested, and the results described herein show that combined inhibition of MEK and AXL synergistically reduced tumor growth and metastasis. (See, for example, Example 5). Altogether, these findings demonstrate that extracellular proteomic rewiring through reduced proteolytic receptor shedding represents a surprising mechanism for bypass signaling in acquired cancer drug resistance.

Figure 7:
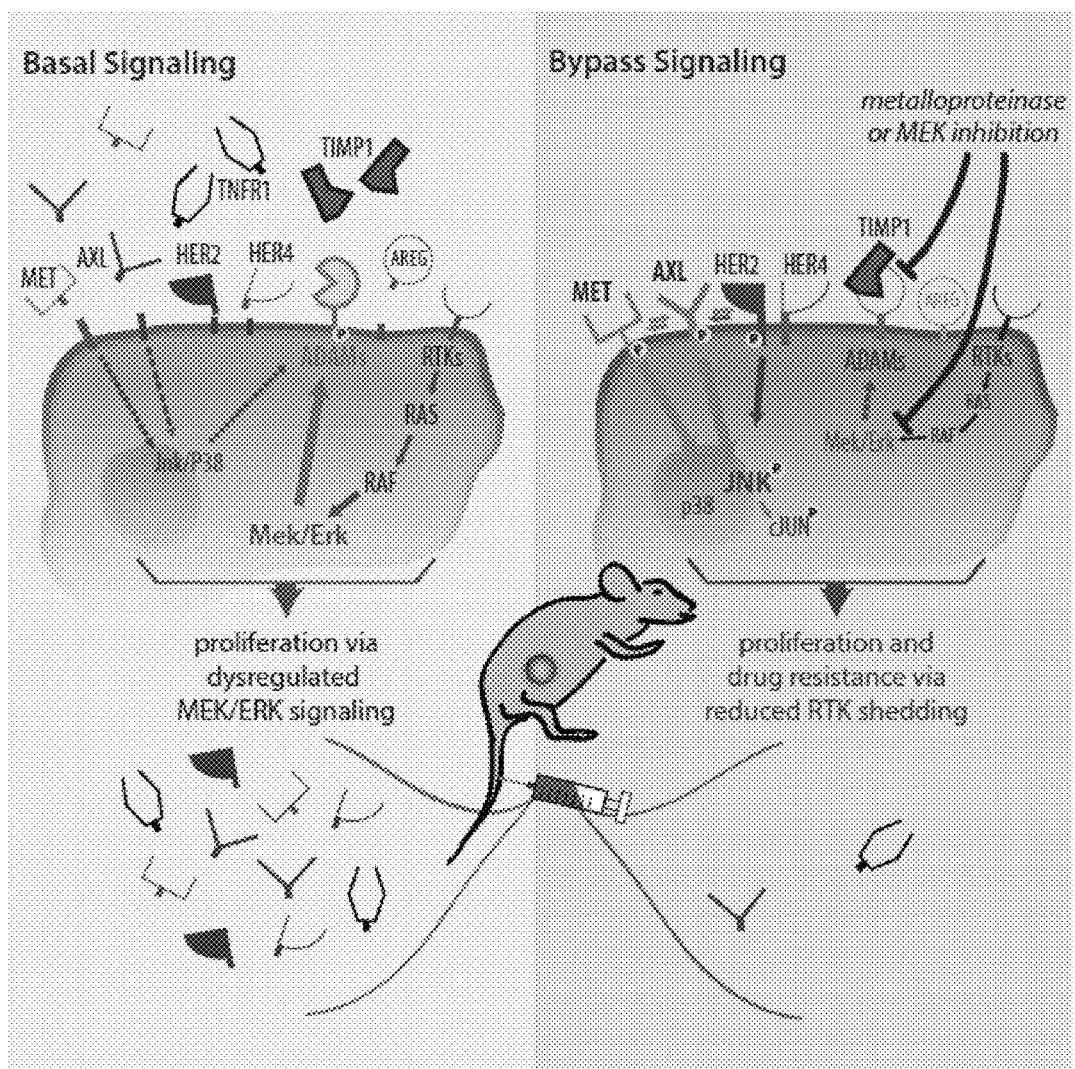
FIG. 7 illustrates an overview of bypass signaling and kinase inhibitor resistance via reduced proteolytic RTK shedding.

A previously unappreciated and targetable mechanism of bypass cancer cell signaling with implications for the design and monitoring of cancer therapies was studied (FIG. 7) Inhibition of multiple signaling pathways, particularly ERK signaling through MEK1/2, reduced proteolytic RTK shedding and led to enhanced mitogenic signaling through bypass kinase pathways including JNK. Numerous examples of increased RTK signaling activity have been observed following targeted kinase inhibitor treatment, often with little mechanistic explanation outside of transcriptional up-regulation (Liu et al., 2009; Duncan et al., 2012; Serra et al., 2011; Zhang, Z., et al. Activation of the AXL kinase causes resistance to EGFR-targeted therapy in lung cancer. Nat Genet 44, 852-860 (2012)). MEK and PI3K kinase inhibition have been shown to enhance the signaling of sheddase substrates including HER2 (Serra et al., 2011; Turke et al., 2012) and AXL (Duncan et al., 2012; Byers, L. A., et al., An epithelial-mesenchymal transition gene signature predicts resistance to EGFR and PI3K inhibitors and identifies Axl as a therapeutic target for overcoming EGFR inhibitor resistance. Clin Cancer Res 19, 279-290 (2013)). It was shown here that MEK and PI3K inhibition both reduce RTK shedding. The direct inhibition of RTKs also give rise to bypass signaling. For example, enhanced AXL signaling mediates resistance to the EGFR/HER2 inhibitor lapatinib, even in the absence of AXL transcriptional up-regulation (Liu et al., 2009). Given this work and others (Miller, M. A., et al. ADAM-10 and -17 regulate endometriotic cell migration via concerted ligand and receptor shedding feedback on kinase signaling. Proc Natl Acad Sci USA 110, E2074-E2083 (2013); Miller, Miles Aaron. Understanding and Targeting Network-Level Sheddase Regulation in Invasive Disease. MIT, Submitted to the Department of Biological Engineering in partial fulfillment of the requirements for the degree of Doctor of Philosophy Thesis, 2013) have shown EGFR inhibition and lapatinib can reduce sheddase activity, here proteolytic receptor shedding is a possible mechanism contributing to these observations. Although transcriptional reprogramming and chromosomal amplification significantly affect bypass signaling (Oxnard, G. R., et al., Acquired resistance to EGFR tyrosine kinase inhibitors in EGFR-mutant lung cancer: distinct natural history of patients with tumors harboring the T790M mutation. Clin Cancer Res 17, 1616-1622 (2011); Nazarian et al., 2010), these processes often fail to fully describe signaling network dynamics following drug treatment; this especially holds true for AXL, which often exhibits little transcriptional up-regulation in response to kinase inhibitor treatment despite sharply enhanced activity (Liu et al., 2009; Duncan et al., 2012).

Figure 4A:
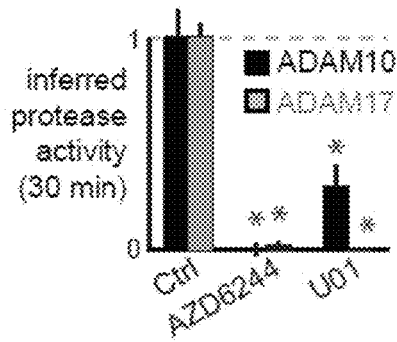
FIG. 4A-4H illustrates that MEK inhibition reduces sheddase activity via increased homodimerization and TIMP1 association.
Figure 8A:
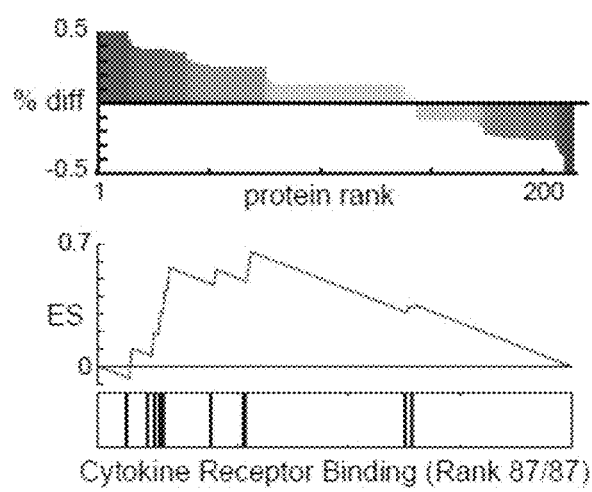
FIG. 8A-8G.
Figure 8B:
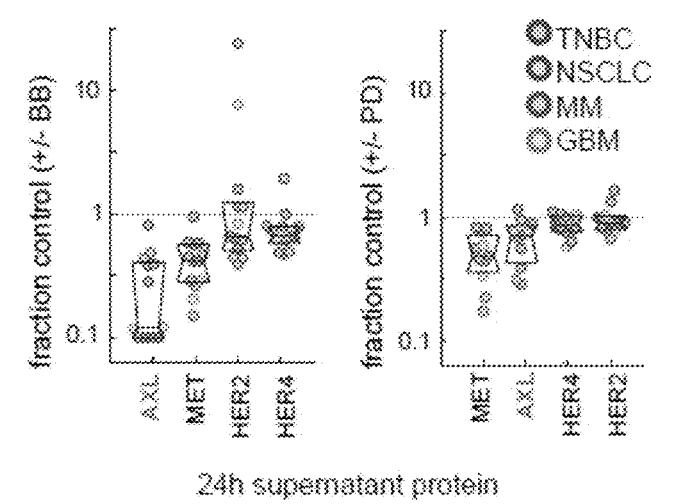
Figure 8B:
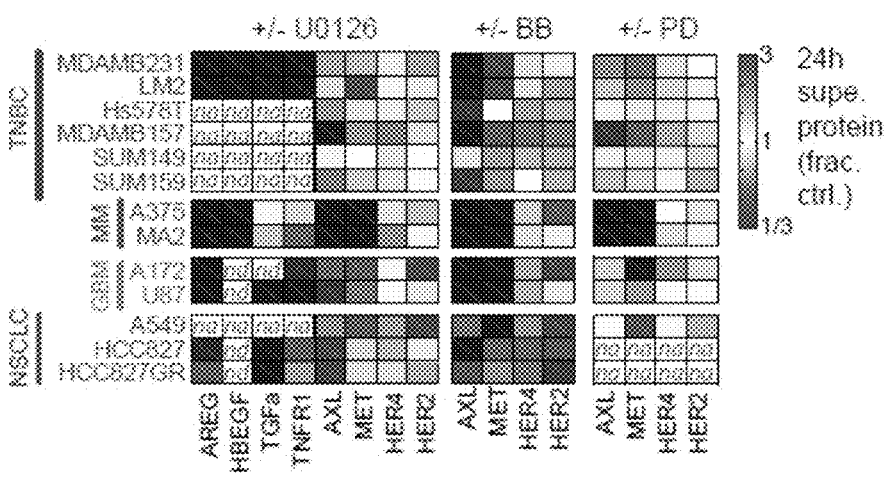
Figure 8C:
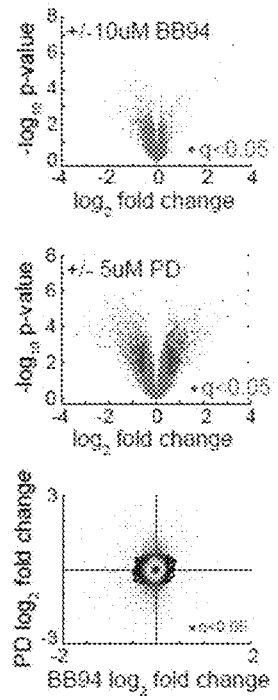
Figure 8D:
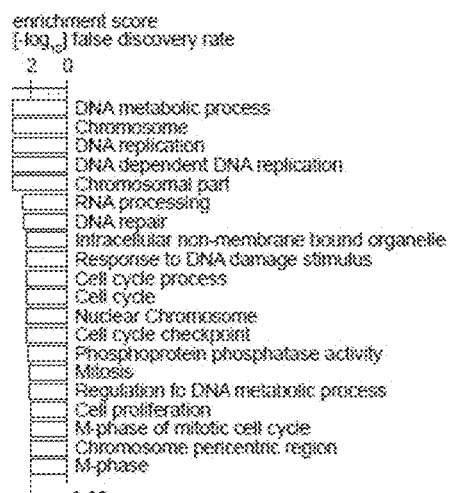
Figure 8E:
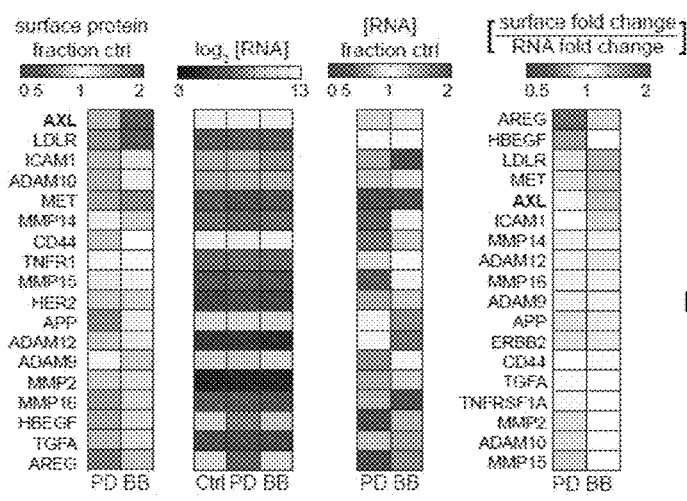

Although the biochemical pathways linking MAPK signaling to ADAM10 and ADAM17 proteolytic activities are well studied (Diaz-Rodriguez, E., et al., Extracellular signal-regulated kinase phosphorylates tumor necrosis factor alpha-converting enzyme at threonine 735: a potential role in regulated shedding. Mol Biol Cell 13, 2031-2044 (2002); Xu, P., and Derynck, R. Direct activation of TACE-mediated ectodomain shedding by p38 MAP kinase regulates EGF receptor-dependent cell proliferation. Mol Cell 37, 551-566 (2010); Xu, P., et al., TACE activation by MAPK-mediated regulation of cell surface dimerization and TIMP3 association. Sci Signal 5, ra34 (2012)), the promiscuous nature of these proteases has made it difficult to anticipate the overall effects of down-regulating their activities (Gooz 2010). Ectodomain shedding can be regulated through substrate-specific pathways, such as substrate phosphorylation (Dang et al., 2013). Accordingly, it was found that substrate-specific regulation, through differential substrate accumulation on the cell-surface, can partially be explained by transcriptional regulation (FIG. 1D; FIG. 8E). In general, however, there is substantial evidence that MEKi inhibits ADAM10 and ADAM17 catalytic activities themselves (FIG. 4A). This highlights a relatively unappreciated role for TIMP1 association in mediating this action. Consequently, MEKi essentially leads to a global reduction of ectodomain shedding across a wide range of substrates (FIG. 1A-1H). Sheddase substrates such as EGF-ligands have been studied for their role in autocrine growth factor signaling (Duffy et al., 2013). In general, AXL and MET shedding down-regulate signaling activity by limiting the accumulation of full-length, signaling-competent RTK on the cell surface. Ligand-dependent receptor activation is an important aspect of signaling activity, particularly in the context of receptor shedding (Miller, Miles Aaron. Understanding and Targeting Network-Level Sheddase Regulation in Invasive Disease. MIT, Submitted to the Department of Biological Engineering in partial fulfillment of the requirements for the degree of Doctor of Philosophy Thesis, 2013; Miller, M. A., et al. ADAM-10 and -17 regulate endometriotic cell migration via concerted ligand and receptor shedding feedback on kinase signaling. Proc Natl Acad Sci USA 110, E2074-E2083 (2013)). Nonetheless, AXL and the other RTKs exhibit significant ligand-independent activity (Meyer, A. S., et al. The receptor AXL diversifies EGFR signaling and limits the response to EGFR-targeted inhibitors in triple-negative breast cancer cells. Sci Signal 6, ra66 (2013); Zhang et al., 2012), which amplifies as they accumulate on the cell surface following protease down-regulation. Clinically, AXL up-regulation often occurs without apparent dysregulation of its ligand Gas6, and roughly half of observed AXL bypass signaling acts independently of Gas6 in drug-resistant cell lines (Zhang et al., 2012). Receptor shedding also results in the generation of inhibitory "decoy" receptors that both compete for binding of free extracellular ligand and block cell-surface dimerization between signaling-competent receptors; decoy functions have been therapeutically exploited for multiple receptors, including MET (Michieli, P., et al., Targeting the tumor and its microenvironment by a dual-function decoy Met receptor. Cancer Cell 6, 61-73 (2004)). It is shown here that kinase inhibition simultaneously increases full-length RTK on the cell surface while decreasing decoy receptor levels in extracellular supernatant or, for the case of the mouse xenograft model, in circulation. Overall, amplified signaling activity through the reduced shedding of RTKs has an unexpected prominent influence following either MPi or MEKi, and significantly attenuates drug efficacy.

Diminished RTK shedding has the potential to complement other mechanisms of bypass signaling in several regards. Many RTKs reported as transcriptionally up-regulated in response to kinase inhibition are themselves sheddase substrates, including PDGFRβ (Duncan et al., 2012; Akhavan et al., 2013), VEGFR2 (Duncan et al., 2012), and CD44 (To et al., 2010), in addition to the RTKs studied here. In the context of B-RAF and MEK inhibition, AXL repeatedly surfaces in genome-wide screens as a top candidate for rescuing drug sensitivity upon transgenic over-expression (Johannessen, C. M., et al. COT drives resistance to RAF inhibition through MAP kinase pathway reactivation. Nature 468, 968-972 (2010); Johannessen, C. M., et al. A melanocyte lineage program confers resistance to MAP kinase pathway inhibition. Nature 504, 138-142 (2013)). Reduced RTK shedding has the potential to amplify the effects of transcriptional up-regulation by increasing the fraction of total expressed RTK that remains intact on the cell surface. Within the in vivo tumor microenvironment, components such as stromal-derived growth factors and extracellular matrix contribute to bypass signaling and drug resistance (Gilbert, L. A., and Hemann, M. T. DNA damage-mediated induction of a chemoresistant niche. Cell 143, 355-366 (2010); Muranen, T., et al., Inhibition of PI3K/mTOR leads to adaptive resistance in matrix-attached cancer cells. Cancer Cell 21, 227-239 (2012); Wilson, T. R., et al., Widespread potential for growth-factor-driven resistance to anticancer kinase inhibitors. Nature 487, 505-509 (2012); Straussman, R., et al. Tumour microenvironment elicits innate resistance to RAF inhibitors through HGF secretion. Nature 487, 500-504 (2012)). Here, receptors impacted by reduced RTK shedding are also implicated in tumor-stroma ligand interactions, with a prominent example being MET activation by stromal-derived hepatocyte growth factor (HGF) (Straussman et al., 2012). Of note, extracellular HGF release does not occur through metalloproteinase ectodomain shedding. Consequently, reduced proteolytic RTK shedding shows the capacity to amplify such pro-survival tumor-stroma interactions, and previous work has demonstrated RTK shedding to be a potent modifier of ligand-dependent receptor activation (Miller et al., 2013).

Ultimately, the ability to assess RTK shedding in cancer patients using relevant biomarkers is essential for efficient clinical translation. A substantial proportion of molecular cancer diagnostics focuses on gene expression and genetic mutation. Despite the post-translational nature of receptor shedding, it is demonstrated herein that the combined signature of multiple gene expression levels predicts MEK sensitivity and synergistic response to combination MEK and AXL inhibitors. As previously discussed, gene expression often fails to accurately describe signaling network activities. Here, RTK proteolysis is a mechanistic explanation for the discordance between gene expression and signaling activity, and provides evidence that receptor shedding can be non-invasively monitored in clinical samples following drug treatment. Ultimately, circulating RTKs hold the potential to complement other diagnostic biomarkers in guiding targeted combination therapies, monitoring drug response, and non-invasively detecting bypass signaling pathways that indicate drug resistance.

Compositions and Methods of Use for the Treatment of Cancer:

In one embodiment, the present invention relates to a method of treating a cancer in an individual comprising administering a therapeutically effective amount of a combination of inhibitors, such as a kinase inhibitor, e.g., a RTK inhibitor described herein, such as a mitogen activated protein kinase (MAPK) inhibitor (MAPKi), an AXL kinase inhibitor (AXLi), a Met inhibitor, and a PI3K inhibitor (PI3Ki), to the individual. In one aspect, the method comprises administering a therapeutically effective amount of a MAPKi and an AXLi. In yet another aspect, the method comprises administering a therapeutically effective amount of a MAPKi and a Met inhibitor. In yet another aspect, the method comprises administering a therapeutically effective amount of a MAPKi and a PI3Ki. In yet another aspect, the method comprises administering a therapeutically effective amount of a AXLi and a PI3Ki.

An "inhibitor" of the present invention comprises any composition that modulates a chemical, biochemical, or biological process by inhibiting, reducing, etc. directly or indirectly. Specific inhibitors are provided herein. For example, as used herein, a "MAPK inhibitor" or "MAPKi" can be any composition (e.g., compound, drug, antibody, biologic, small molecule, etc.) that inhibits or reduces the action or activity of one or more mitogen activated protein kinases. As will be appreciated by one of skill in the art, MAP kinases (MAPK) are also known as extracellular signal-regulated kinases (ERK). The MAPK/ERK pathway relates to the chain of proteins in a cell that communicates a signal from a cell surface receptor to nucleic acid in the nucleus of the cell.

Examples of MAPK inhibitors are BRAF inhibitors, MEK1 inhibitors and/or MEK2 inhibitors. Other specific examples of MAPK inhibitors include, but are not limited to, U0216, PD32901, AZD6244 (selumetinib), sorafenib, trametinib (GSK1120212), and vemurafenib.

As used herein, "AXL inhibitor" and "AXL kinase inhibitor" are used interchangeably. Examples of AXL inhibitors inhibitors include, but are not limited to, R428, MP-470 (amuvatinib), and XL-880 (foretinib).

As used herein, "PI3K inhibitor" refers to any composition that inhibits Phosphatidylinositol-4,5-bisphosphate 3-kinase. One example of a PI3K inhibitor is BAY 80-9646 (Copanlisib). Another is 294002.

It will be appreciated by one of skill in the art, one or more additional therapeutic agents (e.g., chemotherapeutics, antineoplastics, etc.) can be used in the methods described herein. In one aspect, an additional therapeutic agent is a metalloproteinase inhibitor (MPi). One example of a MPi is BB94.

In one aspect, the invention is directed to a method of reducing resistance to one of the inhibitors described herein (e.g., a MAPK inhibitor such as a MEK inhibitor), comprising administering to an individual being treated with the inhibitor (e.g., the MAPK inhibitor), a therapeutically effective amount of a second inhibitor (e.g., an AXL inhibitor).

One of skill in the art will appreciate that drug resistance can occur in some individuals and not others.

In another aspect, the invention is directed to a method of increasing (e.g., reducing attenuation of) efficacy of an inhibitor described herein, such as a MAPK inhibitor (e.g., a MEK inhibitor), comprising administering to an individual being treated with a MAPK inhibitor, a therapeutically effective amount of an AXL inhibitor.

Sheddase and Sheddase Substrates:

In one embodiment, the present invention relates to a method of treating a cancer in an individual comprising administering an inhibitor reduce shedding of one or more sheddase substrates, thereby reducing a level of the one or more sheddase substrates in the individual's circulation, and an AXL inhibitor. The inhibitor can be a MAPK inhibitor. In some aspects, the sheddase is A Disintegrin and Metalloproteinase (ADAM). In one aspect, the ADAM is ADAM10 and/or ADAM17.

In one aspect, the sheddase substrate is a receptor tyrosine kinase (RTK), a cytokine receptor, a growth factor ligand, or a combination thereof. In some aspects, the RTK is selected from the group consisting of Met, HER2, HER4, and AXL. In another aspect, the cytokine receptor is Tumor Necrosis Factor Receptor 1 (TNFR1). In another aspect, the growth factor ligand is selected from the group consisting of AREG, HBEGF, and TGFα. In some aspects, the sheddase substrate is a RTK of the TAM family, including AXL, Tyro3, MerTK, or a combination thereof.

In one aspect, the inhibitor (e.g., a MAP inhibitor, e.g., MEKi) reduces shedding of one or more sheddase substrates, thereby decreasing a level of the one or more sheddase substrates in the individual's circulation; and an increased level of one or more sheddase substrates indicates a positive treatment response to the MAPK inhibitor and the AXL inhibitor.

In one aspect, the inhibitor (e.g., a MAP inhibitor, e.g., MEKi) reduces shedding of one or more sheddase substrates, thereby decreasing a level of the one or more sheddase substrates in the individual's circulation; and a decreased level of one or more sheddase substrates indicates a positive treatment response to the MAPK inhibitor and the AXL inhibitor.

Cancer:

The present invention also provides a method for modulating or treating at least one malignant disease in a cell, tissue, organ, or individual (animal or human). In some embodiments, the inhibitor compounds and compositions of the present invention are used to treat or prevent cancer. Cancer can include any malignant or benign tumor of any organ or body system. Examples include, but are not limited to, the following: breast, digestive/gastrointestinal, endocrine, neuroendocrine, eye, genitourinary, germ cell, gynecologic, head and neck, hematologic/blood, musculoskeletal, neurologic, respiratory/thoracic, bladder, colon, rectal, lung, endometrial, kidney, pancreatic, liver, stomach, testicular, esophageal, prostate, brain, cervical, ovarian and thyroid cancers. In some aspects, the cancer is a carcinoma, sarcoma, lymphoma, leukemia, or blastoma. In some aspects, the carcinoma is a breast cancer, a melanoma, a lung cancer or an ovarian cancer. In one aspect, the breast cancer expresses low estrogen receptor, progesterone receptor, HER2, or a combination thereof (e.g., triple-negative breast cancer, or TNBC). In another aspect, the blastoma is glioblastoma multiforme. Other cancers can include leukemias, melanomas, and lymphomas, and any cancer described herein or known to one of skill in the arts. In some embodiments, the solid tumor is infiltrated with myeloid and/or T-cells. In some embodiments, the cancer is a leukemia, lymphoma, myelodysplastic syndrome and/or myeloma. In some embodiments, the cancer can be any kind or type of leukemia, including a lymphocytic leukemia or a myelogenous leukemia, e.g., acute lymphoblastic leukemia (ALL), chronic lymphocytic leukemia (CLL), acute myeloid (myelogenous) leukemia (AML), chronic myelogenous leukemia; hairy cell leukemia, T-cell prolymphocytic leukemia, large granular lymphocytic leukemia, adult T-cell leukemia, acute leukemia, B-cell, T-cell or FAB ALL, chronic myelocytic leukemia (CML), myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer-related bone pain, and the like.

In some embodiments, the lymphoma is a histocytic lymphoma, and in some embodiments, the cancer is a multiple myeloma. In some embodiments, the cancer is a solid tumor, for example, a melanoma, or bladder. acute leukemia, B-cell, T-cell or FAB ALL, chronic myelocytic leukemia (CML), myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer-related bone pain, and the like.

Treatment

In one aspect of the methods described herein, administering the combination of inhibitors, such as a MAPK inhibitor and AXL inhibitor, reduces tumor growth or size in the individual. In another aspect, such administration reduces metastasis in the individual.

In one aspect, the invention is directed to a method of modulating a tumor in an individual comprising administering a combination of inhibitors described herein, such as a MAPK inhibitor and an AXL inhibitor to the individual.

"Modulate" is used consistently with its use in the art, i.e., meaning to cause or facilitate a qualitative or quantitative change, alteration, or modification. Without limitation, such change may be an increase, decrease, or change in relative strength or activity. A "modulator" is an agent that causes or facilitates a qualitative or quantitative change, alteration, or modification in a process, pathway, or phenomenon of interest. An "inhibitor" inhibits, for example, decreases, diminishes or arrests, the activity or effect of that which it inhibits.

In some aspects, the inhibitors and therapies described herein are co-administered with an additional therapeutic agent.

In some aspects, the inhibitors and therapies described herein are co-administered with a vaccine (such as a viral vector vaccine, bacterial vaccine, cell-based vaccine, DNA vaccine, RNA vaccine, peptide vaccine, or protein vaccine). Such vaccines are well known in the art. See, e.g., Jeffrey Schlom, "Therapeutic Cancer Vaccines: Current Status and Moving Forward," *J Natl Cancer Inst;* 104:599-613 (2012), the contents of which are incorporated herein in their entirety.

In some aspects, the inhibitors and therapies described herein are co-administered with agents for chemotherapy, hormone therapies, biological therapies, and/or bisphosphonates. In some embodiments, the agent(s) for chemotherapy include one or more of the following: arboplatin (Paraplatin) cisplatin (Platinol, Platinol-AQ) cyclophosphamide (Cytoxan, Neosar) doxorubicin (Adriamycin) etoposide (VePesid) fluorouracil (5-FU) gemcitabine (Gemzar) irinotecan (Camptosar) paclitaxel (Taxol) topotecan (Hycamtin) vincristine (Oncovin, Vincasar PFS) vinblastine (Velban).

The inhibitors (e.g., a MAPK inhibitor, an AXL inhibitor, a Met inhibitor, or a combination thereof or any other inhibitor described herein) and compositions of the invention described herein may be administered to an individual in need thereof to prevent (including preventing the recurrence of cancer) or treat (e.g., manage or ameliorate a cancer or one or more symptoms thereof) cancer. Any agent or therapy (e.g., chemotherapies, radiation therapies, hormonal therapies, and/or biological therapies or immunotherapies) which is known to be useful, or which has been used or is currently being used for the prevention, treatment, management or amelioration of cancer or one or more symptoms thereof can be used in combination with one or more inhibitor compounds or compositions of the invention described herein. Examples of other anti-cancer agents include: 5-fluoruracil; acivicin; aldesleukin; altretamine; aminoglutethimide; amsacrine; anastrozole; anthramycin; asparaginase; azacitidine; azetepa; azotomycin; batimastat; bicalutamide; bleomycin sulfate; brequinar sodium; bropirimine; busulfan; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; enloplatin; enpromate; epipropidine; epirubicin hydrochloride; erbulozole; esorubicin hydrochloride; estramustine; estramustine phosphate sodium; etanidazole; etoposide; etoposide phosphate; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-m; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; mechlorethamine hydrochloride; megestrol acetate; melengestrol acetate; melphalan; menogaril; mercaptopurine; methotrexate; methotrexate sodium; metoprine; meturedepa; mitomycin; mitosper; mitotane; mitoxantrone hydrochloride; mycophenolic acid; nocodazole; ormaplatin; paclitaxel; pegaspargase; porfromycin; prednimustine; procarbazine hydrochloride; puromycin; rogletimide; safingol hydrochloride; semustine; simtrazene; sparfosate sodium; sparsomycin; spiromustine; spiroplatin; streptonigrin; streptozocin; sulofenur; talisomycin; tegafur; teloxantrone hydrochloride; temoporfin; teniposide; teroxirone; testolactone; thiamiprine; thioguanine; thiotepa; tiazofurin; tirapazamine; topotecan; trimetrexate; trimetrexate glucuronate; triptorelin; uracil mustard; uredepa; vapreotide; verteporfn; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. The invention also encompasses administration of a MAPK inhibitor, an AXL inhibitor, a Met inhibitor, or a combination thereof of the invention in combination with other cancer treatments, including radiation therapy comprising the use of x-rays, gamma rays and other sources of radiation to destroy the cancer cells. Cancer treatments are known in the art and have been described in such literature as the *Physician's Desk Reference* (57th ed., 2003).

Administration:

The present invention also relates to a method of treating a cancer in an individual, wherein a combination of inhibitors, e.g., a MAPK inhibitor, a AXL inhibitor, ad/or n Met inhibitor, are administered to the individual at or near the same time. In one aspect, they are administered at different times, e.g., a MAPK inhibitor is administered before or after administration of an AXL inhibitor to the individual.

In one aspect the individual is an organism. In another aspect, the organism is a mammal. In another aspect, the mammal is a human or a non-human primate. In another aspect, the mammal is a canine or feline.

In some aspects, the MAPK inhibitor and the AXL inhibitor are administered to the individual in a single formulation. In another aspect, the MAPK inhibitor and the AXL inhibitor are administered to the individual in different formulations.

In some aspects of the methods described herein, the amount of the MAPK inhibitor, AXL inhibitor, or both is adjusted after monitoring a level of at least one (e.g., one or more) sheddase substrate in the individual's circulation. In a particular aspect, the amount of AXL inhibitor administered is increased if the serum level of a sheddase substrate is higher than normal. In another aspect, the AXL inhibitor is administered after the individual's serum levels of sheddase substrate are determined to be higher than normal.

The inhibitors of the invention (e.g., MAPK inhibitors, AXL inhibitors, Met inhibitors, PI3K inhibitors, MP inhibitors) can be administered as part of a combination therapy (e.g., with each other, or with one or more other therapeutic agents). The one or more inhibitor compounds of the invention can be administered before, after or concurrently with one or more other therapeutic agents. In some embodiments, one or more inhibitor compounds of the invention and other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). An (one or more) inhibitor compound of the invention and one or more other therapeutic agents can be administered in a single dose or in multiple doses, in an order and on a schedule suitable to achieve a desired therapeutic effect. Suitable dosages and regimens of administration can be determined by a clinician and are dependent on the agent(s) chosen, pharmaceutical formulation and route of administration, various patient factors and other considerations.

The inhibitors described herein can be used at doses appropriate for conditions for they are known to be useful. The typical daily dose of the active substance varies within a wide range and will depend on various factors, such as, the individual requirement of each individual and the route of administration. The term "mg/kg," as used herein means "mg" of inhibitor per "kg" of body weight of the individual.

One of skill in the art, e.g., a clinician, can determine the suitable dosage and route of administration for a particular inhibitor or composition for administration to an individual, considering the agents chosen, pharmaceutical formulation and route of administration, various clinical or patient factors (such as, but not limited to, age, weight, health, etc.) and other considerations (e.g., tumor size, presence of metastasis, stage, type of cancer, etc.). Preferably, the dosage is therapeutically effective and does not cause or produces minimal or no adverse side effects. In standard multi-dosing regimens, a pharmacological agent may be administered on a dosage schedule that is designed to maintain a predetermined or optimal plasma concentration in the subject undergoing treatment. The pharmaceutical composition can be in unit dosage form. In such form, the composition is subdivided into unit doses containing appropriate quantities of the active ingredient.

The inhibitors and compositions can be added at any appropriate dosage ranges or therapeutically effective amount, for example, 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 30 mg/kg, 40 mg/kg, 50 mg/kg 60 mg/kg, 70 mg/kg, 80 mg/kg, 90 mg/kg and 100 mg/kg.

In one aspect, the dosage of each administered composition or inhibitor (e.g., MAPK inhibitor, AXL inhibitor, Met inhibitor, PI3K inhibitor and MP inhibitor) is 0.1-100 mg/kg per administration. In another aspect, the therapeutically effective amount of each administered inhibitor comprises from about 1 to about 300 mg/kg per administration. In another aspect, the therapeutically effective amount of each administered inhibitor comprises from about 1 mg to about 3000 mg per administration.

One of skill in the art will appreciate that dosages of certain compositions or inhibitors can be found in a variety of sources, such as http://clinicaltrials.gov or http://www-.cancer.gov/drugdictionary.

In one aspect, PD325901 can be administered in arrange from 1 mg once a day to 30 mg twice daily. In one aspect, it can be administered up to 30 mg twice daily (BID), for example the dose can be (e.g., 0.1 mg BID, 0.5 mg BID, 0.75 mg BID, 1 mg BID, 2 mg BID, 3 mg BID, 4 mg BID, 5 mg BID, 10 mg BID, 15 mg BID, 20 mg BID, 25 mg BID, and 30 mg BID). In one aspect, it is administered in a dose of less than 10 mg BID.

In one aspect, R428 (BGB324) can be administered up to 1.5 g/day (e.g., 1 mg, 10 mg, 20 mg, 30 mg, 40 mg, 50 mg, 75 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, and 1500 mg per day).

In one aspect, Foretinib (also known as GSK1363089 or XL880) can be administered up to 80 mg per day (e.g., 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, and 80 mg). In another embodiment, it is administered at a dose of approximately 240 mg on a 5 day on/9 day off schedule every fourteen days.

In one aspect, Amuvatinib (MP-470) can be administered up to approximately 1,500 mg/day (e.g., 1 mg, 10 mg, 20 mg, 30 mg, 40 mg, 50 mg, 75 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, and 1500 mg per day), given as one (e.g., QD) or in divided doses (e.g., BID, TID, or QID). Examples of divided doses include 1 mg twice daily (BID), 10 mg BID, 20 mg BID, 30 mg BID, 40 mg BID, 50 mg BID, 75 mg BID, 100 mg BID, 200 mg BID, 300 mg BID, 400 mg BID, 500 mg BID, 600 mg BID, 700 mg BID, and 750 mg BID. In one example, it is given for 1-6 cycles.

In one aspect, Trametinib can be administered up to 2 mg/day (e.g., 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, and 2.0 mg per day). In one aspect, it is administered in combination with dabrafenib, e.g., Trametinib 2 mg once daily and dabrafenib 150 mg twice daily.

In one aspect, Selumetinib can be administered up to 75 mg twice daily (BID) (e.g, 1 mg BID, 5 mg BID, 10 mg BID, 20 mg BID, 25 mg BID, 30 mg BID, 40 mg BID, 50 mg BID, 60 mg BID, 70 mg BID, and 75 mg BID).

In one aspect, Vemurafenib can be administered up to 1000 mg twice daily (e.g., 1 mg, 10 mg, 20 mg, 30 mg, 40 mg, 50 mg, 75 mg, 100 mg, 200 mg, 300 mg, 400 mg, 500 mg, 600 mg, 700 mg, 800 mg, 900 mg, and 1000 mg twice daily). In some embodiments, it is given at a dose of 960 mg, 720 mg or 480 mg, e.g., twice daily.

In one aspect, Sorafenib (Nexavar) can be administered up to 400 mg (e.g., 1 mg, 10 mg, 20 mg, 30 mg, 40 mg, 50 mg, 75 mg, 100 mg, 200 mg, 300 mg, and 400 mg) twice daily. For example, the dose can be divided into two smaller doses that add up to 400 mg per day (e.g., 2×200 mg tabs PO QD).

In one aspect, Copanlisib (BAY80-6946) can be administered as a 1 hour intravenous (IV) infusion weekly (days 1, 8 and 15 on a 28-day cycle). In one aspect, a starting dose can comprise about 0.8 mg/kg (maximum dose of 65 mg), and this dose can be reduced to 0.6 mg/kg (maximum dose of 48 mg), to 0.4 mg/kg (maximum dose of 32.5 mg), to 0.2 mg/kg (maximum dose 16 mg), or combinations thereof.

In certain embodiments, the method comprises administering each of the inhibitors (e.g., MAPK inhibitor, AXL inhibitor, Met inhibitor, PI3K inhibitor, MP inhibitor) or combinations thereof once, at least once, twice, at least twice, three times, at least three times, four times, or at least four times per day. In one embodiment, the method comprises administering each of the MAPK inhibitor, AXL inhibitor, Met inhibitor, PI3K inhibitor, MPi, or combinations thereof at least once per day. In another embodiment, the method comprises administering each of the MAPK inhibitor, AXL inhibitor, Met inhibitor, PI3K inhibitor, MPi, or combinations thereof at least twice per day. In another embodiment, the method comprises administering the inhibitors at least three times per day. In another embodiment, the method comprises administering each of the MAPK inhibitor, AXL inhibitor, Met inhibitor, PI3K inhibitor, MPi, or combinations thereof at least four times per day.

In another embodiment, the method comprises administering each of the MAPK inhibitor, AXL inhibitor, Met inhibitor, PI3K inhibitor, MPi, or combinations thereof as many times as is necessary to treat a cancer. In this instance, the dosage of each of the MAPK inhibitor, AXL inhibitor, Met inhibitor, PI3K inhibitor, MPi, or combinations thereof can be specifically tailored to a specific individual and can vary from dose to dose and from day to day. One of skill in the art would readily appreciate the dosing variability of each of the inhibitors to treat a cancer.

In one aspect, the inhibitors of the invention can be present in the form of pharmaceutically acceptable compositions. In another embodiment, the inhibitors of the invention can be present in the form of pharmaceutically acceptable salts. For use in medicines, the salts of the inhibitors of the invention refer to non-toxic pharmaceutically acceptable salts. The pharmaceutically acceptable salts of the inhibitors include acid addition salts and base addition salts. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the inhibitors described herein can be prepared from an inorganic acid or an organic acid.

The pharmaceutical compositions disclosed herein can be prepared in accordance with standard procedures and are administered at dosages that are selected to reduce, prevent, or eliminate, or to slow or halt the progression of, the condition being treated (See, e.g., Remington's Pharmaceutical Sciences, Mack Publishing Company, Easton, Pa., and Goodman and Gilman's The Pharmaceutical Basis of Therapeutics, McGraw-Hill, New York, N.Y., the contents of which are incorporated herein by reference in their entirety, for a general description of the methods for administering various agents for human therapy). The compositions of a compound represented by the disclosed inhibitors can be delivered using controlled or sustained-release delivery systems (e.g., capsules, biodegradable matrices). Exemplary delayed-release delivery systems for drug delivery that would be suitable for administration of the compositions of the disclosed compounds are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni), the entire teachings of which are incorporated herein by reference.

Compositions, such as pharmaceutical compositions, are encompassed within the present invention. For preparing pharmaceutical compositions comprising the inhibitors of the present invention, pharmaceutically acceptable carriers can be, for example, solid, semi-solid or liquid. Solid preparations include, but are not limited to, powders, tablets, pills, capsules, cachets, suppositories, and dispersible granules. For example, the compounds (e g, inhibitors) of the present invention can be in powder form for reconstitution at the time of delivery. A solid carrier can be, for example, one or more substances which can also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration. For therapeutic purposes, the tablets and capsules can contain, in addition to the active ingredient, conventional carriers.

Liquid preparations include solutions, suspensions, retention enemas, and emulsions, for example, water or water propylene glycol solutions. For parenteral injection, liquid preparations can be formulated in solution in aqueous polyethylene glycol solution. Oral liquid preparations generally in the form of aqueous or oily solutions, suspensions, emulsions, syrups or elixirs can contain conventional additives such as suspending agents, emulsifying agents, non-aqueous agents, preservatives, coloring agents and flavoring agents. Aqueous solutions suitable for oral administration can be prepared by dissolving the active ingredient in water and adding suitable colorants, flavors, stabilizing agents, and thickening agents as desired.

The inhibitor compounds and compositions can, for example, be administered parenterally, nonparenterally, intravascularly, intravenously, intramuscularly, subcutaneously, intraperitoneally, transmucosally, intrathecally, nasally, sublingually, transdermally, orally or topically. One of ordinary skill in the art will recognize that the following dosage forms can comprise as the active ingredient, either compounds or a corresponding pharmaceutically acceptable salt of a compound of the present invention. One embodiment of the invention is oral administration of the compounds.

Diagnostics and Kits

Also encompassed within the scope of the invention are methods of determining whether a person is, or could become, resistant to an inhibitor such as a MAPK inhibitor, comprising determining the levels of circulating sheddase substrates in an individual after administration of the inhibitor. Also encompassed a methods of adjusting the amounts of bypass pathway inhibitors, such as AXL inhibitor, to administer to a patient following monitoring the individual's circulating sheddase substrate levels after administration of an inhibitor.

Kits to perform the claimed methods are also encompassed in the invention. In some aspects, the kits comprise one or more inhibitors or compounds (e.g., composition, and formulation).

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments described herein, which fall within the scope of the claims. The scope of the present invention is not to be limited by or to embodiments or examples described above.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

Embodiments in which any one or more limitations, elements, clauses, descriptive terms, etc., of any claim (or relevant description from elsewhere in the specification) is introduced into another claim are provided. For example, a claim that is dependent on another claim may be modified to include one or more elements or limitations found in any other claim that is dependent on the same base claim. It is expressly contemplated that any amendment to a genus or generic claim may be applied to any species of the genus or any species claim that incorporates or depends on the generic claim.

Where a claim recites a method, a composition for performing the method is provided. Where elements are presented as lists or groups, each subgroup is also disclosed. It should also be understood that, in general, where embodiments or aspects is/are referred to herein as comprising particular element(s), feature(s), agent(s), substance(s), step(s), etc., (or combinations thereof), certain embodiments or aspects may consist of, or consist essentially of, such element(s), feature(s), agent(s), substance(s), step(s), etc. (or combinations thereof). It should also be understood that, unless clearly indicated to the contrary, in any methods claimed herein that include more than one step or act, the order of the steps or acts of the method is not necessarily limited to the order in which the steps or acts of the method are recited. Any method of treatment may comprise a step of providing a subject in need of such treatment, e.g., a subject having a disease for which such treatment is warranted. Any method of treatment may comprise a step of diagnosing a subject as being in need of such treatment, e.g., diagnosing a subject as having a disease for which such treatment is warranted.

Where ranges are given herein, embodiments in which the endpoints are included, embodiments in which both endpoints are excluded, and embodiments in which one endpoint is included and the other is excluded, are provided. It should be assumed that both endpoints are included unless indicated otherwise. Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated.

EXEMPLIFICATION

Materials and Methods

Unless otherwise stated, reported replicates are from unique biological samples, statistical tests used the two-sided student's t-test for significance, and mean values are reported with error bars denoting standard error of the mean. With some explicitly stated exceptions, experiments used 10 µM BB94, 3 µM R428, 3 µM PD325901, 5 µM U0126, 10 µM AZD6244, 15 µM MP470, and 4 µM pro-ADAM-10.

Cell Lines, Inhibitors, Antibodies, and siRNA

Cell lines were obtained from the ATCC, with exceptions as follows: SUM102, SUM149, SUM159, and SUM1315 were from Asterand (Detroit, Mich.); MA2 and LM2 cells were provided by Prof. Richard Hynes (Massachusetts Institute of Technology, Cambridge, Mass.) and Prof. Joan Massague (Memorial Sloan Kettering, New York, N.Y.), respectively. Gefitinib-resistant HCC827 cells (HCC827-GR) were produced as described (Turke et al., 2010). All cells were grown according to vendor guidelines.

The following inhibitors were used in FIG. 1H, at the following concentrations: metalloproteinase inhibitor BB94 (10 µM; Tocris Bioscience), p38 inhibitor SB203580 (20 µM; Selleck Chem), MEK1/2 inhibitor PD0325901 (10 µM; LC Labs), Met/AXL inhibitor XL-880 (5 µM; Selleck Chem), MEK1/2 inhibitor U0126 (10 µM; Selleck Chem), MEK1/2 inhibitor AZD6244 (10 µM; Selleck Chem), Aurora kinase inhibitor VX-680 (10 µM; Selleck Chem), PI3K inhibitor LY294002 (10 µM; Selleck Chem), JNK1/2 inhibitor JNK-IN-8 (3 µM; courtesy Nathaniel Gray, Harvard Medical School), JNK inhibitor SP600125 (10 µM; LC Labs), EGFR inhibitor gefitinib (1 µM; LC Labs), EGFR inhibitor erlotinib (1 µM; LC Labs), JNK inhibitor TCS-6o (1 µM; Tocris Bioscience), Abl inhibitor imatinib (1 µM; LC Labs), EGFR/HER2 inhibitor lapatinib (1 µM; LC Labs), AXL inhibitor R428 (3 µM; Selleck Chem), Alk5 inhibitor ALX-270-448 (5 µM; Enzo life sciences), AXL/MET inhibitor MP470 (5 µM; Selleck Chem), myosin light chain kinase inhibitor ML7 (1 µM; Sigma), and glycogen synthase kinase 3b inhibitor SB216763 (10 µM; Selleck Chem) Inhibitor concentrations were chosen based roughly on exceeding previously published Ki and $IC_{50}$ values. The ADAM-10 inhibitor pro-ADAM-10 was from Biozyme, Inc. (St. Joseph, Mo.) and was used at 4 µM.

AXL, MET, TNFR1, and EGF-ligand supernatant measurements were performed using duo-set ELISA kits (R&D Systems, Minneapolis, Minn.). Total RTK measurements for HER2 and HER4 were performed using bead-based immunoassays (EMD Millipore, Billerica, Mass.). Phospho-protein measurements were performed using bead-based immunoassays (Bio-Rad, Hercules, Calif.) for ERK1/2 ($pThr^{185}$/$pTyr^{187}$, $pThr^{202}$/$pTyr^{204}$), GSK3 (GSK3α/β $pSer^{21}$/$pSer^9$), JNK ($pThr^{183}$/$pTyr^{185}$), p38 ($pThr^{180}$/$pTyr^{182}$), cJun ($pSer^{63}$), STAT3 ($pTyr^{705}$), Akt ($pSer^{473}$), NFkB (p65 $pSer^{536}$), and p70S6 ($pThr^{421}$/$pSer^{363}$).

pTyr-RTK measurements used bead-based immunocapture with a pan-pTyr detection antibody (EMD Millipore, Billerica, Mass.). Unless otherwise stated, immunoassays followed manufacturer protocols. Bead-based immunoassays were routinely normalized according to the micro BCA protein assay (Pierce) or cell count (ViCell). ADAM17 ($pThr^{735}$) and ADAM10 western blot Abs were from Sigma. Anti-phospho Histone H3 (Ser10) for measuring mitotic index was from EMD Millipore, (Billerica, Mass.). GAPDH (glyceraldehyde-3-phosphate dehydrogenase) and α-actinin were used for Western blotting and purchased from Cell Signaling Technology (Danvers, Mass.). APP Ab was from Abcam (Cambridge, Mass.). Live-cell immunostaining was performed using R&D Systems (Minneapolis, Minn.) Abs. SiRNAs, including non-targeting control siRNA, were packaged as SMARTpool ON-TARGETplus and used with DharmaFECT4 (Thermo Scientific, Tewksbury, Mass.). For ADAM10/17 western blots, lysis was performed with 50 mM tris-HCl (pH 7.5), 10% glycerol, 150 mM NaCl, and 1% NP-40, with complete protease (Roche, Nutley, N.J.) and phosphatase (Boston BioProducts, Ashland, Mass.) inhibitors added immediately before use.

Supernatant Analysis

For quantification of supernatant protein levels, cell supernatant was collected at the indicated time-point, spun for 5 min at 300 g, and frozen at −80° C. for future use. Supernatants were routinely normalized to cell count, determined via trypsinization and ViCell (Beckman Coulter, Brea, Calif.), and volumes were kept consistent across treatments.

Antibody Microarray Analysis

MDA-MB231 cells were plated in 10 cm plates at 70% confluency, treated the following day with either DMSO or PD325901, and supernatant was collected 24 hours (h) later. Using L-1000 RayBio (Norcross Ga.) microarrays, supernatant was processed according to manufacturer instructions. Two biological replicate samples were analyzed for the control and MEKi conditions, with one sample undiluted and the other diluted 1:5 in growth media. Each array contains duplicate antibody spots, and so a total of n=4 replicates was used to determine significant changes in supernatant proteins. Only proteins measured more than four standard deviations above background for at least one condition were included in the analysis. Gene set enrichment analysis was performed as previously described using gene ontology (GO) gene sets (Subramanian, A. et al., Gene set enrichment analysis: a knowledge-based approach for interpreting genome-wide expression profiles. Proc Natl Acad Sci USA 102, 15545-15550 (2005)). The transmembrane receptor activity gene set, comprising 13 proteins, exhibited the highest enrichment score for control-treated cells, with a corresponding p-value of 0.06. The other top gene-sets were "intrinsic to membrane", "integral to membrane", "receptor activity", and "intrinsic to plasma membrane". The highest enrichment score in PD325901-treated cells was for "hematopoietin interferon class-D200 domain cytokine receptor binding" comprising 10 non-transmembrane proteins, with a corresponding p-value of 0.003.

RNA Microarray Analysis

MDA-MB231 cells were plated in 10 cm plates at 70% confluency, treated the following day with either DMSO control, BB94, or PD325901, and lysed 24 h later. RNA was prepared using the Qiagen RNeasy Mini kit, and samples were analyzed using Agilent Primeview arrays. Control and inhibitor treatments had n=4 and n=3 biological replicates, respectively. Data were preprocessed using the R/Bioconductor package "affy" and the RMA normalization routine. One BB94 replicate was excluded as an outlier, as determined using the arrayQualityMetrics function. Differentially expressed genes were determined by student's t-test and as falling below a Storey false-discovery-rate[26] of 0.05. Gene set enrichment analysis was performed as previously described using gene ontology (GO) gene sets (Subramanian, A., et al., Gene set enrichment analysis: a knowledge-based approach for interpreting genome-wide expression profiles. Proc Natl Acad Sci USA 102, 15545-15550 (2005)).

Live-cell Immunostaining

Cells were trypsinized, rinsed in 4° C. phospho-buffered saline (PBS)+3% FBS, incubated with 1° Ab (i.e., primary antibody) in PBS+3% FBS for 1 h, rinsed, and fixed overnight in PBS+1% formaldehyde at 4° C. The following day, cells were rinsed, incubated with 2° Ab (i.e., secondary antibody) conjugated to either Alexa647 or Alexa546, rinsed, and analyzed by flow cytometry. Fold-change was determined after subtracting the median fluorescence from control cells stained with the IgG control antibody.

RTK Cross-linking

MDA-MB231 cells were plated at 90% confluency on three 10-cm plates for each condition, serum starved for 4 h the following day, and treated with inhibitor in serum-free media for 2 h. Cells were then cross-linked with 1 mM EGS for 30 min at 4° C., lysed. Receptor cross-linking was measured using a modified MET and HER2 Luminex Bioplex assay, as previously described (Meyer, A. S., Miller, M. A., Gertler, F. B., and Lauffenburger, D. A. (2013). The receptor AXL diversifies EGFR signaling and limits the response to EGFR-targeted inhibitors in triple-negative breast cancer cells. Sci Signal 6, ra66).

Clinical Serum Sample Analysis

Serum samples from healthy control individuals and stage IV breast cancer patients were purchased from Bioreclamation (Long Island, N.Y.). Samples were analyzed using bead-based immunoassay (for MET, HER2, HER4, and AXL) and ELISA (for AXL). AXL measurements were averaged between the two assay formats. For each analyte, measurement values were divided by the averaged FLU measurement across all samples and then log-transformed. Statistical significance was calculated by two-tailed Student's t-test for all metrics, including double-, triple-, and quadruple-positive calculations.

siRNA Knockdown Protocol

For all siRNA treatments, 500,000 cells were seeded in 10 cm dishes, transfected using 5 µL Dharmafect4 and 125 pmol siRNA, reseeded for knockdown experiments 24 h later, and 48 h after transfection cells were treated and lysed.

Short Term p-AXL Up-regulation

As shown in FIG. 1F, MDA-MB231 cells were plated at 90% confluency on 10 cm plates, serum starved for 4 h the following day, treated with inhibitor in serum-free media for 2 h, lysed, and analyzed by bead-based immunoassay.

Short Term BB94-elicited Downstream Phosphosignaling

Figure 2B:
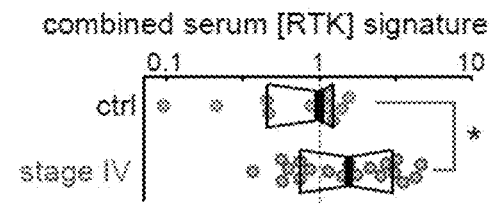
Figure 2C:
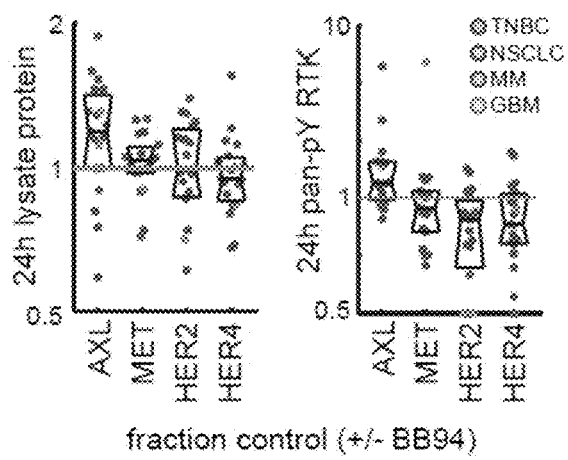
Figure 2D:
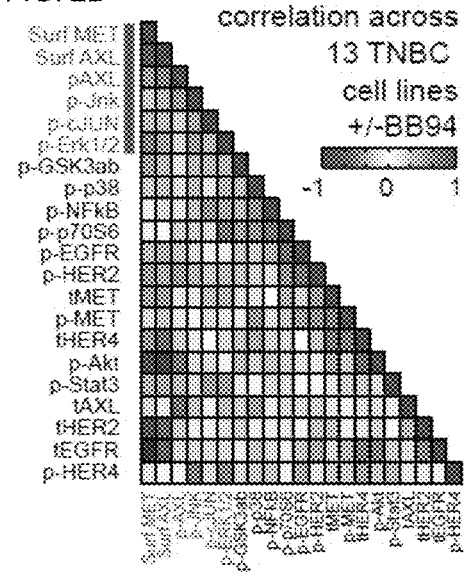
Figure 2E:
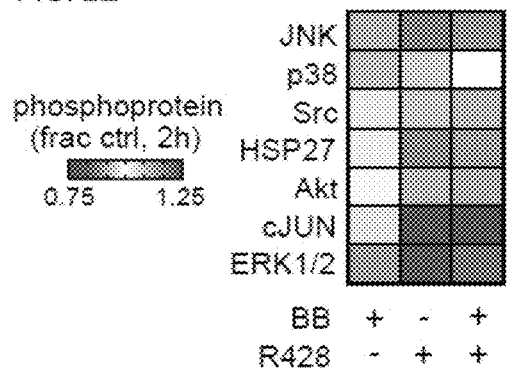

As shown in FIG. 2E, MDA-MB231 cells were plated at 90% confluency in 96-well plates, serum starved for 4 h the following day, treated with BB94, R428, or dual BB94/R428 for 2 h, and then lysed and analyzed by bead-based immunoassay. For siRNA experiments (FIG. 2F), cells were treated with siRNA as described above and seeded in 96-well plates at equal 90% confluency. 48 h post-transfection, cells were serum starved for 4 h, treated with inhibitor for 3 h, then lysed and analyzed by bead-based immunoassay.

AXL Measurements Following siRNA and ADAM10 Inhibitor Treatments

Figure 3A:
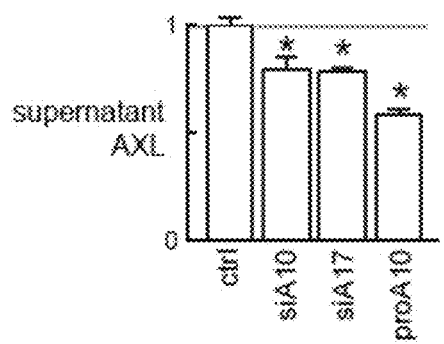
FIG. 3A-3F illustrates that AXL shedding by ADAM10 and ADAM17 affects its cell-surface levels and cell proliferation.
Figure 3B:
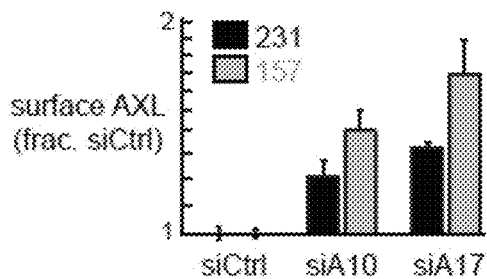

As shown in FIG. 3A-3B, MDA-MB231 cells were treated with siRNA as described above and were seeded in 96-well plates at equal 90% confluency. Media was changed at 48 h post-transfection, and 24 h later supernatant was collected and cells were analyzed by live-cell immunostaining. For proADAM10 treatment, cells were seeded in 96-well plates at 90% confluency, treated with inhibitor or buffer control the following day, and supernatant was collected 24 h later.

Multivariate Correlation Analysis

For correlation analysis following BB94 treatment (FIG. 2D), 13 cell lines were plated at 70% confluency, and treated the following day with BB94. 24 h later cells were counted and analyzed by live-cell immunostaining or bead-based immunoassay. Pairwise correlation was calculated between fold-change measurements as they varied across the 13 cell lines. Both Spearman and Pearson correlations were determined from mean-centered and variance-normalized data, with the more significant of the two correlations reported.

ADAM17 Dimerization

For each condition, two confluent 15 cm plates of cells were serum-starved for 4 h, treated with inhibitor for 3 h, rinsed with 4° C. PBS, incubated with 0.5 mg/ml sulfo-EGS (Pierce) for 30 min., and lysed in 1% NP40 buffer. Lysates were clarified, precleared with agarose resin, incubated with protein A/G resin (Pierce) and anti-ADAM17 antibody (R&D Systems Duo-set) overnight, washed, and then boiled in denaturing lysis buffer. Methods roughly follow previously described protocols (Miller, M. A., Meyer, A. S., Beste, M. T., Lasisi, Z., Reddy, S., Jeng, K. W., Chen, C. H., Han, J., Isaacson, K., Griffith, L. G. et al. (2013). ADAM-10 and -17 regulate endometriotic cell migration via concerted ligand and receptor shedding feedback on kinase signaling, *Proc Natl Acad Sci USA* 110, E2074-E2083; Xu, P., Liu, J., Sakaki-Yumoto, M., and Derynck, R. (2012). TACE activation by MAPK-mediated regulation of cell surface dimerization and TIMP3 association, *Sci Signal* 5, ra34).

ADAM Activity Assays

Live-cell ADAM-10 and ADAM-17 catalytic activities were measured using proteolytic activity matrix analysis (PrAMA) (Miller, M. A., Barkal, L., Jeng, K., Herrlich, A., Moss, M., Griffith, L. G., and Lauffenburger, D. A. (2011), Proteolytic Activity Matrix Analysis (PrAMA) for simultaneous determination of multiple protease activities, *Integr Biol (Camb)* 3, 422-438). MDA-MB231 cells were seeded in serum-free media at 5000 cells per well of a 384-well plate, and the following day cells were simultaneously treated with either 10 μM U0126, 10 μM AZD6244, or 0.1% DMSO, along with one of six different FRET protease substrates (PEPDAB-05, 08, 10, 11, 14, 22; Biozyme, Inc.) at 5 μM concentration. Substrate cleavage was monitored over 3 h, and average cleavage rates were deconvolved into specific protease activities using Matlab (Mathworks, Natick, Mass.), as previously described (Miller, M. A., Barkal, L., Jeng, K., Herrlich, A., Moss, M., Griffith, L. G., and Lauffenburger, D. A. (2011), Proteolytic Activity Matrix Analysis (PrAMA) for simultaneous determination of multiple protease activities, *Integr Biol (Camb)* 3, 422-438). The ADAM17 IP & activity assay followed manufacturer's instructions (Innozyme TACE activity assay, EMD Millipore, Billerica, Mass.) and previously described protocols (Miller, M. A., Meyer, A. S., Beste, M. T., Lasisi, Z., Reddy, S., Jeng, K. W., Chen, C. H., Han, J., Isaacson, K., Griffith, L. G. et al. (2013), ADAM-10 and -17 regulate endometriotic cell migration via concerted ligand and receptor shedding feedback on kinase signaling, *Proc Natl Acad Sci USA* 110, E2074-E2083).

AXL Immunoprecipitation and on-bead Digestion 15 cm plates of MDA-MB231 cells were lysed in 1% NP40 lysis buffer, clarified, precleared with agarose resin, and incubated with protein A/G resin (Pierce) and 10 μg anti-AXL antibody mAb154 (R&D Systems, Minneapolis, Minn.) overnight. After repeated washing, the resin was split into separate samples for digest. Equal concentrations of ADAM-10 and -17 (R&D Systems, Minneapolis, Minn.) were incubated with resin for 4 h. Supernatant was collected, and both supernatant and resin were then boiled in denaturing sample buffer. Cleavage products were blotted using an antibody targeted to the intracellular C-terminus of AXL (Santa Cruz Biotechnology, Dallas, Tex.).

Cell Cycle Analysis

Cells were trypsinized, rinsed in 4° C. PBS, fixed in 70% 4° C. ethanol overnight, rinsed, and permeabilized in 0.1% Triton-X-100. Cells were then blocked for 1 h in PBS+3% FBS, incubated with anti-phospho-Histone H3 (pSer$^{10}$) for 1 h, rinsed, incubated with Alexa647-conjugated 2° Ab, and again rinsed. Lastly, cells were finally incubated at 37° C. for 1 h with 40 μg/ml propidium iodide and 100 μg/ml RNaseA, and again rinsed. Mitotic index was calculated by interpreting DNA-content histograms as described previously (Watson, J. V., Chambers, S. H. & Smith, P. J. A pragmatic approach to the analysis of DNA histograms with a definable G1 peak. *Cytometry* 8, 1-8 (1987)) in Matlab (Mathworks, Natick, Mass.) and gating for G2/M phase cells with high p-Histone-H3 staining.

Cancer Cell Line Encyclopedia (CCLE) Analysis

Previously published CCLE data was used to measure correlation between basal RNA expression of key proteins (measured by RNA microarray) and the average cell-line sensitivity to two Mek inhibitors (AZD6244 and PD325901), which were measured by the calculated "activity area" of a dose-response in a viability/cytotoxicity assay (Barretina, J., Caponigro, G., Stransky, N., Venkatesan, K., Margolin, A. A., Kim, S., Wilson, C. J., Lehar, J., Kryukov, G. V., Sonkin, D. et al. (2012), The Cancer Cell Line Encyclopedia enables predictive modelling of anticancer drug sensitivity, Nature 483, 603-607). Analysis was limited to cell lines expressing a minimum amount of each gene of interest (normalized RNA expression >5). Among cell lines meeting this criterion, Pearson correlation was calculated between RNA expression (or the sum of RNA expression of multiple-gene signatures) and the average sensitivity to the two Mek inhibitors. Statistical significance was calculated by a permutation test. Drug sensitivities were randomly shuffled relative to RNA expression, and the p-value statistic corresponding to the correlation of the shuffled data was reported. This procedure was repeated 100,000 times, creating a distribution of p-values observed by correlation among the randomly shuffled data. The p-value was compared from the actual data to this distribution of p-values, yielding a "corrected" p-value that is reported in FIG. 5A.

Proliferation/Cytotoxicity and Synergy Calculation

Proliferation and cytotoxicity were assessed by gently rinsing cells, trypsinizing for 15 min, and immediately counting cells by flow-cytometry. Live/dead staining routinely confirmed the majority (>98%) of counted cells to be alive using this procedure. Synergy was calculated using the model of Bliss independence (Bliss, C. I. The toxicity of poisons applied jointly Annals of applied biology 26, 585-615 (1939)), reported herein as the ratio of [observed combination effect size]/[predicted combination effect size], such that values >1 indicate super-additive drug effect, or synergy, and values <1 indicate antagonism. Drug concentrations for synergy measurements were chosen to roughly approximate the $IC_{30}$ value averaged across the panel of cell lines for the individual drug treatments, and were 20 μM U0126, 7 μM PD325901, and 200 nM R428.

Figure 12A:
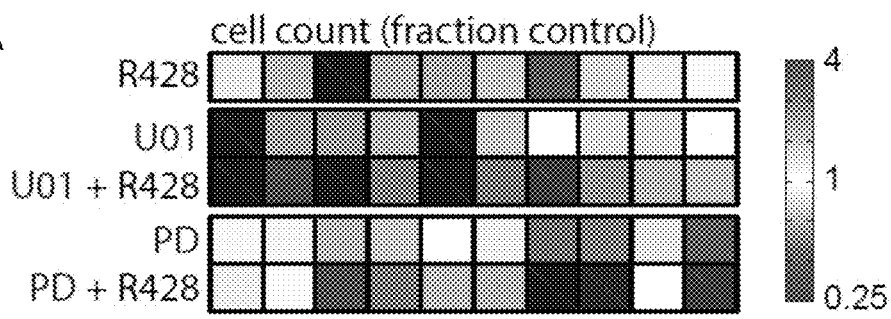
FIG. 12A-12D correspond to FIG. 5B, showing U0126 and PD325901 elicit AXL up-regulation to a degree that correlates with AXLi/MEKi synergy across a panel of cell lines (U01=U0126; PD=PD325901).
Figure 12B:
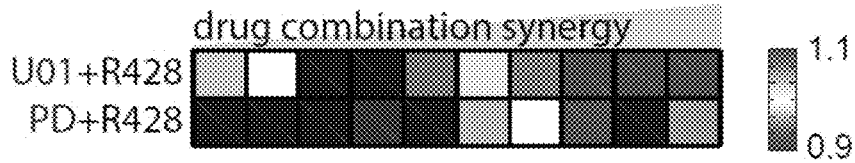
Figure 12C:
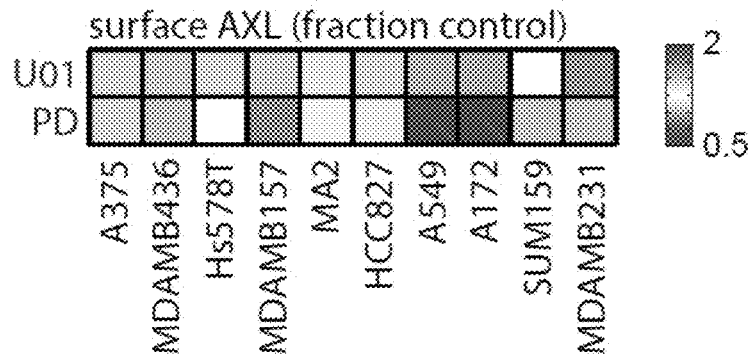
Figure 12D:
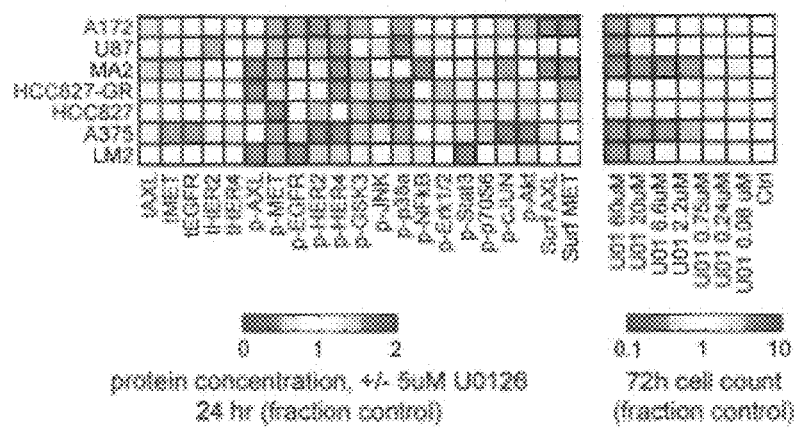

For calculating RNA expression correlations with MEKi/AXLi synergy, RNA expression was obtained from CCLE data for 9/10 cell lines shown in FIG. 12A-12C (the MA2 cell line is not assessed in the CCLE data). Cell lines were grouped according to those displaying synergistic vs. antagonistic drug interactions, and RNA expression (or summed RNA expression of all four genes tested, in the case of "combo") was compared between groups using a two-tailed student's t-test.

Example One

MEK Inhibition Causes Global Reduction in Cell-surface Proteolysis and Subsequent Accumulation of Total and Phosphorylated Receptors on the Cell Surface Relatively little is known regarding how the composition of the tumor-derived extracellular proteome changes in response to targeted kinase inhibitor treatment, and how such changes affect drug efficacy. Antibody microarrays were used to screen 1000 proteins for differential supernatant accumulation following MEKi in the TNBC (specifically "claudin low") MDA-MB231 cell line. Gene set enrichment analysis (Subramanian et al., 2005) of the ~200 proteins exhibiting significantly altered levels in the supernatant indicated that MEKi reduced transmembrane receptor ectodomain abundance (FIG. 1A) and increased secreted (not proteolytically shed) cytokines (FIG. 8A). The top-ranked "transmembrane receptor activity" gene-set (FIG. 1A) comprised various known sheddase substrates including amyloid precursor protein (APP) (Asai, M., Hattori, et al., Putative function of ADAM9, ADAM10, and ADAM17 as APP alpha-secretase. Biochem Biophys Res Commun 301, 231-235 (2003)) and low-density lipoprotein receptor (LDLR) (Guo, L., et al., A proteomic approach for the identification of cell-surface proteins shed by metalloproteases. Mol Cell Proteomics 1, 30-36 (2002)), implicating reduced sheddase activity as a key effect of MEKi. Using the MEK inhibitor U0126, MEKi was shown to consistently reduce supernatant levels of multiple sheddase substrates, including growth factor ligands (AREG, HBEGF, TGFα), the cytokine receptor TNFR1, and four RTKs (AXL, MET, HER2, HER4) in MDA-MB231 cells (FIG. 8B). The generality of this result was tested across a panel of 12 other cell lines from several cancer types including TNBC, malignant melanoma (MM), non-small cell lung cancer (NSCLC), and glioblastoma multiforme (GBM), and MEKi was found to extensively reduce shedding of multiple sheddase substrates (FIG. 1B; FIG. 8B). Treatment with another MEK inhibitor (PD325901), or broad-spectrum metalloproteinase inhibition (MPi) with BB94, also reduced supernatant RTK accumulation in multiple cancer types (FIG. 8B). Furthermore, gene expression profiling using RNA microarrays identified overlap in the transcriptional responses arising from MEKi and MPi, suggesting a shared mechanism of action (FIG. 1C; FIG. 8C). However, gene set enrichment analysis indicated that MEKi, but not MPi, induced growth arrest (FIG. 8D). MPi did not elicit any significant gene-set enrichment. Together, these results show that reduced sheddase activity is a surprisingly prominent effect of MEKi, affecting a broad range of substrates and cancer types.

Figure 8F:
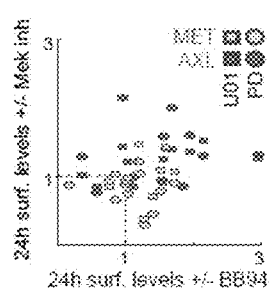

The correlation of decreased supernatant accumulation of sheddase substrates with changes of their cell surface levels was also assessed. Among 18 sheddase substrates implicated from literature or the Ab-microarray, MPi and MEKi increased surface AXL to the greatest degree (FIG. 1D). Lack of transcriptional feedback on AXL partly explores this significantly. Unlike several other sheddase substrates, AXL was not down-regulated transcriptionally by drug treatment (FIG. 1E; FIG. 8E). MEKi increased surface AXL, and, to a lesser degree, MET in the majority of 16 cell lines tested. Furthermore, surface-level changes induced by MEKi correlated with those following MPi, across the 16 cell lines (FIG. 8F). Consistent with the increased surface levels, MEKi and MPi also increased AXL phosphorylation (FIG. 1F). Moreover, both treatments increased co-immunoprecipitation of AXL with MET and HER2, which has been associated with AXL transactivation (FIG. 1G) (Meyer et al., 2013). Overall, reduced shedding via MEKi leads to accumulation of multiple cell-surface RTKs, with corresponding increases in both AXL phosphorylation and association with interacting RTKs.

Figure 8G:
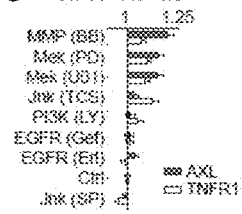

Reduced sheddase activity consequent to kinase inhibition was not exclusive to MEKi. Among 19 clinical and pre-clinical inhibitors targeting various signaling pathways and RTKs, roughly 80% inhibited substrate shedding to some degree, with MEKi exhibiting prominent effects (FIG. 1H). p38 inhibition also exhibited strong effects, consistent with previous reports describing direct ADAM17 regulation by p38 (Xu & Derynck 2010). PI3K and JNK inhibitors also strongly reduced ectodomain shedding, as seen in other disease contexts such as endometriosis (Miller et al., 2013). Surface levels of two sheddase-substrates (AXL and TNFR1) correspondingly increased in response to several other kinase inhibitors, but most significantly with MEKi (FIG. 8G).

Example 2

Figure 9A:
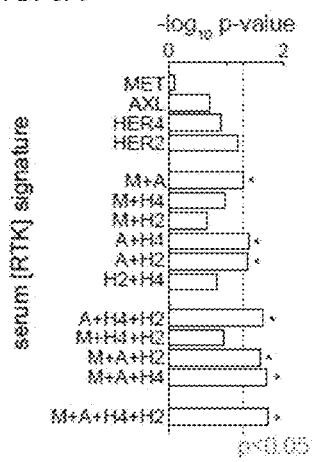
FIG. 9A-9F.

RTK Shedding Significantly Impacts Downstream Signaling Activity and is Detectable in Breast Cancer Patient Serum To check whether RTK shedding may be relevant to clinical pathology as well as cell culture, serum levels of AXL, MET, HER2, and HER4 ectodomains in stage IV breast cancer patients and healthy controls were measured. It was observed that AXL contributes to an overall pattern of increased RTKs in patients. Previous reports indicate that many RTKs are expressed and proteolytically shed under physiological conditions (Gooz 2010), and that ADAM17 expression (McGowan et al., 2007) and MEK/ERK activity (Bartholomeusz et al., 2012; Zardavas et al., 2013) can be up-regulated in breast cancers. It was found that the combined level of these four RTKs in a given serum sample was increased significantly in breast cancer patients compared to controls (FIG. 2A-2B). In other words, roughly 40% of patient samples exhibited a "quadruple-positive" phenotype with increased levels of all four RTKs in circulation, compared to 0% of healthy controls (FIG. 2B). The statistical significance of this metric, and of potential "double-" and "triple-positive" trends calculated in an analogous manner, were all dependent upon inclusion of AXL measurements (FIG. 9A), indicating it as the most vital among the four.

Figure 2F:
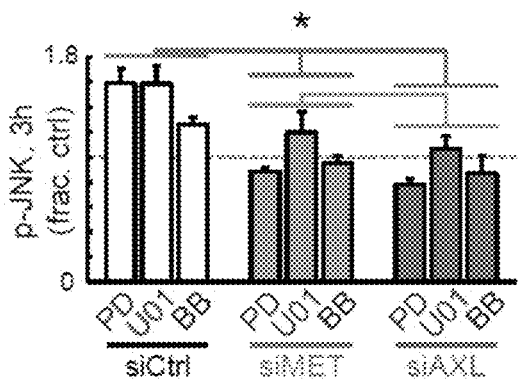
Figure 9B:
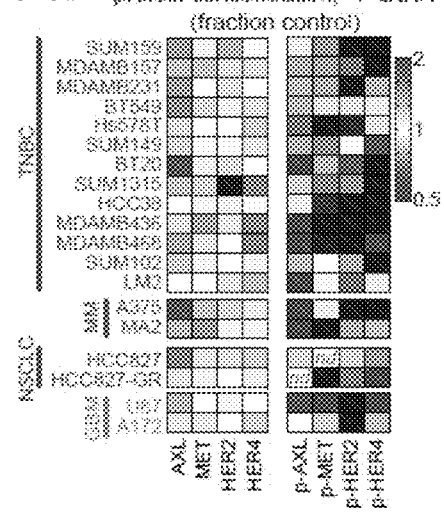
Figure 9C:
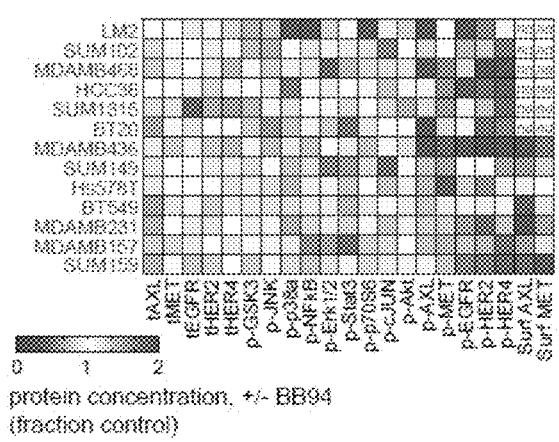
Figure 9D:
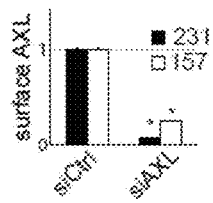
Figure 9E:
Figure 9F:
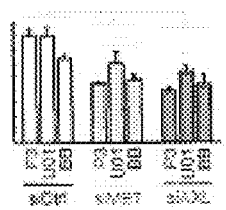

The effects of RTK shedding were examined across a panel of 19 cancer cell lines, and it was found that MPi increased total and phospho-RTK levels in many cell lines, most significantly for AXL and MET (FIG. 2C; FIG. 9B). Measurements of 21 signaling protein activities in response to MPi (FIG. 9C) showed that changes in surface AXL and MET most strongly correlated with changes in p-AXL, p-JNK, p-cJUN, and p-ERK1/2 (FIG. 2D; FIG. 9C). As expected, the increased AXL signaled through JNK since the substantial MPi-evoked p-JNK increase in MDA-MB231 was eliminated by co-treatment with either R428 (also known as BGB324), a clinically-tested AXL kinase inhibitor (Holland, S. J., et al. R428, a selective small molecule inhibitor of Axl kinase, blocks tumor spread and prolongs survival in models of metastatic breast cancer. Cancer Res 70, 1544-1554 (2010); Sheridan, C. First Axl inhibitor enters clinical trials. Nat Biotechnol 31, 775-776 (2013)) (AXLi; FIG. 2E; p=0.01; n=8) or with AXL siRNA (FIG. 2F; FIG. 9D). MET knockdown also reduced p-JNK, though to a lesser extent than AXL (FIG. 2F; FIG. 9E), underscoring that proteolytic RTK shedding has a broad effect on RTK signaling and is not specific to AXL. Similar to MPi, MEKi also increased p-JNK in manner likewise dependent upon MET and especially AXL (FIG. 2F). Overall, MPi and MEKi evoke up-regulated signaling through multiple receptors, including MET and AXL, with pronounced downstream effects through JNK.

Example 3

Figure 3C:
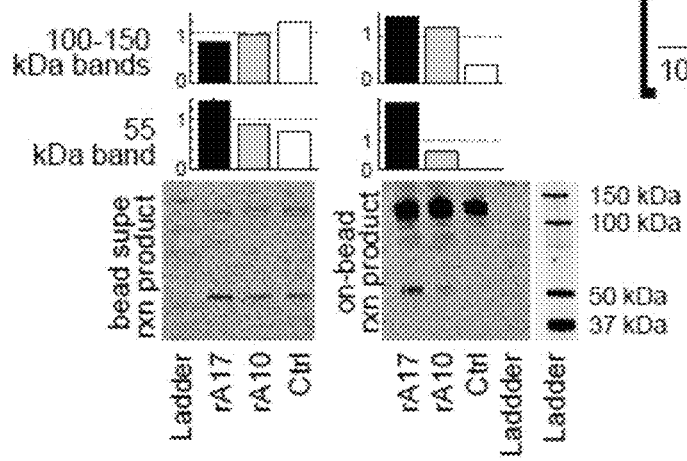
Figure 3D:
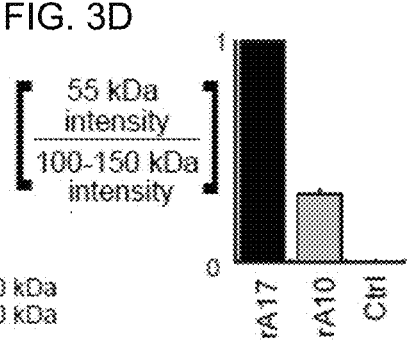
Figure 10:
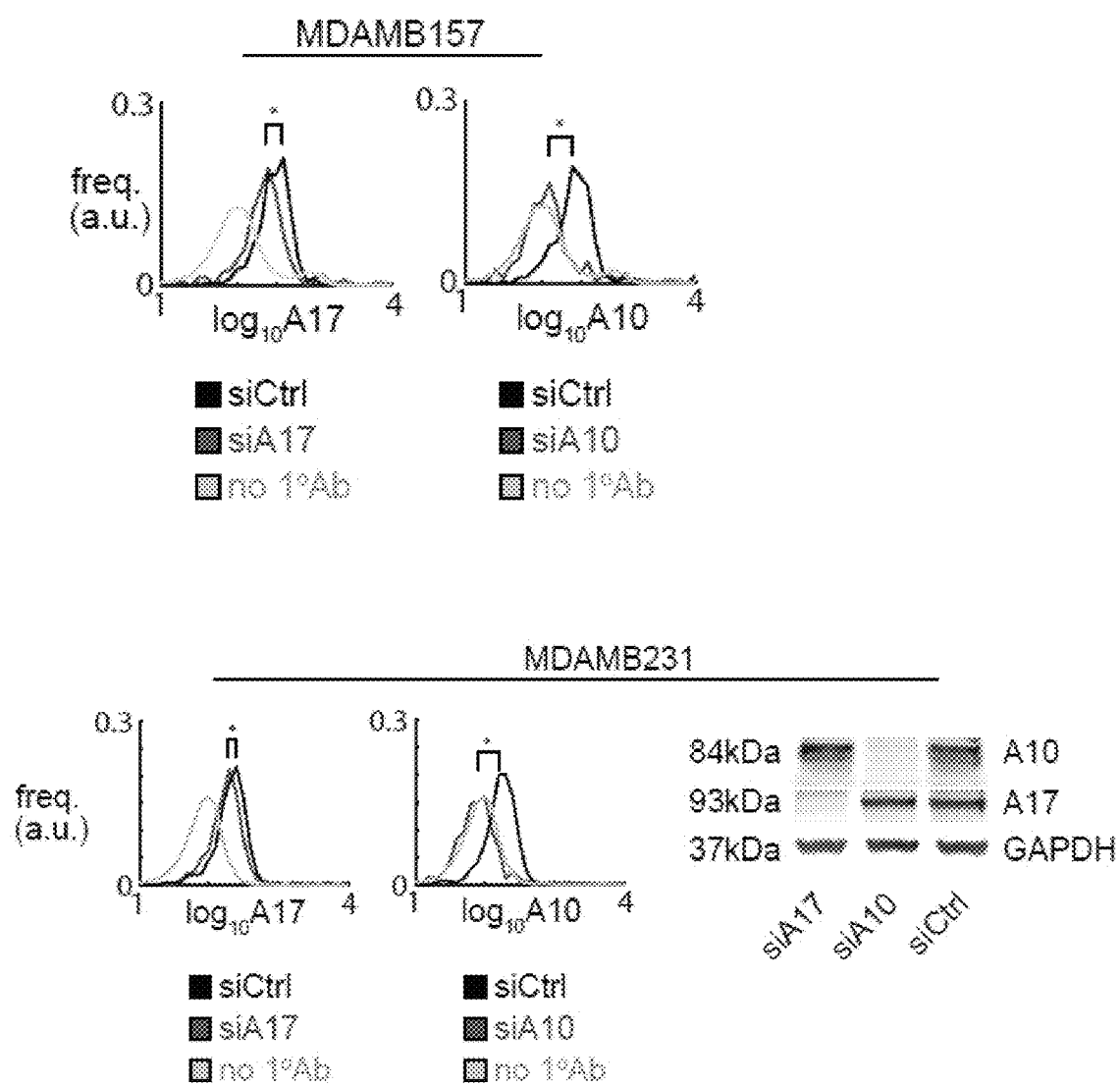
FIG. 10 illustrates validation of ADAM10 and ADAM17 siRNA knockdown in MDA-MB157 and MDA-MB231, assessed by live-cell immunostaining and confirmed in the far right panel by western blot in MDA-MB231 (*p<0.05).

ADAM10 and ADAM17 Proteolytically Shed AXL and Down-regulate Mitogenic JNK Pathway Activity Sheddases that cleave AXL directly were investigated, and it was ascertained that ADAM10 and ADAM17 both play roles. ADAM10 or ADAM17 knockdown each reduced supernatant AXL (FIG. 3A; FIG. 10), while increasing its surface levels (FIG. 3B). Furthermore, recombinant ADAM10 and ADAM17 both cleaved immunopurified AXL in an on-bead digest (FIG. 3C-3D). Finally, a specific ADAM10 inhibitor (proADAM10) reduced supernatant AXL accumulation (FIG. 3A). Overall, ADAM17 exhibited slightly stronger effects on AXL compared to ADAM10 in knockdown and recombinant enzyme experiments, suggesting it to be a primary sheddase.

Figure 3E:
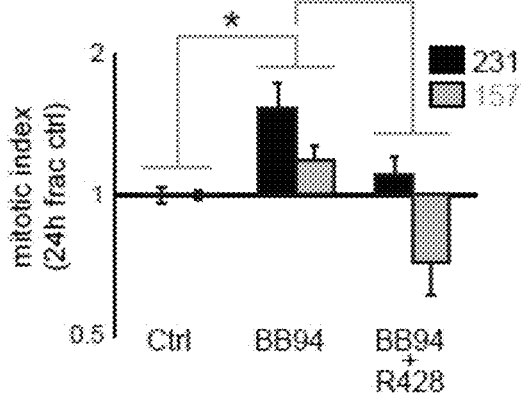
Figure 3F:
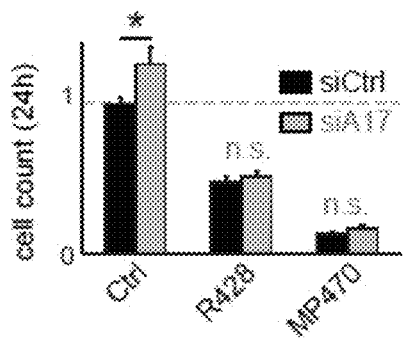

Downstream of phospho-signaling, sheddase inhibition stimulated an AXL-dependent increase in proliferation. MPi caused an increased mitotic index only in the presence of AXL signaling (FIG. 3E). ADAM17 knockdown also enhanced proliferation, again only in the absence of the AXL inhibitors R428 and MP470 (FIG. 3F). This was concerning, considering that sheddase inhibitors are actively being developed for cancer treatment, with a focus on blocking EGF-ligand shedding (Duffy et al., 2013). Nonetheless, MDA-MB231 cells, which harbor Kras and Braf mutations (Barretina et al., 2012), are highly resistant to inhibition of EGFR autocrine signaling (Meyer et al., 2013), and the data indicates that ADAM17-mediated AXL shedding attenuates AXL signaling activity and consequent proliferation.

Example 4

Figure 4B:
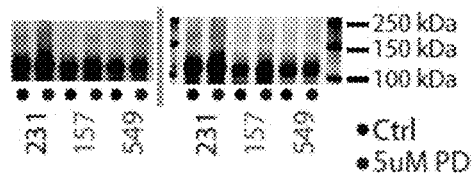
Figure 4C:
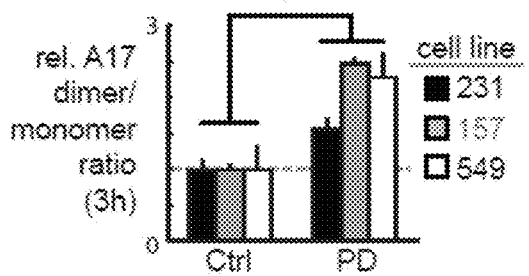
Figure 4D:
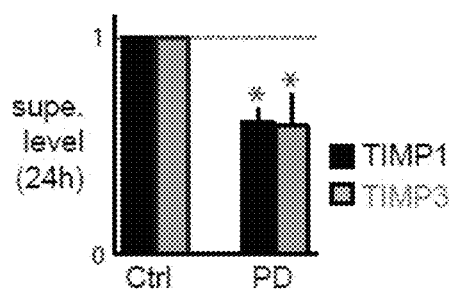
Figure 4E:
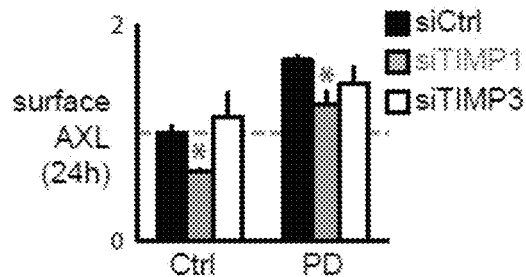
Figure 4F:
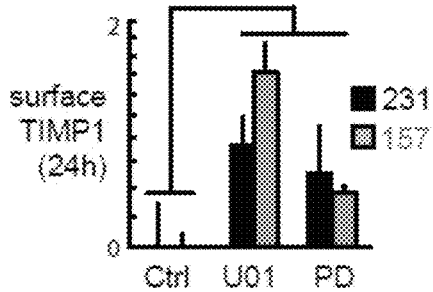
Figure 4G:
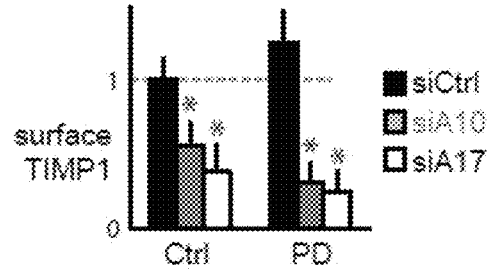
Figure 4H:
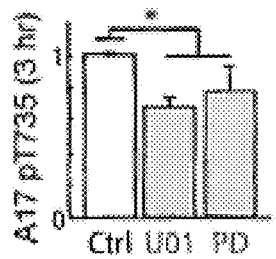
Figure 11A:
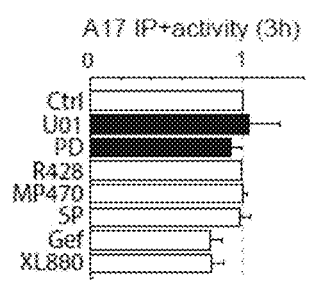
FIG. 11A-11E.
Figure 11B:
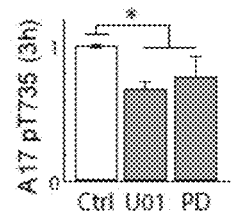
Figure 11C:
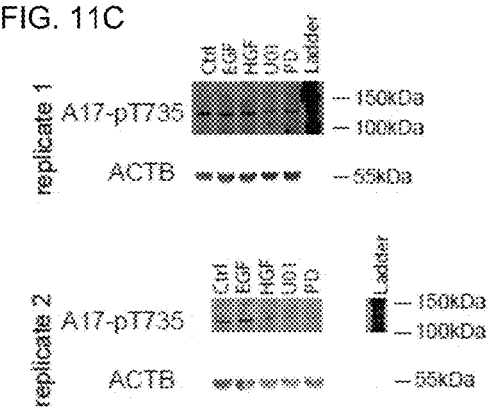
Figure 11D:
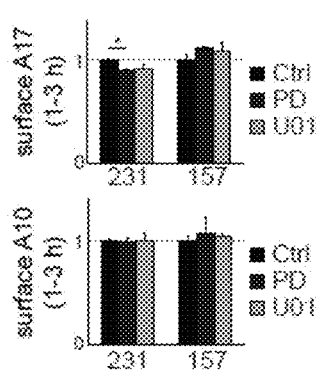
Figure 11E:
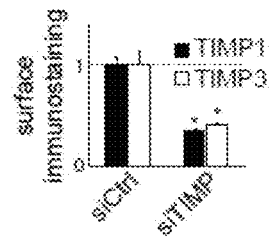

MEK Inhibition Leads to Reduced Sheddase Activity Via Enhanced TIMP1 Association The mechanism underlying the effects of MEKi on sheddases was investigated. While MEKi significantly decreased ADAM10 and ADAM17 activities in a live-cell assay (Miller et al., 2011) (FIG. 4A), the total level of ADAM17 activity in cell lysates was not reduced significantly (FIG. 11A). ADAM17-T735 is a known ERK phosphorylation site (Diaz-Rodriguez et al., 2002), and it was confirmed that MEKi reduced $p^{T735}$-ADAM17 levels (FIG. 11B-11C). T735 phosphorylation regulates ADAM17 surface presentation (Soond, S. M., et al. ERK-mediated phosphorylation of Thr735 in TNFalpha-converting enzyme and its potential role in TACE protein trafficking J Cell Sci 118, 2371-2380 (2005)), and the ADAM17 c-terminus is known to regulate homodimerization (Xu et al., 2012). MEKi decreased ADAM17 surface levels slightly (FIG. 11D), while increasing its surface homodimerization significantly (FIG. 4B-4C). Homodimerization of ADAM17 is thought to reduce its activity by promoting association with the endogenous inhibitor "Tissue Inhibitor of Metalloproteinase 3" (TIMP3) (Xu et al., 2012). Consistent with this model, decreased supernatant TIMP3 upon MEKi was observed (FIG. 4D). Unexpectedly, MEKi concomitantly decreased supernatant levels of the closely related TIMP1 (FIG. 4D), and TIMP1 knockdown significantly reduced AXL surface levels while TIMP3 knockdown did not (FIG. 4E). Surface TIMP1 correspondingly increased with MEKi (FIG. 4F), in a ADAM10- and ADAM17-dependent manner (FIG. 4G). Overall, these results show that MEKi inhibits substrate shedding broadly by direct negative regulation of ADAM17 activity arising from its enhanced homodimerization and association with TIMP1.

Example 5

AXL Shedding Mediates MEK Inhibitor Resistance

Figure 5A:
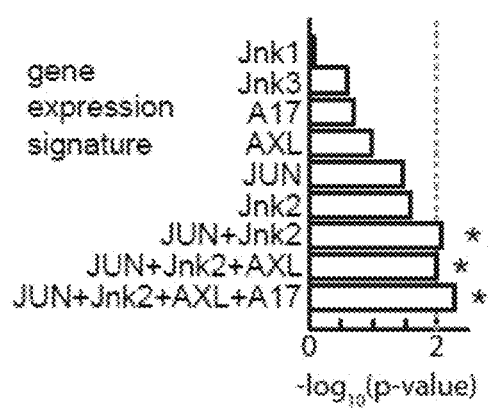
FIG. 5A-5D illustrates that sheddase-mediated AXL feedback activity correlates with MEKi resistance and synergistic response to dual MEK and AXL inhibition.
Figure 5B:
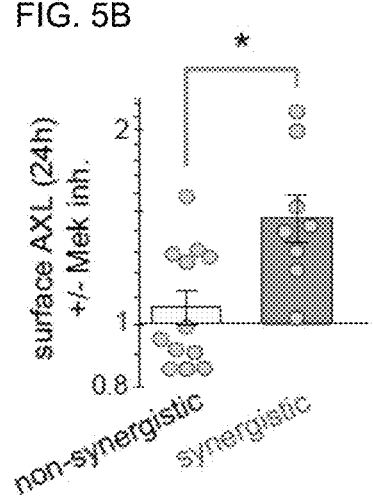
Figure 5C:
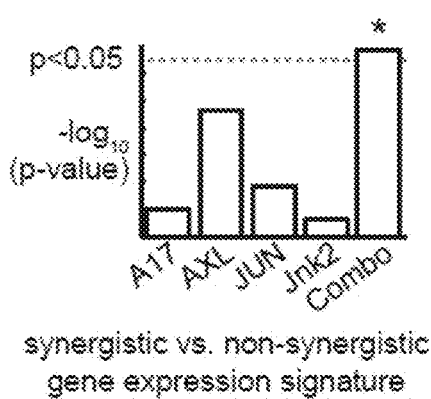
Figure 5D:
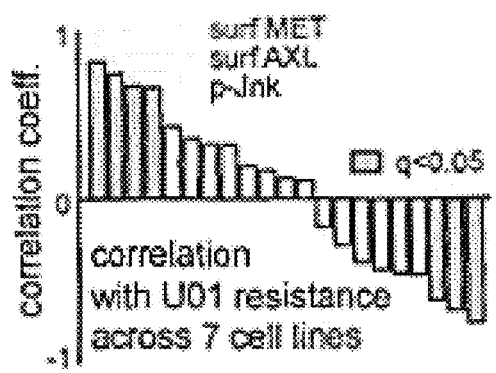

Next, the effects of reduced sheddase activity and consequent bypass signaling on cell growth in response to MEKi were assessed. A comprehensive range of cancer types was examined by measuring how basal RNA expression of central genes in the model of sheddase-mediated feedback quantitatively correlated with resistance to two different MEK inhibitors (AZD6244/selumetinib and PD325901), as they varied across more than 450 cancer cell lines in the Cancer Cell Line Encyclopedia (CCLE) (Barretina et al., 2012). The mRNA expression of key genes in the ADAM17/AXL/JNK/Jun bypass pathway correlated significantly with MEKi resistance, especially in combination (FIG. 5A). Motivated by these data, potential synergies in MEKi/AXLi combination treatment were assessed across 10 cell lines (FIG. 12A-12C). Consistent with the model, cell lines displaying synergistic response to combined AXLi/MEKi also showed corresponding up-regulation of surface AXL following MEKi, in comparison to cell lines displaying nonsynergistic responses (FIG. 5B; FIG. 12C). The correlation of basal RNA expression of key genes in the bypass model with MEKi/AXLi synergy across 9 cell lines was also examined (FIG. 12C). It was found that the summed expression of the four key genes was elevated in cell lines showing synergy (FIG. 5C).

The results led to the prediction that combined AXL and MEK inhibition would yield synergistic efficacy against tumor growth and progression. The in vivo effects of dual MEKi/AXLi were tested with an orthotopic xenograft animal model of TNBC using the highly lung-metastatic derivative of MDAMB231, LM2 (Minn, A. J., et al. Genes that mediate breast cancer metastasis to lung. Nature 436, 518-524 (2005)).

In Vivo Tumor Growth and Metastasis Assays

All animal experiments and husbandry were approved by the MIT Division of Comparative Medicine. For orthotopic mammary transplant assays, 6-week-old female NOD/SCID-gamma mice (JAX) were anesthetized by intraperitoneal (i.p.) injection of 125-250 mg/kg body weight of Avertin (reconstituted in PBS), followed by i.p. injection of 100 µL, of 12 µg/mL buprenorphine for analgesia. A small incision was made on the right flank, and 250,000 MDA-MB231-LM2 cells in 25 µL, of HBSS were injected into the right #4 fat pad using a 25-µL Hamilton syringe. Mice received three additional i.p. injections of 100 µL, of 12 µg/mL buprenorphine at 12 h intervals following the surgery. Initial sample size was chosen based on previously published experiments with MDA-MB231-LM2 xenograft models (Minn et al., 2005), as well as previously published data with the MEK and AXL drugs of interest (Holland et al., 2010; Hoeflich, K. P., et al. In vivo antitumor activity of MEK and phosphatidylinositol 3-kinase inhibitors in basal-like breast cancer models. Clin Cancer Res 15, 4649-4664 (2009)). Twenty (20) days post-surgery, when tumor size was palpable, mice were ranked by tumor size and semi-randomly divided into four groups of equal distribution in tumor size. Groups received one of four different drug treatments once daily for 21 days by oral gavage: vehicle (10% DMSO+0.5% methylcellulose+0.2% tween-80 in water), AXL inhibitor R428 at 30 mg/kg, PD0325901 at 1 mg/kg or a combination of both R428 at 30 mg/kg and PD0325901 at 1 mg/kg.

Tumor volume was measured twice a week, estimated using the spherical tumor volume formula $V=4/3\pi r3$, where r is averaged from 4 caliper measurements performed by two blinded researchers. Animals were sacrificed at the predetermined time of 21 days following initiation of drug treatment. Upon sacrifice, the lungs were inflated with and fixed in 3.7% (wt/vol) formaldehyde for 24 h, followed by 24 h in 75% (vol/vol) ethanol. For metastasis quantification, the numbers of metastases were counted in paraffin-embedded, H&E-stained sections, by a blinded researcher. Upon sacrifice, blood was collected via cardiac puncture into a heparinized syringe, immediately centrifuged at 2000×g for 20 min, and plasma fraction was stored at −80° C. for later quantification of receptor levels by ELISA and bead-based immunoassay.

Figure 6A:
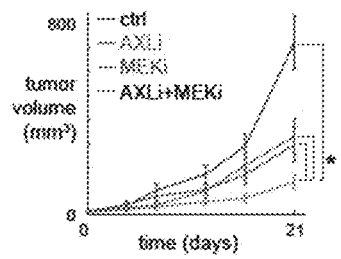
FIG. 6A-6G illustrates that combination MEK and AXL inhibition synergistically reduce tumor growth and metastasis in a xenograft mouse model of TNBC.
Figure 6B:
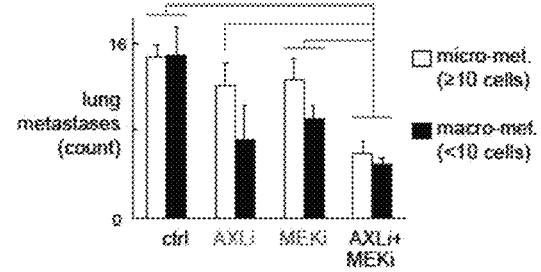
Figure 6C:

For immunostaining primary tumor sections, tumors were formalin-fixed overnight and paraffin embedded. Tissue sections (5 µm thick) were deparaffinized followed by antigen retrieval using Citra Plus solution (Biogenex, Fremont Calif.). Sections were incubated with primary antibodies for AXL (R&D Systems, Minneapolis, Minn., MAB154, 1:50) and MET (R&D Systems, Minneapolis, Minn., AF276, 1:20) overnight at 4° C. and fluorescently labeled secondary antibodies (AlexaFluor 594 and AlexaFluor 647, Jackson Immunoresearch, West Grove, Pa.) at room temperature for 2 h. Sections were mounted in Fluoromount mounting media and imaged at room temperature. Images (5×5 fields) were captured with a Nikon TE2000 microscope (TE2000, Nikon) with a 20× objective and a Photometrics Coolsnap HQ camera. AXL and MET staining was performed simultaneously across all samples, and imaging was performed in a single session using identical exposure settings. Exposure adjustments were made for DAPI staining shown in FIG. 6C.

MET and AXL levels were quantified by measuring fluorescent staining intensity over a line drawn radially from the tumor edge towards the tumor core. The very immediate edge of the tumor (0-30 µm), which generally appeared to contain compacted tissue and/or highly auto-fluorescent adipose tissue with distinct morphology, was ignored. The beginning of the "tumor edge" was considered as the tumor region exhibiting regularly spaced nuclei determined through DAPI counter-staining (generally the 2nd or 3rd observable nucleus observable along the radial line by DAPI counter-stain intensity). Regions with morphology characteristic of stroma or necrosis were generally avoided during quantification. Peak intensities along the line were confirmed by visual inspection as corresponding to cell membranes, and were quantified and indexed according to the distance from the tumor edge. This process was repeated for n≥4 lines per tumor by a blinded researcher, and data were averaged accordingly. This was repeated across n≥3 separate tumors per treatment group, and average results for each tumor were background-corrected according to control tumor sections that were staining without primary antibody. Average results for each tumor were used to calculate statistics between treatment groups, using the two-way student's t-test.

Exclusion criteria were used for mice that were pre-determined at the onset of the experiment. Mice were excluded that failed to ever develop a tumor (n=4/37, confirmed by dissection). All other mice had tumors on dissection. Among mice with successful tumor implantation, no significant difference was observed in pre-drug tumor volume across the four groups. One mouse asphyxiated during gavage treatment, all others survived for the duration of the experiment. Among mice with successful tumor implantation, two were excluded that exhibited a pre-drug tumor volume falling >2 standard deviations from the mean, across all groups (n=2/33 tumor-developing mice). Final sample sizes for the treatment groups, after exclusions described above, were n=7 controls, n=7 AXLi, and n=8 for the other groups.

Figure 6D:
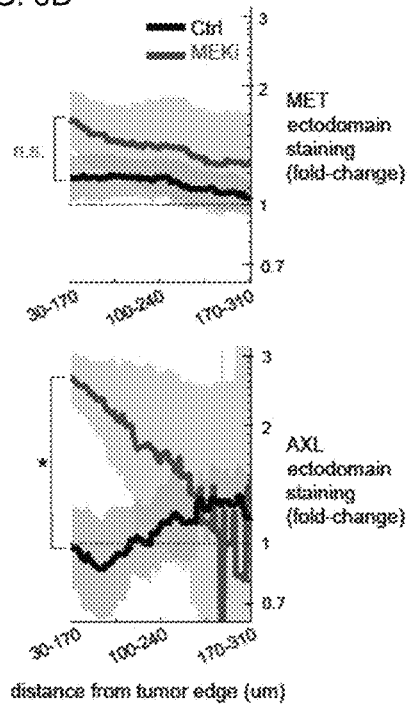
Figure 6E:
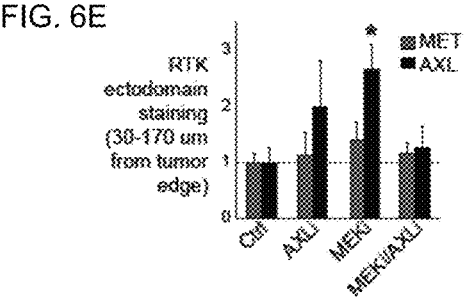
Figure 6F:
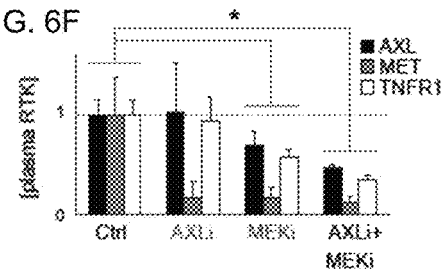
Figure 6G:
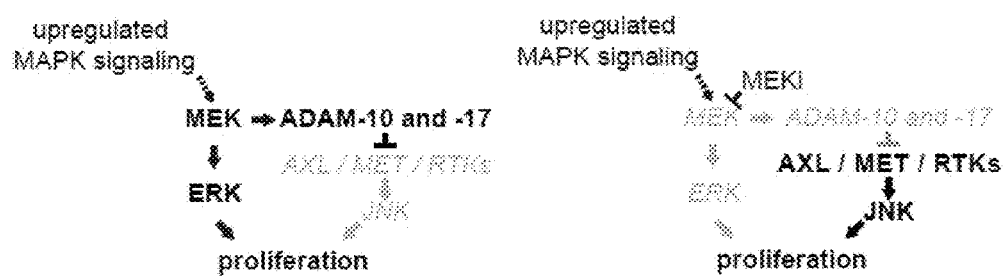

Combination MEKi/AXLi treatment reduced both tumor growth (FIG. 6A) and metastasis (FIG. 6B) more than either treatment alone, with significant synergy in tumor growth reduction (p=0.015; two-way ANOVA interaction term; n≥7). Furthermore, MEKi elicited increased immunostaining of AXL ectodomain near the primary tumor edges (FIG. 6C-6D) while none of the other treatments caused statistically significant changes in MET or AXL levels (FIG. 6E). The MEKi-dependent change in receptor ectodomain distributions could reflect reduced AXL shedding. This was tested by measuring circulating plasma levels of soluble receptors in tumor-bearing mice following drug treatment. Indeed, MEKi and combination AXLi/MEKi significantly reduced levels of the circulating sheddase substrates AXL, MET, and TNFR1 (FIG. 6F). These provide evidence that MEKi decreases receptor shedding in a live-animal cancer model and demonstrate an ability to use circulating levels of sheddase substrates to monitor changes in RTK proteolysis following drug treatment.

Example 6

Metalloproteinase Activity Contributes to Drug Synergy; Combination MAPK and Sheddase-Substrate Inhibition is Effective Across Multiple Cancer Types and Inhibitors; TIMP1 Neutralization Enhances MEKi Efficacy Drugs were purchased from Selleck Chem (Houston, Tex.) and LC Labs (Woburn, Mass.). Cells were grown as described by manufacturers' guidelines. OVCA-429 were grown in RPMI+10% FBS. To calculate Loewe synergy, a computational model was used (Greco, W. R., et al., Pharmacol Rev., 47(2):331-85 (1995)) and the synergy term a was computationally inferred using Matlab (Mathworks; Natick, Mass.). Statistical significance was determined by leave-one-out jackknife error estimation (Efron, B. and Gong, G., Amer Stat.; 37(1):36-48 (1983)). For both MDAMB-231 and OVCA-429 synergy calculations, the modeling was fit to data from treatment at the MEKi concentrations of 7 µM, 2 µM, 0.7 µM, and 0.02 µM and R428 concentrations of 1.5 µM, 0.75 µM, 0.38 µM, and 0.19 µM. For cell growth assays, 5000 cells were plated per well in a 96-well plate, treated with drugs the following day, and counted at 72 h according to either a rezasurin assay (PrestoBlue; Life Technologies, Grand Island, N.Y.) using manufacturer's guidelines, or by flow cytometry following trypsinization and immediate analysis on an LSR-II (BD Biosciences, San Jose, Calif.).

TIMP1 Neutralization 5000 cells per well were plated in 96-well plates overnight and treated with 10 µg/ml TIMP1 neutralization antibody (T1-NAB; ABD-Serotec/Bio-Rad) or IgG control for 24 hours (h). The following day PD325901 was added to a final concentration of either 0.5 µM (OVCA-429 and MDAMB-231) or 5 µM (LOX-IMVI). 72 h after PD325901 treatment, cell count was assessed using the PrestoBlue assay (Life Technologies, Grand Island, N.Y.) according to manufacturer's guidelines.

Discussion

Figure 13A:
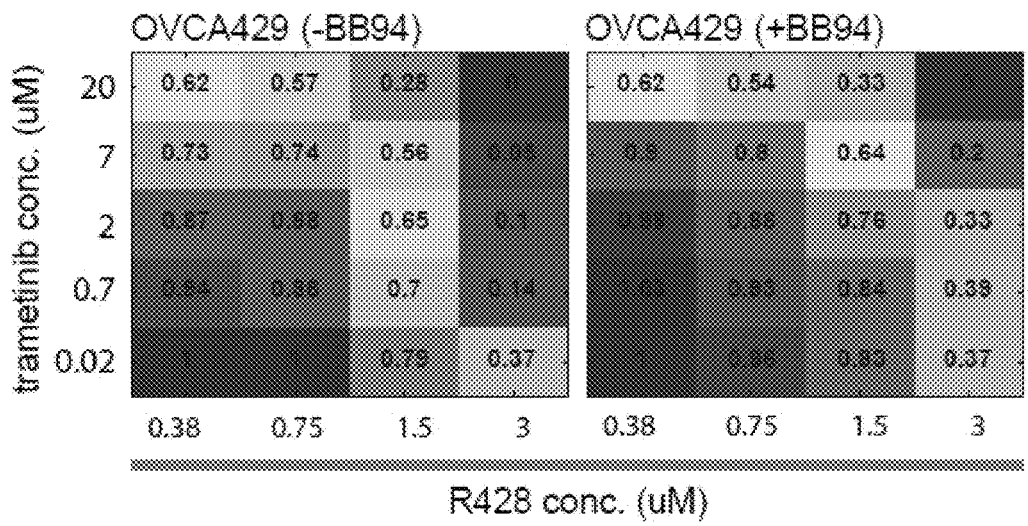
FIG. 13A-13B illustrates that synergy between MEKi and AXLi is metalloproteinase dependent.
Figure 13B:
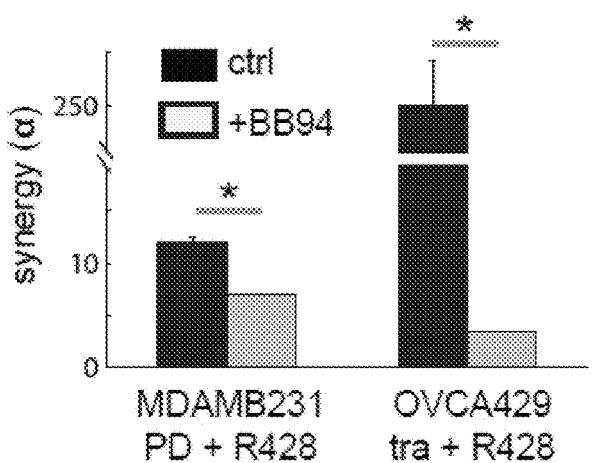

Studies were performed to test the metalloproteinase-dependency of AXLi/MEKi drug synergy. Cells were treated with varying combinations of AXLi or MEKi, in the presence or absence of the broad-spectrum metalloproteinase inhibitor BB94. Cell growth and cytotoxicity were measured after combination drug treatment (FIG. 13A), and results were fit to a computational model for determination of drug synergy. Results showed that elimination of metalloproteinase activity leads to a significant reduction in observed MEKi/AXLi synergy (FIG. 13B). This provides evidence that metalloproteinase activity contributes to the mechanism of MEKi/AXLi synergy.

Figure 14A:
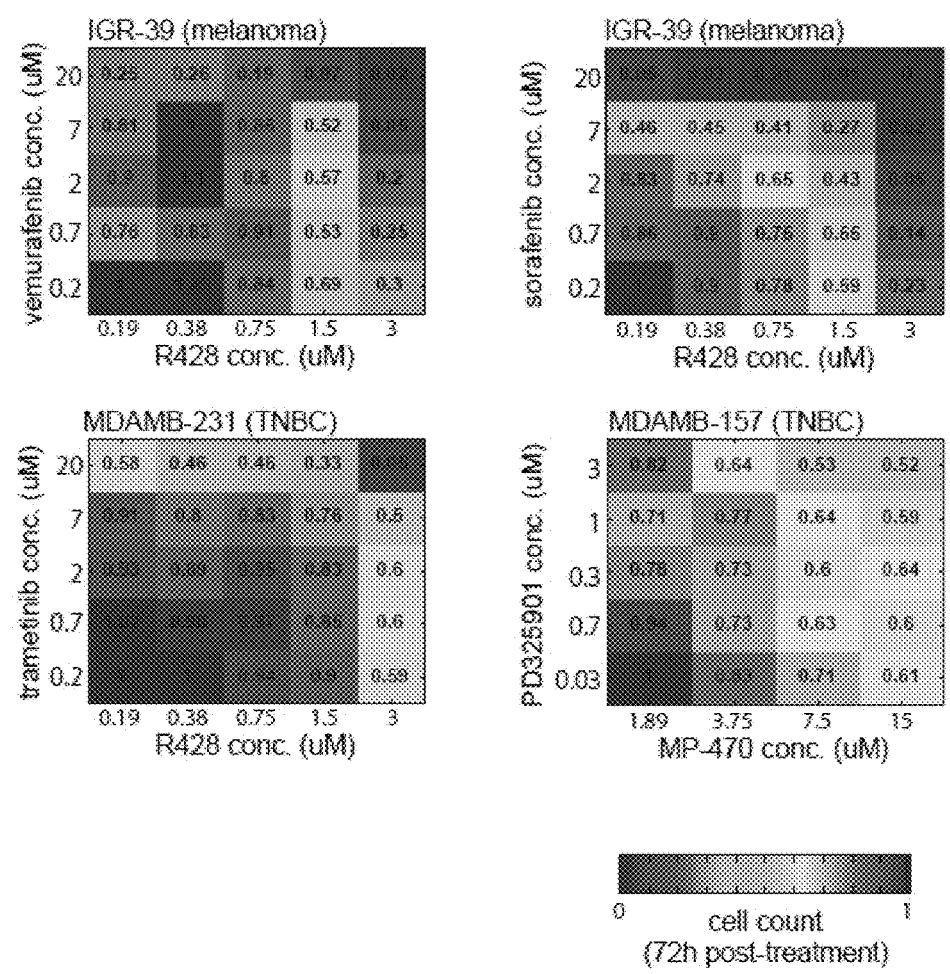
FIG. 14A-14B are heatmaps illustrating that combination drug treatments using multiple MEKi, PI3Ki, and AXLi drugs reduce cell growth in various cancer cell lines. Cells were treated with varying concentrations of inhibitors for 72 h, at which point cell count was assessed, shown by heatmap color and number after normalization to the untreated control.
Figure 14B:
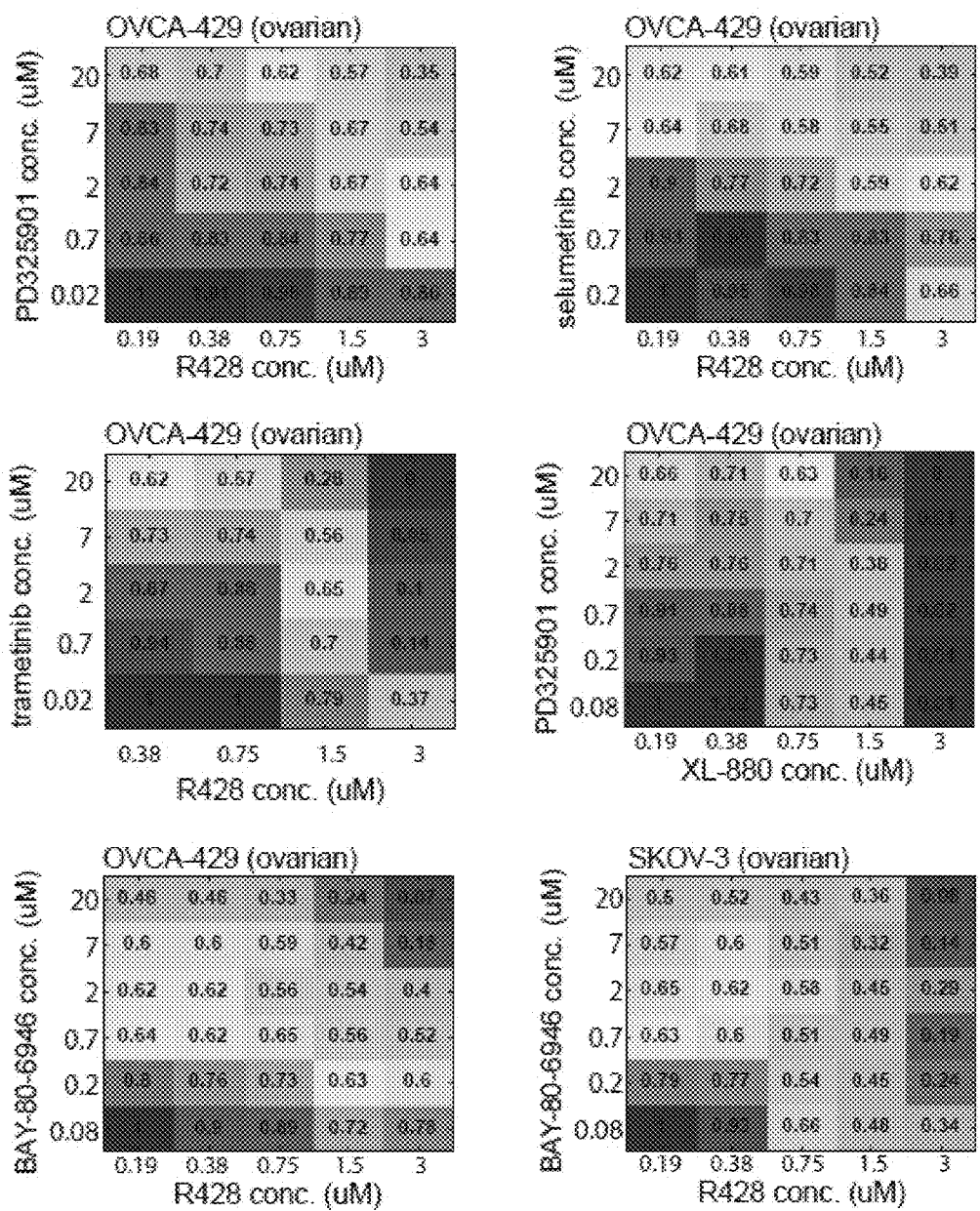

To examine the generalizability of the synergistic interaction between MAPK inhibition and sheddase-substrate inhibition, several additional cancer-types and drug combinations were examined (FIG. 14). Combination treatment with MAPK and RTK inhibitors increased treatment efficacy in both ovarian carcinoma and malignant melanoma. Furthermore, combination treatment was effective using other MAPK kinase inhibitors including the BRAF inhibitors vemurafenib and sorafenib, along with the MEK inhibitors trametinib and selumetinib. Combination treatment was efficacious using other RTK inhibitors targeting Met and AXL, including foretinib (XL880) and amuvatinib (MP-470). Therefore, drug combination treatment efficacy extends to multiple cancer-types and drug targets.

As discussed previously, this work found that MEKi elicits increased association of TIMP1 to the cell surface, which results in reduced RTK shedding. To mitigate this effect, a TIMP1 neutralizing antibody (T1-NAB; ABD Serotec) was applied to cells prior to MEKi treatment. While T1-NAB exhibited little effect as a single treatment, it significantly enhanced the efficacy of MEKi (FIG. 15). This suggests that TIMP1 significantly contributes to MAPK inhibitor resistance through its role in blocking ADAM activity and RTK shedding, and offers T1-NAB as a possible co-therapy to synergistically combine with MAPK inhibition.

Example 7

Figure 16B:
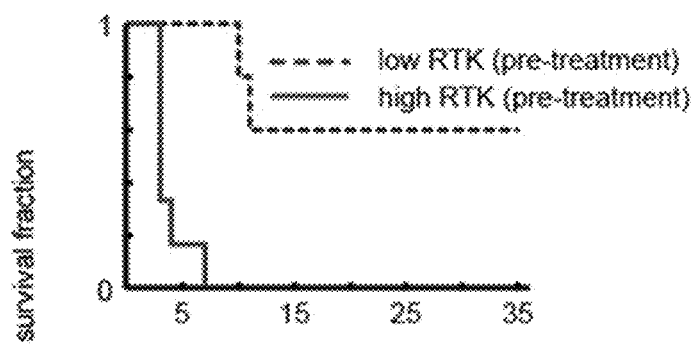
FIGS. 16 A-I illustrate that circulating RTKs correlate with BRAFi/MEKi resistance in melanoma patients, and co-treatment with AXLi extends progression free survival in mice. A) Plasma from melanoma patients was assayed for soluble RTK levels before and on treatment with dual BRAFi/MEKi therapy. B) Kaplan-Meier analysis based on average pre-treatment RTK levels (see A) correlates with PFS (p=0.005; two-tailed log-rank test). C) Kaplan-Meier analysis based on the change in RTK levels with therapy initiation (see A; average ratio, rightmost heatmap) correlates with PFS (p=0.005; two-tailed log-rank test). D) Correlation between change in RTK levels with therapy initiation and initial response as measured by RECIST criteria. Color corresponds to PFS. E) Immunohistochemistry for AXL (in brown) from tumor biopsies, corresponding to datapoints marker in D. F) Longitudinal plasma RTK levels monitored in the same patients shown in E. G-I) AXLi co-treatment synergistically increases BRAFi/MEKi efficacy in the LOX-IMVI xenograft model by enhancing initial tumor shrinkage (G; p=0.02, two-tailed t-test), delaying tumor recurrence (H; p=0.002, two-tailed t-test), and extending survival (I; p=0.03, two-tailed log-rank test), compared to treatment with BRAFi/MEKi alone.
Figure 16C:
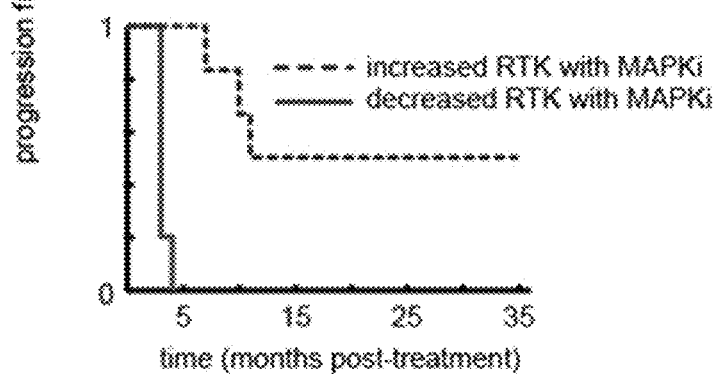
Figure 16D:
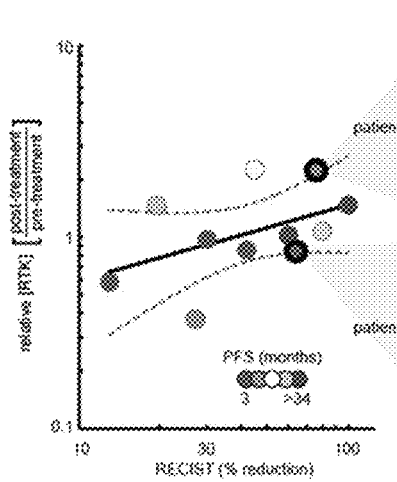

Circulating RTKs Correlate with MAPKi Resistance in Melanoma Patients, and Co-treatment with AXLi Extends Progression-free Survival in Mice Studies were performed to determine whether reduced RTK shedding was observable in patients undergoing MAPKi therapy, and whether markers of RTK shedding correlated with clinical outcomes. Plasma samples were collected from melanoma patients undergoing treatment with a combination of trametinib (MEKi) and dabrafenib (BRAFi), both before and while on treatment. As surrogate markers of RTK shedding, soluble levels of six RTKs known to be ADAM substrates: (MET, HER2, HER4, and the three TAM receptors AXL, MERTK, and TYRO3) were measured using solution-phase antibody arrays (FIG. 16A). With this non-invasive blood-based test, patients showing high combined levels of soluble RTKs initially before MAPKi treatment were found to exhibit rapid disease progression (FIG. 16B). Motivated by the hypothesis that reduced RTK shedding may lead to MAPKi resistance, the following were next examined: (a) whether circulating RTK levels changed with MAPKi treatment, and (b) whether changes correlated with disease progression. Five (5) out of eleven (11) patients, principally those with high initial circulating RTK levels, were found to show decreased circulating RTK levels with initiation of MAPKi treatment (FIG. 16A). Disease rapidly progressed in these patients (FIG. 16C). Although changes in circulating RTKs positively correlated with initial tumor response as measured by RECIST criteria (FIG. 16D), this correlation was not significant (p=0.14, n=11, two-tailed t-test). Importantly, however, initial response according to RECIST failed to reliably predict progression-free survival (PFS; p=0.08; n=11; two-tailed log-rank test), as observed in other cancers (Takahashi, R., et al., Early [18F] fluorodeoxyglucose positron emission tomography at two days of gefitinib treatment predicts clinical outcome in patients with adenocarcinoma of the lung. Clin Canc Res 18, 220-228 (2012)). In contrast, changes in RTK levels were effective in predicting PFS (p=0.005; n=11; two-tailed log-rank test).

Figure 16E:
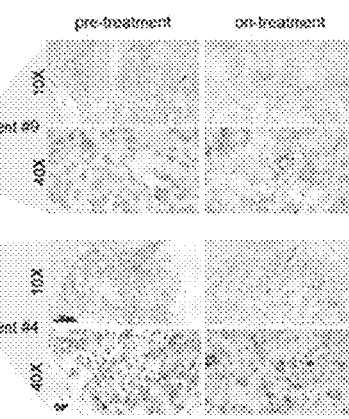
Figure 16F:
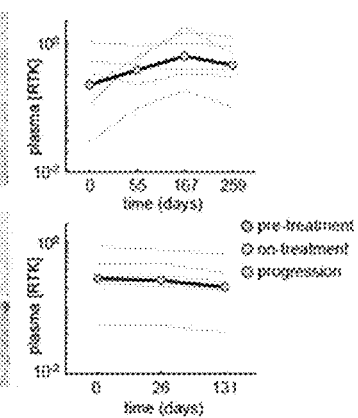

For a more detailed analysis, two patients that showed similar initial tumor response by RECIST, and yet very different plasma RTK patterns and disease progression, were further investigated. In one patient showing relatively long PFS (patient #9), low pre-treatment AXL levels in the primary tumor (FIG. 16E) corresponded to low pre-treatment AXL levels in the plasma (FIG. 16A). A sustained increase in AXL and other RTKs was detected in plasma (FIG. 16F) with MAPKi treatment initiation, and, indeed, AXL expression was detected at higher levels in the tumor (FIG. 16E). In contrast, another patient showing rapid disease progression (patient #4) exhibited high pre-treatment AXL levels both in plasma and in the primary tumor. Even though plasma AXL levels declined with MAPKi therapy (FIG. 16F), this patient exhibited sustained AXL levels in the primary tumor (FIG. 16E). This suggests that decreased circulating RTK levels do not simply reflect decreased expression in the primary tumor, but, instead, are likely indicating a decrease in RTK shedding. In sum, these results, combined with the aforementioned studies in the TNBC xenograft model, show that plasma RTK levels (a) can be non-invasively, quantitatively, and longitudinally monitored in patients undergoing MAPKi treatment; (b) reflect RTK levels at the primary tumor; and (c) provide an early indication of MAPKi efficacy, and may, consequently, have utility as a patient selection criterion.

Next, a new triple drug combination using MEKi+BRAFi (trametinib and vemurafenib) combined with the AXL inhibitor R428 (AXLi) was studied to investigate whether it might extend progression-free survival by compensating for drug resistance arising via AXL-mediated bypass signaling. Using a xenograft mouse model of melanoma, the addition of AXLi to the BRAFi/MEKi treatment regimen led to an enhanced initial tumor response (FIG. 16G), delayed tumor recurrence after the initial treatment course ended (FIG. 16H), and extended median overall survival time by more than a week (FIG. 16I). Notably, AXL treatment alone had no significant effect on overall survival (FIG. 16I), indicating a synergistic interaction between AXLi and BRAFi/MEKi. Overall, these results provide evidence that AXL mediates bypass signaling in response to BRAFi/MEKi treatment, contributes to drug resistance, and is therapeutically targetable using combination treatment regimens.

Example 8

Figure 17A:
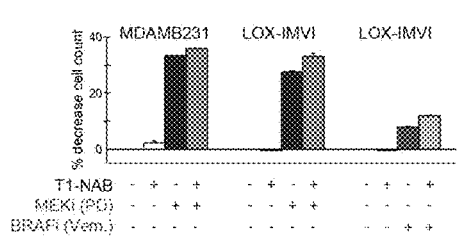
FIG. 17 A-D illustrate that MEK inhibition reduces sheddase activity via increased homodimerization and TIMP1 association, and TIMP1 neutralization enhances MAPKi efficacy. A-B) 24 h pre-treatment with a TIMP1 neutralization antibody (T1-NAB) followed by co-treatment with PD325901 or vemurafenib led to enhanced reduction in cell count at 72 h. B) Corresponding to A, T1-NAB co-treatment increases effect of BRAFi/MEKi, normalized to the effect-size of BRAFi/MEKi alone (*p=0.03, pooled two-tailed t-test, n=18 reps). C-D) T1-NAB co-treatment synergistically increases BRAFi/MEKi efficacy in the LOX-IMVI xenograft model by enhancing initial tumor shrinkage (C; p=0.014, two-way ANOVA interaction term), and delaying tumor recurrence (D; p=0.04, two-tailed t-test).
Figure 17B:
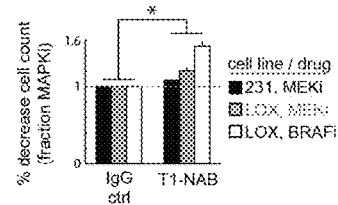
Figure 17C:
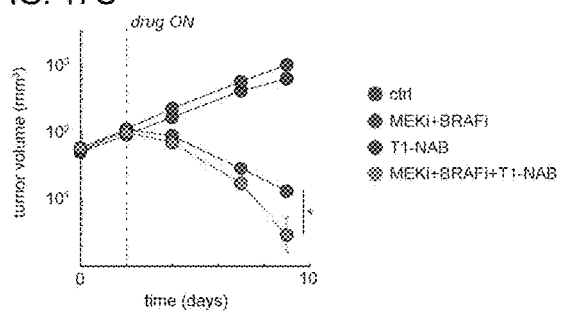
Figure 17D:
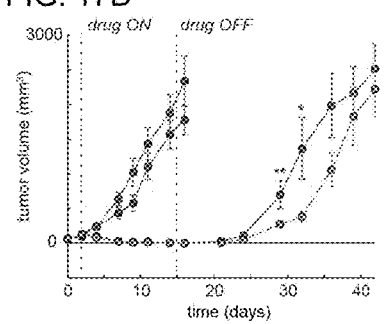

MEK Inhibition Enhances TIMP1 Association to Reduce Sheddase Activity, Causing Drug Resistance The role of TIMP1 in influencing therapeutic response to MAPKi was tested. Cells were co-treated with either MEKi or BRAFi (using vemurafenib) and a rabbit anti-human TIMP1 neutralizing antibody (T1-NAB) that binds TIMP1 and competitively prevents it from associating with proteases (T1-NAB AH2187 purchased from AbD Serotec Bio-Rad). While T1-NAB had no detectable effect on cell growth in the absence of MAPKi, it significantly increased the ability of MAPKi to reduce cell growth (FIG. 17A-B). For more clinical relevance, the effect of T1-NAB co-treatment was next examined in a melanoma xenograft model undergoing a combined MEKi/BRAFi inhibitor regimen similar to those used in the clinic. Results show that T1-NAB treatment alone had no deleterious effect on tumor growth. In contrast, T1-NAB significantly enhanced the ability of MEKi/BRAFi to initially reduce tumor size (FIG. 17C). Furthermore, T1-NAB extended the time to tumor recurrence after MEKi/BRAFi treatment had ended (FIG. 17D). Overall, these results provide evidence that reduced proteolytic shedding via TIMP1 association leads to mitigated MAPKi efficacy.

Methods:

In Vivo Tumor Growth and Metastasis Assays: All animal experiments and husbandry were approved by the MIT Division of Comparative Medicine. For orthotopic mammary transplant assays, 6-week-old female NOD/SCID-gamma mice (JAX) were anesthetized by i.p. injection of 125-250 mg/kg body weight of Avertin (reconstituted in PBS), followed by i.p. injection of 100 µL of 12 µg/mL buprenorphine for analgesia. A small incision was made on the right flank, and 250,000 MDA-MB231-LM2 cells in 25 µL of HBSS were injected into the right #4 fat pad using a 25-µL Hamilton syringe. Mice received three additional i.p. injections of 1004 of 12 µg/mL buprenorphine at 12 h intervals following the surgery. Initial sample size was chosen based on previously published experiments with MDA-MB231-LM2 xenograft models[25], as well as previously published data with the MEK and AXL drugs of interest[29-30]. 20 days post-surgery, when tumor size was palpable, mice were ranked by tumor size and semi-randomly divided into four groups of equal distribution in tumor size. Groups received one of four different drug treatments once daily for 21 days by oral gavage: vehicle (10% DMSO+0.5% methylcellulose+0.2% tween-80 in water), Axl inhibitor R428 at 30 mg/kg, PD0325901 ($C_{16}H_{14}F_3IN_2O_4$) at 1 mg/kg or a combination of both R428 at 30 mg/kg and PD0325901 at 1 mg/kg. Animals were sacrificed at the predetermined time of 21 days following initiation of drug treatment.

For the xenograft melanoma experiment, 7 week old female athymic nude mice (Taconic) were injected with $1\times10^6$ LOX-IMVI cells in 1:1 Matrigel:HBSS subcutaneously in each flank (Yang, D., et al. "RasGRP3, a Ras activator, contributes to signaling and the tumorigenic phenotype in human melanoma." Oncogene 30, no. 45: 4590-4600 (2011)). 7 days post-cell injection, tumors were measured by calipers and mice were ranked by tumor size and semi-randomly divided into 6 groups of equal distribution in tumor size, with 10 mice per group. Groups received one of four different drug treatments once daily for 14 days by oral gavage: vehicle (10% DMSO+0.5% methylcellulose+0.2% tween-80 in water), Axl inhibitor R428 at 30 mg/kg, PD0325901 at 1 mg/kg and Vemurafinib at 10 mg/kg or a combination of R428 at 30 mg/kg, PD0325901 at 1 mg/kg and Vemurafinib at 10 g/kg. To study the role TIMP1 in resistance to MAPKi, mice were treated with a TIMP1 neutralizing AB (AbD Serotec/Bio-Rad) at 32 mg/kg IP (Stilley, J. A., et al., Neutralizing TIMP1 restores fecundity in a rat model of endometriosis and treating control rats with TIMP1 causes anomalies in ovarian function and embryo development. Biol Reprod 83, 185-194 (2010)) daily for 3 days prior to starting drug treatment and then every second day during drug treatment. Mice were sacrificed when overall tumor burden reached more than 3 cm in diameter.

Tumor volumes was measured two to three times a week, estimated using the spherical tumor volume formula $V=4/3\pi r^3$, where r is averaged from 4 caliper measurements performed by two blinded researchers. Upon sacrifice, the lungs were inflated with and fixed in 3.7% (wt/vol) formaldehyde for 24 h, followed by 24 h in 75% (vol/vol) ethanol. For metastasis quantification, the numbers of metastases were counted in paraffin-embedded, H&E-stained sections, by a blinded researcher. Upon sacrifice, blood was collected via cardiac puncture into a heparinized syringe, immediately centrifuged at 2000×g for 20 min, and plasma fraction was stored at −80° C. for later quantification of receptor levels by ELISA and bead-based immunoassay.

For immunostaining primary tumor sections, tumors were formalin-fixed overnight and paraffin embedded. Tissue sections (5 µm thick) were deparaffinized followed by antigen retrieval using Citra Plus solution (Biogenex). Sections were incubated with primary antibodies for AXL (R&D systems, MAB154, 1:50) and MET (R&D systems, AF276, 1:20) overnight at 4° C. and fluorescently labeled secondary antibodies (AlexaFluor 594 and AlexaFluor 647, Jackson Immunoresearch) at room temperature for 2 h. Sections were mounted in Fluoromount mounting media and imaged at room temperature. Images (5×5 fields) were captured with a Nikon TE2000 microscope (TE2000, Nikon) with a 20× objective and a Photometrics Coolsnap HQ camera. AXL and MET staining was performed simultaneously across all samples, and imaging was performed in a single session using identical exposure settings. Exposure adjustments were made for DAPI staining shown in FIG. 6C.

MET and AXL levels were quantified by measuring fluorescent staining intensity over a line drawn radially from the tumor edge towards the tumor core. The very immediate edge of the tumor (0-30 um), which generally appeared to contain compacted tissue and/or highly auto-fluorescent adipose tissue with distinct morphology, was ignored. Therefore, the beginning of the "tumor edge" was defined here as the tumor region exhibiting regularly spaced nuclei determined through DAPI counter-staining (generally the 2nd or 3rd observable nucleus observable along the radial line by DAPI counter-stain intensity). Regions with morphology characteristic of stroma or necrosis were generally avoided during quantification. Peak intensities along the line were confirmed by visual inspection as corresponding to cell membranes, and were quantified and indexed according to the distance from the tumor edge. This process was repeated for n≥4 lines per tumor by a blinded researcher, and data were averaged accordingly. This was repeated across n≥3 separate tumors per treatment group, and average results for each tumor were background-corrected according to control tumor sections that were staining without primary antibody. Average results for each tumor then were used to calculate statistics between treatment groups, using the two-way student's t-test.

Exclusion criteria were used for the mice that were pre-determined at the onset of the experiment. Mice were excluded that failed to ever develop a tumor (n=4/37 for the TNBC model, n=1/60 for the melanoma model confirmed by dissection). All other mice had tumors on dissection. Among mice with successful tumor implantation, no significant difference was observed in pre-drug tumor volume across the four groups. One mouse asphyxiated during gavage treatment, all others survived for the duration of the experiment. Among mice with successful tumor implantation, two were excluded that exhibited a pre-drug tumor volume falling >2 standard deviations from the mean, across all groups (n=2/33 tumor-developing mice). Final sample sizes for the treatment groups, after exclusions described above, were n=7 controls, n=7 AXLi, and n=8 for the other groups.

In Vitro TIMP1 Neutralization: 5000 Cells Per Well were Plated in 96-Well plates overnight and treated with 10 ug/ml TIMP1 neutralization antibody (T1-NAB; ABD-Serotec/Bio-Rad) or IgG control for 24 h. The following day PD325901 was added to a final concentration of either 0.5 uM (MDAMB-231) or 5 uM (LOX-IMVI), or vemurafenib was added at 10 uM. 72 h after PD325901/vemurafenib treatment, cell count was assessed using the PrestoBlue assay (Life Technologies) according to manufacturer's guidelines.

Patient Samples. Patients with metastatic melanoma containing $BRAF^{V600E}$ mutation (confirmed by genotyping) were enrolled on clinical trials for treatment with a BRAF inhibitor or combined BRAF+MEK inhibitor (Table 1) at Massachusetts General Hospital and were consented for blood and tissue acquisition per IRB-approved protocol. Blood was collected and tumor biopsies were performed pre-treatment (day 0), 10-14 days on treatment, and/or at time of progression if applicable. Multiple on treatment blood samples were collected over the course of therapy as available. Plasma was isolated immediately from blood samples using BD Vacutainer CPT tube with Sodium Citrate (BD 362761). Formalin-fixed tissue from each tissue biopsy was analyzed to confirm that viable tumor was present via hematoxylin and eosin (H&E) staining.

TABLE 1

| PT | Mutation | RX | Dose (daily) |
|---|---|---|---|
| 1 | BRAF | dabrafenib + trametinib | GSK2118436: 300 mg, GSK1120212: 2 mg |
| 2 | BRAF | dabrafenib + trametinib | GSK2118436: 300 mg, GSK1120212: 1.5 mg |
| 3 | BRAF | dabrafenib + trametinib | GSK2118436: 200 mg, GSK1120212: 2 mg |
| 4 | BRAF | dabrafenib + trametinib | GSK2118436: 150 mg, GSK1120212: 2 mg |
| 5 | BRAF | dabrafenib + trametinib | GSK2118436: 200 mg, GSK1120212: 1.5 mg |
| 6 | BRAF | dabrafenib + trametinib | GSK2118436: 300 mg, GSK1120212: 2 mg |
| 7 | BRAF | dabrafenib + trametinib | GSK2118436: 300 mg, GSK1120212: 2 mg |
| 8 | BRAF | dabrafenib + trametinib | GSK2118436: 300 mg, GSK1120212: 1 mg |
| 9 | BRAF | LGX818 + MEK162 | LGX818: 400 mg, MEK162: 60 mg |
| 10 | BRAF | dabrafenib + trametinib | GSK2118436: 300 mg, GSK1120212: 2 mg |
| 11 | BRAF | dabrafenib + trametinib | GSK2118436: 300 mg, GSK1120212: 2 mg |

Clinical Response. RECIST criteria were used to classify response, and are defined as follows: Complete Response (CR): Disappearance of all target lesions. Partial Response (PR): At least a 30% decrease in the sum of the longest diameter (LD) of target lesions, taking as reference the baseline sum LD. Stable Disease (SD): Neither sufficient shrinkage to qualify for PR nor sufficient increase to qualify for PD, taking as reference the smallest sum LD since initiation of treatment. Progressive Disease (PD): At least a 20% increase in the sum of the LD of target lesions, taking as reference the smallest sum LD recorded since the treatment started or the appearance of one or more new lesions.

Immunohistochemistry. Tumor biopsies were stained with primary antibody to AXL (Cell Signaling 8661S) followed by a secondary antibody for horseradish peroxidase and then 3,3'-diaminobenzidine (DAB), as previously described(1).

Patient Sample RTK Analysis: Frozen aliquots of plasma were analyzed by bead-based immunoassays using duo-set antibodies from R&D Systems for the TAM receptors. Simultaneously, other RTKs were measured using multiplexed bead-based immunoassays from Millipore (RTK Mitogenesis Kit). Measurements were normalized to total protein content, measured by micro-BCA assay (Pierce).

REFERENCES

Akhavan, D., Pourzia, A. L., Nourian, A. A., Williams, K. J., Nathanson, D., Babic, I., Villa, G. R., Tanaka, K., Nael, A., Yang, H. et al. (2013). De-repression of PDGFRbeta transcription promotes acquired resistance to EGFR tyrosine kinase inhibitors in glioblastoma patients. Cancer Discov 3, 534-547.

Asai, M., Hattori, C., Szabo, B., Sasagawa, N., Maruyama, K., Tanuma, S., and Ishiura, S. (2003). Putative function of ADAMS, ADAM10, and ADAM17 as APP alpha-secretase. Biochem Biophys Res *Commun* 301, 231-235.

Barretina, J., Caponigro, G., Stransky, N., Venkatesan, K., Margolin, A. A., Kim, S., Wilson, C. J., Lehar, J., Kryukov, G. V., Sonkin, D. et al. (2012). The Cancer Cell Line Encyclopedia enables predictive modelling of anticancer drug sensitivity. Nature 483, 603-607.

Bartholomeusz, C., Gonzalez-Angulo, A. M., Liu, P., Hayashi, N., Lluch, A., Ferrer-Lozano, J., and Hortobagyi, G. N. (2012). High ERK protein expression levels correlate with shorter survival in triple-negative breast cancer patients. Oncologist 17, 766-774.

Bliss, C. I. (1939). The toxicity of poisons applied jointly1. Annals of applied biology 26, 585-615.

Byers, L. A., Diao, L., Wang, J., Saintigny, P., Girard, L., Peyton, M., Shen, L., Fan, Y., Giri, U., Tumula, P. K. et al. (2013). An epithelial-mesenchymal transition gene signature predicts resistance to EGFR and PI3K inhibitors and identifies Axl as a therapeutic target for overcoming EGFR inhibitor resistance. Clin Cancer Res 19, 279-290.

De Mattos-Arruda, L., Cortes, J., Santarpia, L., Vivancos, A., Tabernero, J., Reis-Filho, J. S., and Seoane, J. (2013). Circulating tumour cells and cell-free DNA as tools for managing breast cancer. Nat Rev Clin Oncol 10, 377-389.

Diaz-Rodriguez, E., Montero, J. C., Esparis-Ogando, A., Yuste, L., and Pandiella, A. (2002). Extracellular signal-regulated kinase phosphorylates tumor necrosis factor alpha-converting enzyme at threonine 735: a potential role in regulated shedding. Mol Biol Cell 13, 2031-2044.

Duffy, M. J., Mullooly, M., Crown J., McGowan P. J. (2013). The ADAMs: New Therapeutic Targets for Cancer? Cancer Targeted Drug Delivery, 273-287.

Duncan, J. S., Whittle, M. C., Nakamura, K., Abell, A. N., Midland, A. A., Zawistowski, J. S., Johnson, N. L., Granger, D. A., Jordan, N. V., Darr, D. B. et al. (2012). Dynamic reprogramming of the kinome in response to targeted MEK inhibition in triple-negative breast cancer. Cell 149, 307-321.

Efron B, Gong G. Amer Stat. 1983 February; 37(1):36-48.

Gilbert, L. A., and Hemann, M. T. (2010). DNA damage-mediated induction of a chemoresistant niche. Cell 143, 355-366.

Gooz, M. (2010). ADAM-17: the enzyme that does it all. Crit Rev Biochem Mol Biol 45, 146-169.

Greco W R, Bravo G, Parsons J C. Pharmacol Rev. 1995 June; 47(2):331-85.

Guo, L., Eisenman, J. R., Mahimkar, R. M., Peschon, J. J., Paxton, R. J., Black, R. A., and Johnson, R. S. (2002). A proteomic approach for the identification of cell-surface proteins shed by metalloproteases. Mol Cell Proteomics 1, 30-36.

Hoeflich, K. P., O'Brien, C., Boyd, Z., Cavet, G., Guerrero, S., Jung, K., Januario, T., Savage, H., Punnoose, E., Truong, T. et al. (2009). In vivo antitumor activity of MEK and phosphatidylinositol 3-kinase inhibitors in basal-like breast cancer models. Clin Cancer Res 15, 4649-4664.

Holland, S. J., Pan, A., Franci, C., Hu, Y., Chang, B., Li, W., Duan, M., Torneros, A., Yu, J., Heckrodt, T. J. et al. (2010). R428, a selective small molecule inhibitor of Axl kinase, blocks tumor spread and prolongs survival in models of metastatic breast cancer. Cancer Res 70, 1544-1554.

Johannessen, C. M., Boehm, J. S., Kim, S. Y., Thomas, S. R., Wardwell, L., Johnson, L. A., Emery, C. M., Stransky, N., Cogdill, A. P., Barretina, J. et al. (2010). COT drives resistance to RAF inhibition through MAP kinase pathway reactivation. Nature 468, 968-972.

Johannessen, C. M., Johnson, L. A., Piccioni, F., Townes, A., Frederick, D. T., Donahue, M. K., Narayan, R., Flaherty, K. T., Wargo, J. A., Root, D. E. et al. (2013). A melanocyte lineage program confers resistance to MAP kinase pathway inhibition. Nature 504, 138-142.

Liu, L., Greger, J., Shi, H., Liu, Y., Greshock, J., Annan, R., Halsey, W., Sathe, G. M., Martin, A. M., and Gilmer, T. M. (2009). Novel mechanism of lapatinib resistance in HER2-positive breast tumor cells: activation of AXL. Cancer Res 69, 6871-6878.

McGowan, P. M., Ryan, B. M., Hill, A. D., McDermott, E., O'Higgins, N., and Duffy, M. J. (2007). ADAM-17 expression in breast cancer correlates with variables of tumor progression. Clin Cancer Res 13, 2335-2343.

Meyer, A. S., Miller, M. A., Gertler, F. B., and Lauffenburger, D. A. (2013). The receptor AXL diversifies EGFR signaling and limits the response to EGFR-targeted inhibitors in triple-negative breast cancer cells. Sci Signal 6, ra66.

Michieli, P., Mazzone, M., Basilico, C., Cavassa, S., Sottile, A., Naldini, L., and Comoglio, P. M. (2004). Targeting the tumor and its microenvironment by a dual-function decoy Met receptor. Cancer Cell 6, 61-73.

Miller, M. A., Barkal, L., Jeng, K., Herrlich, A., Moss, M., Griffith, L. G., and Lauffenburger, D. A. (2011). Proteolytic Activity Matrix Analysis (PrAMA) for simultaneous determination of multiple protease activities. Integr Biol (Camb) 3, 422-438.

Miller, M. A., Meyer, A. S., Beste, M. T., Lasisi, Z., Reddy, S., Jeng, K. W., Chen, C. H., Han, J., Isaacson, K., Griffith, L. G. et al. (2013). ADAM-10 and -17 regulate endometriotic cell migration via concerted ligand and receptor shedding feedback on kinase signaling. Proc Natl Acad Sci USA 110, E2074-E2083.

Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518-524.

Muranen, T., Selfors, L. M., Worster, D. T., Iwanicki, M. P., Song, L., Morales, F. C., Gao, S., Mills, G. B., and Brugge, J. S. (2012). Inhibition of PI3K/mTOR leads to adaptive resistance in matrix-attached cancer cells. Cancer Cell 21, 227-239.

Nazarian, R., Shi, H., Wang, Q., Kong, X., Koya, R. C., Lee, H., Chen, Z., Lee, M. K., Attar, N., Sazegar, H. et al. (2010). Melanomas acquire resistance to B-RAF (V600E) inhibition by RTK or N-RAS upregulation. Nature 468, 973-977.

Oxnard, G. R., Arcila, M. E., Sima, C. S., Riely, G. J., Chmielecki, J., Kris, M. G., Pao, W., Ladanyi, M., and Miller, V. A. (2011). Acquired resistance to EGFR tyrosine kinase inhibitors in EGFR-mutant lung cancer: distinct natural history of patients with tumors harboring the T790M mutation. Clin Cancer Res 17, 1616-1622.

Serra, V., Scaltriti, M., Prudkin, L., Eichhorn, P. J., Ibrahim, Y. H., Chandarlapaty, S., Markman, B., Rodriguez, O., Guzman, M., Rodriguez, S. et al. (2011). PI3K inhibition results in enhanced HER signaling and acquired ERK dependency in HER2-overexpressing breast cancer. Oncogene 30, 2547-2557.

Sheridan, C. (2013). First Axl inhibitor enters clinical trials. Nat Biotechnol 31, 775-776.

Soond, S. M., Everson, B., Riches, D. W., and Murphy, G. (2005). ERK-mediated phosphorylation of Thr735 in TNFalpha-converting enzyme and its potential role in TACE protein trafficking J Cell Sci 118, 2371-2380.

Storey, J. D. (2002). A direct approach to false discovery rates. Journal of the Royal Statistical Society: Series B (Statistical Methodology) 64, 479-498.

Straussman, R., Morikawa, T., Shee, K., Barzily-Rokni, M., Qian, Z. R., Du, J., Davis, A., Mongare, M. M., Gould, J., Frederick, D. T. et al. (2012). Tumour microenvironment elicits innate resistance to RAF inhibitors through HGF secretion. Nature 487, 500-504.

Subramanian, A., Tamayo, P., Mootha, V. K., Mukherjee, S., Ebert, B. L., Gillette, M. A., Paulovich, A., Pomeroy, S. L., Golub, T. R., Lander, E. S. et al. (2005). Gene set enrichment analysis: a knowledge-based approach for interpreting genome-wide expression profiles. Proc Natl Acad Sci USA 102, 15545-15550.

Swendeman, S., Mendelson, K., Weskamp, G., Horiuchi, K., Deutsch, U., Scherle, P., Hooper, A., Rafii, S., and Blobel, C. P. (2008). VEGF-A stimulates ADAM17-dependent shedding of VEGFR2 and crosstalk between VEGFR2 and ERK signaling. Circ Res 103, 916-918.

To, K., Fotovati, A., Reipas, K. M., Law, J. H., Hu, K., Wang, J., Astanehe, A., Davies, A. H., Lee, L., Stratford, A. L. et al. (2010). Y-box binding protein-1 induces the expression of CD44 and CD49f leading to enhanced self-renewal, mammosphere growth, and drug resistance. Cancer Res 70, 2840-2851.

Turke, A. B., Song, Y., Costa, C., Cook, R., Arteaga, C. L., Asara, J. M., and Engelman, J. A. (2012). MEK inhibition leads to PI3K/AKT activation by relieving a negative feedback on ERBB receptors. Cancer Res 72, 3228-3237.

Turke, A. B., Zejnullahu, K., Wu, Y. L., Song, Y., Dias-Santagata, D., Lifshits, E., Toschi, L., Rogers, A., Mok, T., Sequist, L. et al. (2010). Preexistence and clonal selection of MET amplification in EGFR mutant NSCLC. Cancer Cell 17, 77-88.

Watson, J. V., Chambers, S. H., and Smith, P. J. (1987). A pragmatic approach to the analysis of DNA histograms with a definable G1 peak. Cytometry 8, 1-8.

Wilson, T. R., Fridlyand, J., Yan, Y., Penuel, E., Burton, L., Chan, E., Peng, J., Lin, E., Wang, Y., Sosman, J. et al. (2012). Widespread potential for growth-factor-driven resistance to anticancer kinase inhibitors. Nature 487, 505-509.

Xu, P., and Derynck, R. (2010). Direct activation of TACE-mediated ectodomain shedding by p38 MAP kinase regulates EGF receptor-dependent cell proliferation. Mol Cell 37, 551-566.

Xu, P., Liu, J., Sakaki-Yumoto, M., and Derynck, R. (2012). TACE activation by MAPK-mediated regulation of cell surface dimerization and TIMP3 association. Sci Signal 5, ra34.

Ye, X., Li, Y., Stawicki, S., Couto, S., Eastham-Anderson, J., Kallop, D., Weimer, R., Wu, Y., and Pei, L. (2010). An anti-Axl monoclonal antibody attenuates xenograft tumor growth and enhances the effect of multiple anticancer therapies. Oncogene 29, 5254-5264.

Zardavas, D., Baselga, J., and Piccart, M. (2013). Emerging targeted agents in metastatic breast cancer. Nat Rev Clin Oncol 10, 191-210.

Zhang, Z., Lee, J. C., Lin, L., Olivas, V., Au, V., LaFramboise, T., Abdel-Rahman, M., Wang, X., Levine, A. D., Rho, J. K. et al. (2012). Activation of the AXL kinase causes resistance to EGFR-targeted therapy in lung cancer. Nat Genet 44, 852-860.

Zhang, Z., Lee, J. C., Lin, L., Olivas, V., Au, V., LaFramboise, T., Abdel-Rahman, M., Wang, X., Levine, A. D., Rho, J. K. et al. (2012). Activation of the AXL kinase causes resistance to EGFR-targeted therapy in lung cancer. Nat Genet 44, 852-860.

Miller, Miles Aaron. Understanding and Targeting Network-Level Sheddase Regulation in Invasive Disease. MIT, Submitted to the Department of Biological Engineering in partial fulfillment of the requirements for the degree of Doctor of Philosophy Thesis, 2013.

Konieczkowski D J, Johannessen C M, Abudayyeh O, Kim J W, Cooper Z A, Piris A, et al. A melanoma cell state distinction influences sensitivity to MAPK pathway inhibitors. Cancer discovery. 2014; 4:816-27.

Stilley, J. A., Birt, J. A., Nagel, S. C., Sutovsky, M., Sutovsky, P., and Sharpe-Timms, K. L. (2010). Neutralizing TIMP1 restores fecundity in a rat model of endometriosis and treating control rats with TIMP1 causes anomalies in ovarian function and embryo development. Biol Reprod 83, 185-194.

Takahashi, R., Hirata, H., Tachibana, I., Shimosegawa, E., Inoue, A., Nagatomo, I., Takeda, Y., Kida, H., Goya, S., Kijima, T., et al. (2012) Early [18F] fluorodeoxyglucose positron emission tomography at two days of gefitinib treatment predicts clinical outcome in patients with adenocarcinoma of the lung. Clin Canc Res 18, 220-228.

Yang, Dazhi, Juan Tao, Luowei Li, Noemi Kedei, Zsuzsanna E. Toth, Alexandra Czap, Julia F. Velasquez et al. "RasGRP3, a Ras activator, contributes to signaling and the tumorigenic phenotype in human melanoma." *Oncogene* 30, no. 45 (2011): 4590-4600.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a cancer in an individual comprising administering a therapeutically effective amount of a MEK1/2 inhibitor and an AXL inhibitor,
    wherein the MEK1/2 inhibitor is selected from the group consisting of PD325901, AZD6244 (selumetinib), and trametinib (GSK1120212): and
    wherein the AXL inhibitor is selected from the group consisting of R428, MP-470 (amuvatinib), and XL-880 (foretinib).

2. The method of claim 1, further comprising administering an additional therapeutic agent.

3. A method of treating a cancer in an individual comprising administering a therapeutically effective amount of a MEK1/2 inhibitor, an AXL inhibitor and a tissue inhibitor of metalloproteinase 1 (TIMP1) inhibitor.

4. The method of claim 3, wherein the tissue inhibitor of metalloproteinase 1 (TIMP1) inhibitor is a TIMP1 neutralizing antibody.

5. The method of claim 1, wherein the cancer is a carcinoma, sarcoma, lymphoma, leukemia, or blastoma.

6. The method of claim 5, wherein the carcinoma is a breast cancer, a melanoma, a lung cancer or an ovarian cancer.

7. The method of claim 6, wherein the breast cancer expresses low estrogen receptor, progesterone receptor, HER2, or a combination thereof triple-negative breast cancer (TNBC).

8. The method of claim 5, wherein the blastoma is glioblastoma multiforme.

9. The method of claim 1, wherein the MEK1/2 inhibitor is administered to the individual at or near the same time as the AXL inhibitor.

10. The method of claim 1, wherein the MEK1/2 inhibitor is administered before or after administration of the AXL inhibitor to the individual.

11. The method of claim 1, wherein the MEK1/2 inhibitor and the AXL inhibitor are administered to the individual in a single formulation.

12. The method of claim 1, wherein the MEK1/2 inhibitor and the AXL inhibitor are administered to the individual in different formulations.

13. The method of claim 1, wherein administering the MEK1/2 inhibitor and AXL inhibitor reduces tumor growth in the individual.

14. The method of claim 1, wherein administering the MEK1/2 inhibitor and AXL inhibitor reduces metastasis in the individual.

15. A method of treating a cancer in an individual comprising administering a therapeutically effective amount of a MEK inhibitor, an AXL inhibitor, and a BRAF inhibitor, wherein the MEK1/2 inhibitor is selected from the group consisting of PD325901, AZD6244 (selumetinib), and trametinib (GSK1120212); and wherein the AXL inhibitor is selected from the group consisting of R428, MP-470 (amuvatinib), and XL-880 (foretinib).

16. The method of claim 1, wherein the AXL inhibitor is R428.

17. The method of claim 1, wherein the MEK1/2 inhibitor is PD325901 or AZD6244 (selumetinib).

18. The method of claim 15, wherein the MEK1/2 inhibitor is PD325901 or AZD6244 (selumetinib).

19. The method of claim 1, wherein the MEK1/2 inhibitor is PD325901 or AZD6244 (selumetinib) and wherein the AXL inhibitor is R428.

20. The method of claim 15, wherein the AXL inhibitor R428.

21. The method of claim 15, wherein the MEK1/2 inhibitor is PD325901 or AZD6244 (selumetinib) and wherein the AXL inhibitor is R428.

* * * * *